(12) United States Patent
Yabe et al.

(10) Patent No.: US 8,178,215 B2
(45) Date of Patent: May 15, 2012

(54) ORGANIC COMPOUND CONTAINING AT LEAST TWO CARBAZOLYL-SUBSTITUTED PHENYL STRUCTURES; CHARGE-TRANSPORTING MATERIAL AND ORGANIC EL ELEMENT CONTAINING THE COMPOUND

(75) Inventors: Masayoshi Yabe, Kanagawa (JP); Hideki Sato, Kanagawa (JP); Masako Takeuchi, Kanagawa (JP); Masayo Fugono, Kanagawa (JP); Koichiro Iida, Kanagawa (JP)

(73) Assignees: Pioneer Corporation, Tokyo (JP); Mitsubishi Chemical Corporation, Tokyo (JP)

( * ) Notice: Subject to any disclaimer, the term of this patent is extended or adjusted under 35 U.S.C. 154(b) by 807 days.

(21) Appl. No.: 11/721,401

(22) PCT Filed: Dec. 5, 2005

(86) PCT No.: PCT/JP2005/022298
§ 371 (c)(1),
(2), (4) Date: Jun. 11, 2007

(87) PCT Pub. No.: WO2006/062062
PCT Pub. Date: Jun. 15, 2006

(65) Prior Publication Data
US 2009/0236973 A1 Sep. 24, 2009

(30) Foreign Application Priority Data
Dec. 10, 2004 (JP) ................. 2004-358592

(51) Int. Cl.
*H01J 1/63* (2006.01)
*C07D 401/14* (2006.01)
(52) U.S. Cl. ...... 428/690; 428/917; 313/502; 546/276.7
(58) Field of Classification Search .................. None
See application file for complete search history.

(56) References Cited

U.S. PATENT DOCUMENTS

| | | | |
|---|---|---|---|
| 7,829,204 B2 | 11/2010 | Iwakuma et al. | |
| 2004/0086745 A1 | 5/2004 | Iwakuma et al. | |
| 2004/0110031 A1 | 6/2004 | Fukuda et al. | |
| 2005/0127823 A1 | 6/2005 | Iwakuma et al. | |
| 2005/0158578 A1* | 7/2005 | Iwakuma et al. | 428/690 |
| 2005/0249976 A1 | 11/2005 | Iwakuma et al. | |
| 2006/0186796 A1 | 8/2006 | Yabe et al. | |
| 2007/0159083 A1 | 7/2007 | Matsuura et al. | |

FOREIGN PATENT DOCUMENTS

| | | |
|---|---|---|
| CN | 1918947 A | 2/2007 |
| CN | 1934213 A | 3/2007 |
| EP | 0 517 542 A1 | 12/1992 |
| EP | 1672961 A1 | 6/2006 |
| EP | 1 718 121 A1 | 11/2006 |
| EP | 1 724 323 A1 | 11/2006 |
| EP | 1829871 A1 | 9/2007 |
| EP | 1857521 A1 | 11/2007 |
| EP | 1885008 A1 | 2/2008 |
| EP | 1887640 A1 | 2/2008 |
| JP | 6 1972 | 1/1994 |
| JP | 2000-169448 | 6/2000 |
| JP | 2000 169448 | 6/2000 |
| JP | 2000-186066 | 7/2000 |
| JP | 2000 186066 | 7/2000 |
| JP | 2003 22893 | 1/2003 |
| JP | 2003-022893 | 1/2003 |
| JP | 2004 71380 | 3/2004 |
| JP | 2004-071380 | 3/2004 |
| JP | 2004-171808 | 6/2004 |
| JP | 2004 311413 | 11/2004 |
| JP | 2004-311413 | 11/2004 |
| WO | 2005/057987 A1 | 6/2005 |
| WO | 2005 076669 | 8/2005 |
| WO | 2005 079118 | 8/2005 |
| WO | 2005 085387 | 9/2005 |

(Continued)

OTHER PUBLICATIONS

Solomons, G., & Fryhle, C. (2000). Organic Chemistry Seventh Edition. New York, New York: John Wiley & Sons, Inc. pp. 676-691.*

(Continued)

*Primary Examiner* — Lynda Salvatore
*Assistant Examiner* — Andrew K Bohaty
(74) *Attorney, Agent, or Firm* — Oblon, Spivak, McClelland, Maier & Neustadt, L.L.P.

(57) ABSTRACT

An organic compound and a charge-transporting material which are excellent in both a hole-transporting property and an electron-transporting property and have excellent electrical oxidation/reduction durability and a high triplet excitation level are provided, and an organic electroluminescent device which uses this organic compound and has high luminous efficiency and high driving stability and long lifetime is provided, wherein the organic compound has two or more partial structures represented by the following Formula (I):

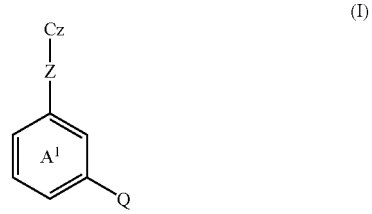

wherein Cz denotes a carbazolyl group; Z is as defined; and Q denotes a direct link connected to G present in a moiety represented by the following Formula (II):

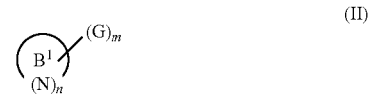

wherein $B^1$ ring is a six-membered aromatic heterocycle containing n N atoms as a hetero atom; n is an integer of 1 to 3; G is as defined; and m is an integer of 3 to 5.

30 Claims, 2 Drawing Sheets

FOREIGN PATENT DOCUMENTS

| | | |
|---|---|---|
| JP | 2005 85658 | 3/2005 |
| JP | 2005-085658 | 3/2005 |
| WO | 03 078541 | 9/2003 |
| WO | 03 080760 | 10/2003 |
| WO | WO 03080761 A1 * | 10/2003 |
| WO | 2005 022962 | 3/2005 |

OTHER PUBLICATIONS

Baldo, et al.,"Very High-efficiency Green Organic Light-emitting Devices Based on Electrophosphorescence ", Applied Physics Letters, vol. 75, No. 1, pp. 4-6, 1999.

Office Action issued May 30, 2011, in Korean Patent Application No. 10-2007-7013039, filed Aug. 27, 2007.

Office Action issued Sep. 1, 2011 in China Application No. 200580042418.8 (With English Translation).

R.J. Holmes, et al., Applied Physics Letters, vol. 82, No. 15, pp. 2422-2424 (Apr. 14, 2003).

Office Action issued Jan. 31, 2012, in Japanese Patent Application No. 2005-350623 filed Dec. 5, 2005.

* cited by examiner

ORGANIC COMPOUND CONTAINING AT LEAST TWO CARBAZOLYL-SUBSTITUTED PHENYL STRUCTURES; CHARGE-TRANSPORTING MATERIAL AND ORGANIC EL ELEMENT CONTAINING THE COMPOUND

TECHNICAL FIELD

The present invention relates to organic compounds and charge-transporting materials and relates to organic electroluminescent elements using these organic compounds.

BACKGROUND ART

Electroluminescent devices using organic thin films have been developed. An electroluminescent device using an organic thin film, namely, an organic electroluminescent device, generally includes an anode, a cathode, and an organic layer on a substrate. The organic layer is disposed between the anode and the cathode and contains at least a light-emitting layer. The organic layer is provided with, in addition to the light-emitting layer, a hole injection layer (anode buffer layer), a hole transport layer, a hole blocking layer, an electron transport layer, and an electron injection layer. In general, an organic electroluminescent device is constituted by laminating these layers between an anode and a cathode.

In known organic electroluminescent devices, fluorescence has been used. As an attempt to increase the luminous efficiency of a device, phosphorescence has been investigated to be used instead of fluorescence. However, sufficient luminous efficiency has not been practically achieved even if phosphorescence is used.

In many of known organic electroluminescent devices using phosphorescent molecules, materials containing carbazolyl groups are used as materials (host material) for the light-emitting layers. For example, in Appl. Phys. Lett., vol. 75, p. 4, 1999, a biphenyl derivative shown bellow is disclosed as a host material.

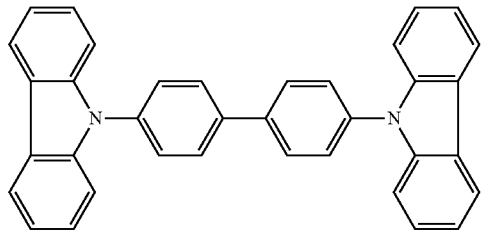

[Compound 1]

In an organic electroluminescent device using the above-mentioned biphenyl derivative, there is a tendency that recombination of charge carriers occurs at the cathode side and is not well balanced. Therefore, high luminous efficiency is not achieved.

In Japanese Unexamined Patent Application Publication No. 6-1972, it is disclosed that a compound shown below is used as an organic electroluminescent device.

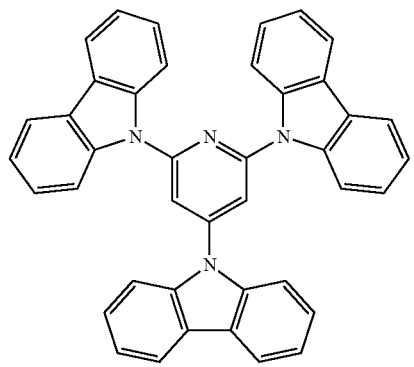

[Compound 2]

This compound is observed to emit light under a high voltage only and is thought that the luminance and luminous efficiency are insufficient.

In Japanese Unexamined Patent Application Publication No. 2000-186066 and Japanese Unexamined Patent Application Publication No. 2000-169448, it is disclosed that a pyridine compound shown below is used as a fluorescent element or a hole-transporting material and/or a light-emitting layer material of an electrophotographic photoreceptor.

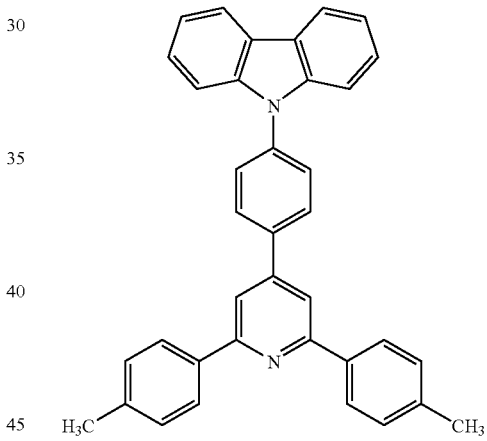

[Compound 3]

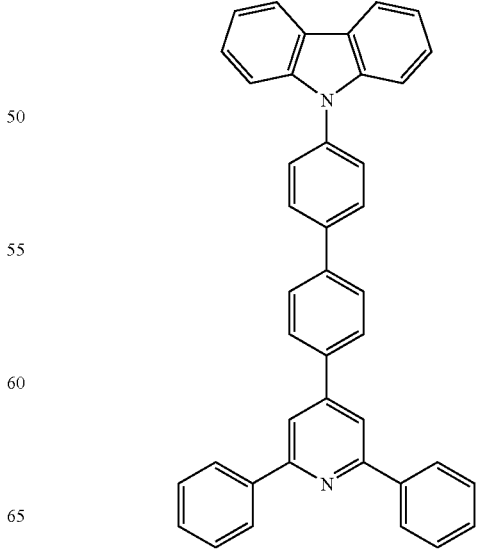

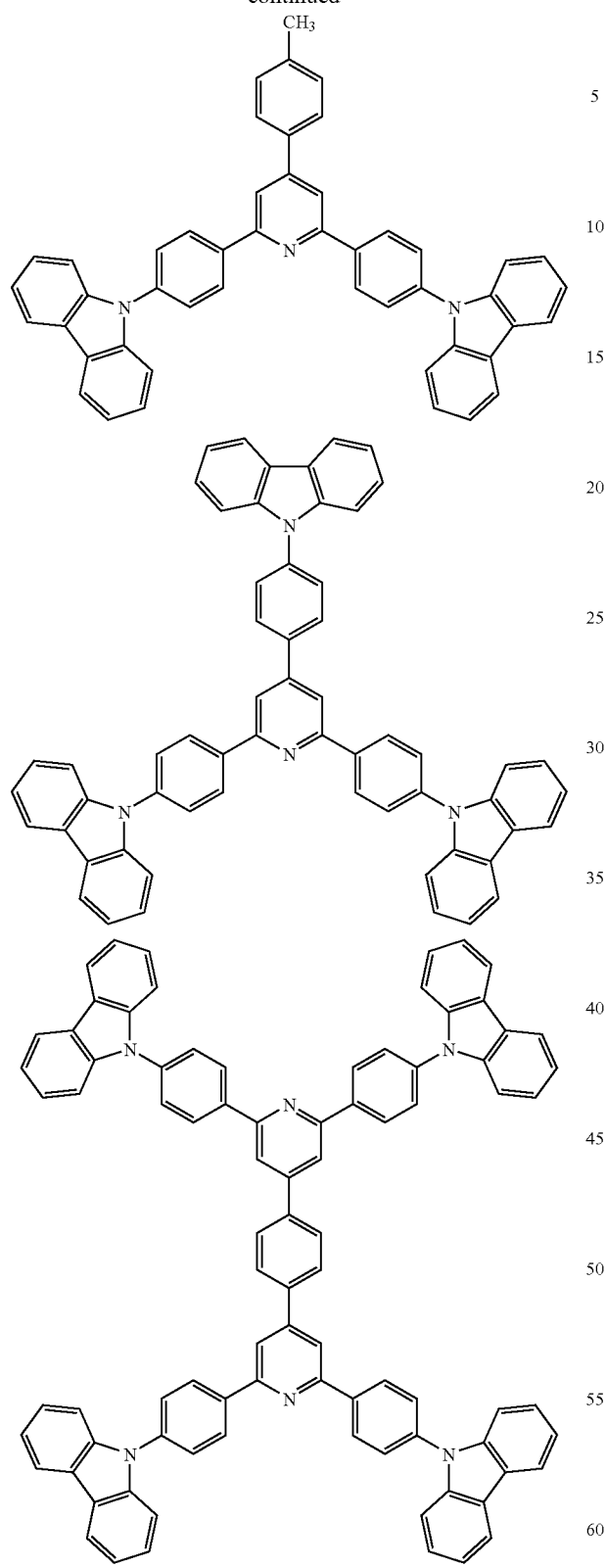
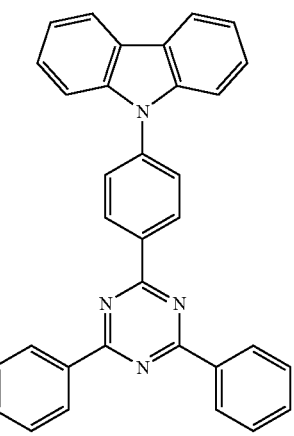
In International Patent Publication No. WO03/078541, it is disclosed that a compound shown below is used as a material for an organic electroluminescent device.
[Compound 5]
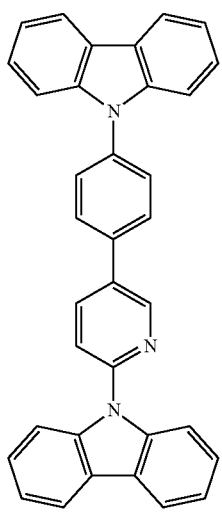
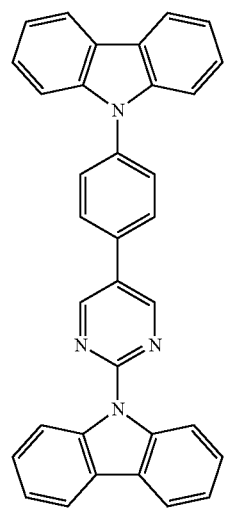
In Japanese Unexamined Patent Application Publication No. 2003-22893, it is disclosed that a compound shown below is used as a material for an organic electroluminescent device.

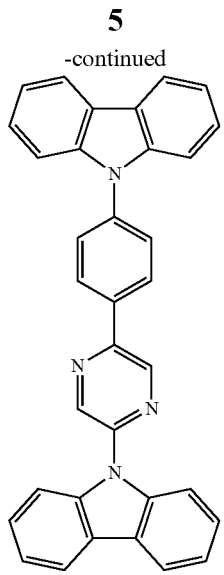

The compounds disclosed in these patent documents each include a structure in which a nitrogen atom in a carbazole ring can conjugate with a nitrogen atom in a pyridine ring, triazine ring, pyrimidine ring, or pyrazine ring. Therefore, polarization phenomenon of charges in molecules is significant and the triplet excitation level is relatively low. In addition, the durability of these compounds is not sufficient as a material for an organic electroluminescent element. Therefore, the performance of the compounds is insufficient for being applied to a blue light-emitting device or a phosphorescence-emitting device. Further, when compounds do not have a structure in which all of 2,4,6-positions of pyridine ring, 2,4,6-positions of pyrimidine ring, or 2,3,5,6-positions of pyrazine ring are substituted with substituents, the compounds are low in electrochemical durability.

In International Patent Publication No. WO03/080760, it is disclosed that a compound shown below is used as a material for an organic electroluminescent device.

[Compound 6]

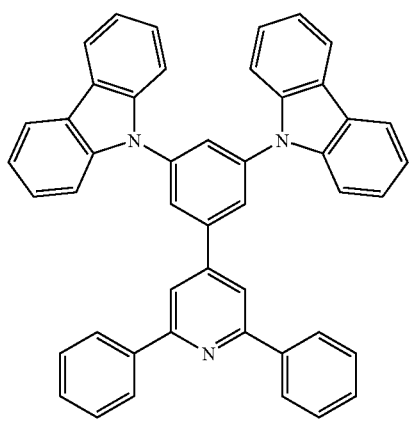

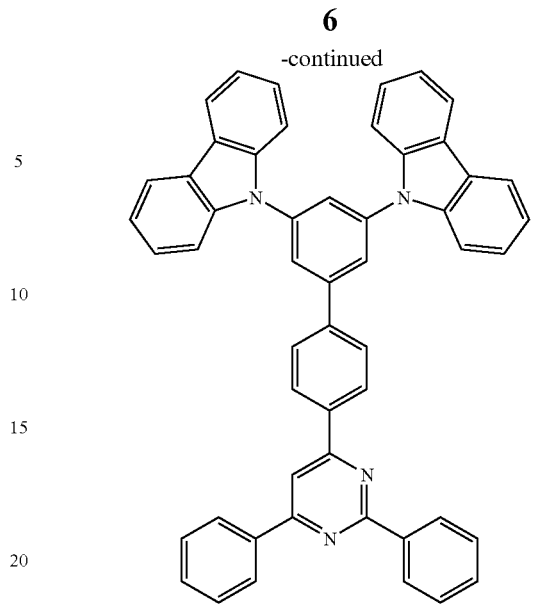

In these compounds, one aromatic ring (here, a benzene ring) has two carbazolyl groups (which are electron-donating groups) located in the meta-position (m-position) of the aromatic ring not to conjugate with each other. Therefore, positive or negative charges are readily localized by electrically oxidizing or reducing the molecules. Therefore, these compounds are lack of durability against electrical oxidization/reduction. In addition, a pyridine ring or a pyrimidine ring is introduced to these compounds in order to improve the durability against electrical reduction. However, when an aromatic ring (here, a benzene ring) has two carbazolyl groups as substituents, the aromatic ring is located in the p-position with respect to the nitrogen atom in a pyridine ring or a pyrimidine ring and can conjugate with the pyridine ring or the pyrimidine ring. Consequently, due to the electron-donating effect of the aromatic ring to the pyridine ring or the pyrimidine ring, the pyridine ring and the pyrimidine ring are low in durability against electrical reduction.

International Patent Publication No. WO03/080760 discloses a compound shown below.

[Compound 7]

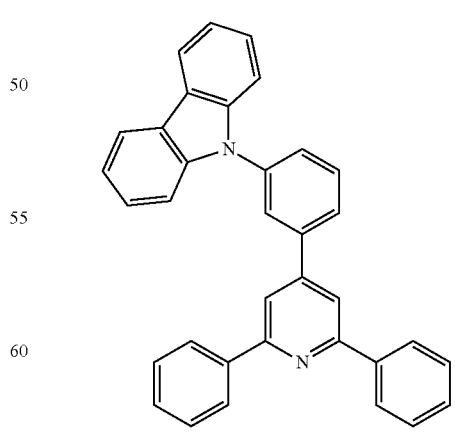

However, though it is predicted that the above-mentioned compound is improved in durability against electrical oxidization, the number of the carbazolyl group is only one and the hole-transporting property is thereby low. Consequently, the hole-transporting property and the electron transporting property are not well balanced as a material for a light-emitting layer of an organic electroluminescent device, and the compound is required to be improved when it is used as a host material. In addition, the compound has defects in the viewpoint of heat resistance, which is significant in a practical use.

DISCLOSURE OF INVENTION

It is an object of the present invention to provide an organic compound and a charge-transporting material which are excellent in both a hole-transporting property and an electron-transporting property and have excellent electrical oxidation/reduction durability and a high triplet excitation level, and to provide an organic electroluminescent device using this organic compound and having high luminous efficiency and high driving stability and long lifetime.

In an organic compound in accordance with a first aspect of the present invention, one molecule of the organic compound has two or more partial structures represented by Formula (I) shown below.

A charge-transporting material in accordance with a second aspect of the present invention contains this organic compound.

An organic electroluminescent device in accordance with a third aspect of the present invention includes an anode, a cathode, and an organic light-emitting layer disposed between the both electrodes on a substrate. The organic electroluminescent device contains the organic compound according to the first aspect. This organic compound layer may be an organic light-emitting layer.

The organic compound according to the first aspect is excellent in both a hole-transporting property and an electron-transporting property and has excellent electrical oxidation/reduction durability and a high triplet excitation level. The organic electroluminescent device containing this organic compound has high luminous efficiency and high driving stability and long lifetime.

[Compound 8]

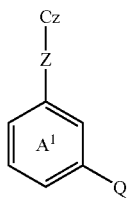

(I)

In the Formula, Cz denotes a carbazolyl group.

Z denotes a direct link or an optional linking group.

Cz, Z, and an $A^1$ ring may have a substituent.

One molecule contains a plurality of Cz's which may be the same or different.

One molecule contains a plurality of Z's which may be the same or different.

One molecule contains a plurality of $A^1$ rings which may be the same or different.

N atoms present in one molecule do not conjugate with each other excepting between N atoms in the same $B^1$ rings.

One molecule contains only one pyridine ring.

Q denotes a direct link connecting to G present in a moiety represented by the following Formula (II). One molecule contains a plurality of Q's.

[Compound 9]

(II)

In the Formula, $B^1$ ring is a six-membered aromatic heterocycle containing n N atoms as a hetero atom.

n is an integer of 1 to 3.

When G is linked to Q, the G denotes a direct link or an optional linking group which links to Q.

When G is not linked to Q, the G denotes an aromatic hydrocarbon group.

G's are bound to C atoms which are located in ortho-position and para-position with respect to the N atom in $B^1$ ring.

m is an integer of 3 to 5.

One molecule contains a plurality of G's which may be the same or different.

$B^1$ ring may have one or two substituents in addition to G.

As described above, the organic compound according to the present invention is excellent in both a hole-transporting property and an electron-transporting property and has excellent electrical oxidation/reduction durability and a high triplet excitation level. Consequently, an organic electroluminescent element using the organic compound according to the present invention can emit a light at high luminance and high efficiency, and the stability of the element, in particular, driving stability, is improved to achieve long lifetime.

The organic electroluminescent device using the organic compound according to the present invention can be applied to a flat panel display (for example, one used in an OA computer or a wall-hanging television), a car-mounted display device, a mobile phone display, a light source taking advantage of a characteristic as a plane illuminant (for example, a light source for a copier or a backlight liquid-crystal display or instrument), a display board, or a marker lamp.

Since the organic compound according to the present invention has essentially excellent stability to oxidation and reduction, it is useful to apply the organic compound not only to an organic electroluminescent device but also to an electrophotographic photoreceptor.

The organic compound according to the present invention is useful not only as a charge-transporting material but also as various types of emitting materials, a solar cell material, a battery material (electrolyte, electrode, separation film, and stabilizer), a medical application material, a painting material, a coating material, an organic semiconductor material, a toiletry material, an antistatic material, and a thermoelectric element material.

Since a charge-transporting material according to the present invention has excellent heat resistance, film-forming property, charge-transporting property, and luminous property, the charge-transporting material is also applicable as a hole injection material, a hole-transporting material, a light-emitting material, a host material, an electron injection material, or an electron-transmitting material depending on the layer structure of a device.

BEST MODE FOR CARRYING OUT THE INVENTION

Figure 1:
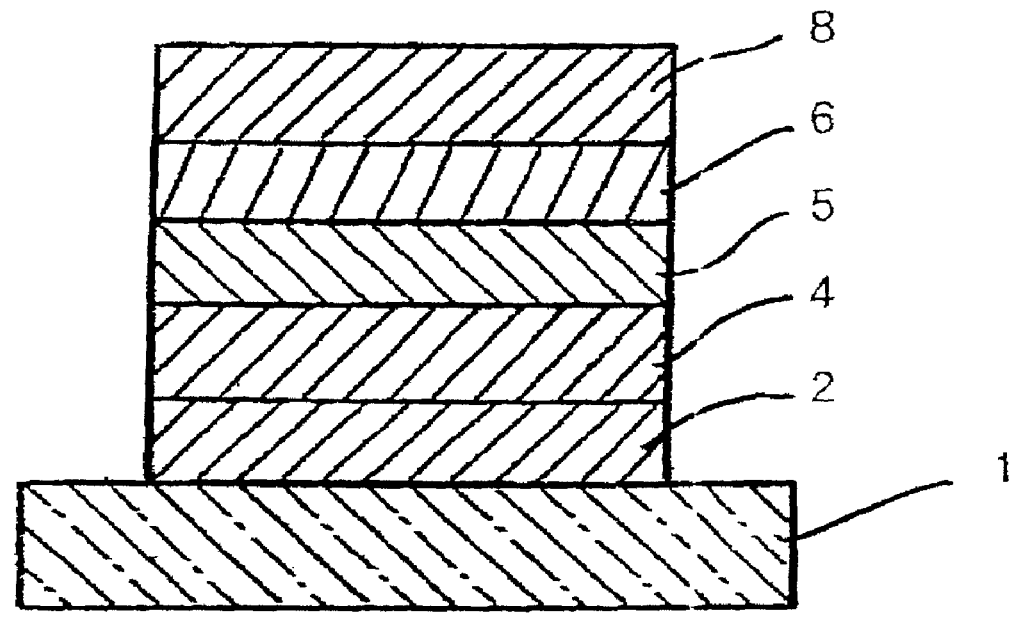
FIG. 1 is a schematic cross-sectional view of an example of the organic electroluminescent device according to the present invention.

Embodiments of organic compounds, charge-transporting materials, and organic electroluminescent devices according to the present invention will now be described in detail, but the below-mentioned description about constituents is only an example (typical example) of the present invention and the scope of the present invention is not limited to the contents within the gist of the present invention.

[Organic Compound]

In the organic compound according to the present invention, one molecule contains two or more partial structures represented by the following Formula (I):

[Compound 10]

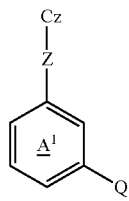

(I)

wherein Cz denotes a carbazolyl group,

Z denotes a direct link or an optional linking group.

Cz, Z, and an $A^1$ ring may have a substituent;

one molecule contains a plurality of Cz's which may be the same or different;

one molecule contains a plurality of Z's which may be the same or different;

one molecule contains a plurality of $A^1$ rings which may be the same or different;

N atoms contained in one molecule do not conjugate with each other excepting between N atoms in the same $B^1$ rings;

one molecule contains only one pyridine ring;

Q denotes a direct link connecting to G present in a moiety represented by the following Formula (II), and one molecule contains a plurality of Q's;

[Compound 11]

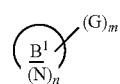

(II)

wherein $B^1$ ring is a six-membered aromatic heterocycle containing n N atoms as a hetero atom;

n is an integer of 1 to 3;

when G is linked to Q, the G denotes a direct link or an optional linking group which links to Q;

when G is not linked to Q, the G denotes an aromatic hydrocarbon group;

G's are bound to C atoms located in ortho-position and para-position with respect to the N atom in $B^1$ ring;

m is an integer of 3 to 5;

one molecule contains a plurality of G's which may be the same or different; and $B^1$ ring may have a substituent in addition to G.

In the organic compound according to the present invention, characteristically, N atoms present in one molecule do not conjugate with each other excepting between N atoms in the same $B^1$ rings. Here, the term "N atoms can conjugate with each other" is equivalent to that N atoms are linked to each other via a partial structure:

[Compound 12]

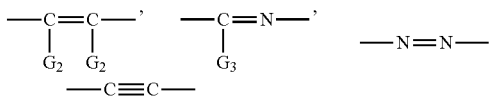

(which may be either cis- or trans-type), or a combination thereof (where $G_1$ to $G_3$ each independently denote a hydrogen atom or an optional substituent, or constitute a part of an aromatic hydrocarbon ring or aromatic heterocycle). In other words, the term "N atoms do not conjugate with each other" in the present invention is equivalent to that N atoms cannot conjugate with each other, namely, N atoms are not linked to each other with the above-mentioned partial structures.

Since N atoms do not conjugate with each other, the organic compound according to the present invention has the following effects:

1) Since an N atom in Cz and an N atom in $B^1$ ring do not conjugate with each other, the Cz group which is an electron-donating group mainly involved in one-electron oxidation and the $B^1$ ring which is an electron-accepting group mainly involved in one-electron reduction exert mutual influence on each other to cause transfer of an electric charge within the molecule, resulting in polarization of the molecule. Consequently, it can be avoided to induce a decrease in the triplet excitation level of the molecule or a decrease in the oxidation/reduction stability.

2) If N atoms of plural $B^1$ rings conjugate with each other in one molecule, hole-accepting properties occur on $B^1$ rings which are inferior in oxidation durability. Therefore, a probability of oxidation degradation cannot be practically neglected. However, since an N atom in $B^1$ ring does not conjugate with an N atom in another $B^1$ ring, such a risk can be avoided. The risk is caused by appearance of. Therefore, a high triplet excitation level can be expected compared to when N atoms of $B^1$ rings conjugate with each other.

3) Since N atoms in Cz do not conjugate with each other, a high triplet excitation level can be expected compared to when N atoms of Cz conjugate with each other.

[1] Structure of a Part Represented by Formula (I)

The part represented by the above-mentioned Formula (I) includes a portion being mainly involved in hole transportation and a portion being mainly involved in electron transportation in such a manner that both parts do not largely interfere with each other.

The portion mainly involved in hole transportation is Cz-Z— in Formula (I), and the portion mainly involved in electron transportation is -Q-G-$B^1$ ring. The portion mainly involved in hole transportation has excellent durability against electrical oxidation. The portion mainly involved in electron transportation has excellent durability against electrical reduction.

The portion mainly involved in hole transportation and the portion mainly involved in electron transportation are in meta-position to each other via a benzene ring. The benzene ring has excellent heat resistance, excellent electrochemical stability, and a high triplet excitation level. Consequently, the organic compound according to the present invention has excellent heat resistance, excellent electrochemical stability, and a high triplet excitation level. Since an m-linking benzene ring includes both electron-accepting property and electron-donating property, the benzene ring receives a part of positive charges according to need when the Cz group is oxidized, and the benzene ring receives a part of negative charges according to need when the $B^1$ ring is reduced. Therefore, the organic compound according to the present invention has excellent electrochemical stability (durability against repeated electrical oxidation/reduction).

One molecule of the organic compound according to the present invention includes two or more partial structures represented by Formula (I), and the hole injection/transportation property is improved thereby. Consequently, it is easy to decrease the element-driving voltage when the compound is used in an organic electroluminescent element and to suitably supply positive and negative charges necessary for inducing recombination of holes and electrons in a light-emitting layer.

[2] Number of a Part Represented by Formula (I)

In the organic compound according to the present invention, the number of the part represented by the above-mentioned Formula (I) is at least two per one molecule, but preferably 4 or low. From the viewpoint of balance of hole-transporting property and electron-transporting property, the number is most preferably 2 or 3.

In the definition that one molecule includes two or more partial structures represented by Formula (I), for example, Q in Formula (I) may be linked to one of plural G's contained in one $B^1$ ring, as shown in the following Formula (A). Compounds represented by the following Formula (A) are included in the definition that one molecule includes two or more partial structures represented by Formula (I).

[Compound 13]

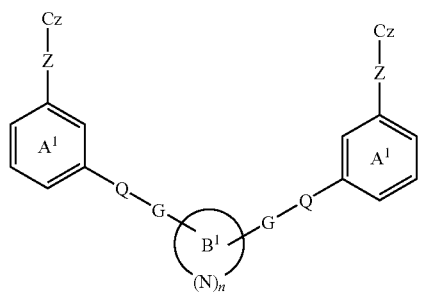

(A)

[3] Constituents in Formula (I)

<$A^1$ Ring>

$A^1$ ring in Formula (I) is a benzene ring which may include an optional substituent in addition to Z and Q.

Further, the plurality of $A^1$ rings present in one molecule of the organic compound according to the present invention may be the same or different.

In the present invention, the term "may include a substituent" means that one or more substituents may be contained.

The substituent other than Z and Q is preferably an alkyl group, aromatic hydrocarbon group, acyl group, alkoxy group, aryloxy group, alkylthio group, arylthio group, alkoxycarbonyl group, aryloxycarbonyl group, halogen atom, arylamino group, alkylamino group, or aromatic heterocyclic group; more preferably an alkyl group, aromatic hydrocarbon group, or aromatic heterocyclic group; and most preferably a monovalent group derived from a 6-membered single ring or from a condensed ring containing 2 to 5 condensed rings, such as a benzene ring, naphthalene ring, anthracene ring, phenanthrene ring, perylene ring, tetracene ring, pyrene ring, benzpyrene ring, crycene ring, triphenylene ring, fluoranthene ring, or carbazole ring; or a monovalent group formed by linking a plurality of such rings (for example, biphenyl group or terphenyl group).

In addition, the substituents of $A^1$ ring may form a condensed ring with the $A^1$ ring by linking the substituents of the $A^1$ ring to each other or by linking a part of Z to the $A^1$ ring. Preferable examples include a condensed ring containing 2 to 5 condensed rings of 6-membered ring, such as a naphthalene ring, an anthracene ring, a phenanthrene ring, a perylene ring, a tetracene ring, a pyrene ring, a benzpyrene ring, a crycene ring, a triphenylene ring, and a fluoranthene ring.

Preferably, $A^1$ ring does not have any substituents other than Z and Q or has a carbazolyl group as a substituent. When $A^1$ ring has a carbazolyl group as a substituent, the carbazolyl group is preferably in the meta-position with respect to Q.

Most preferably, $A^1$ ring does not have any substituents other than Z and Q. This is because of the following reasons:

In a carbazolyl group, for example, $A^1$ ring can have up to five carbazolyl groups including —Z-Cz in total. When a plurality of carbazolyl groups are linked to one aromatic hydrocarbon group, excessive positive charges are concentrated on the aromatic hydrocarbon group or positive charges is highly localized to at least one of N, 1, 3, 6, and 9-positions of the carbazolyl group by electrical oxidation. Thus, the durability against the electrical oxidation is significantly decreased. Therefore, preferably, $A^1$ ring does not have any substituents other than Z and Q, namely, $A^1$ ring has only —Z-Cz as a carbazolyl group.

<Cz>

Cz of Formula (I) denotes a carbazolyl group. Examples of Cz include an N-carbazolyl group, a 1-carbazolyl group, a 2-carbazolyl group, a 3-carbazolyl group, and a 4-carbazolyl group. A plurality of Cz's present in one molecule may be the same or different.

From the viewpoints of a high triplet excitation level and excellent electrochemical stability, Cz is preferably an N-carbazolyl group or 2-carbazolyl group, most preferably an N-carbazolyl group.

The Formula (I) when Cz of Formula (I) is an N-carbazolyl group is shown by the following Formula (I-1):

[Compound 14]

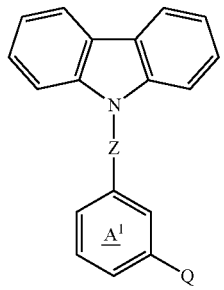

(I-1)

This Cz may have an optional substituent.

The substituent is preferably an alkyl group, aromatic hydrocarbon group, acyl group, alkoxy group, aryloxy group, alkylthio group, arylthio group, alkoxycarbonyl group, aryloxycarbonyl group, halogen atom, arylamino group, alkylamino group, or aromatic heterocyclic group; more preferably an alkyl group, aromatic hydrocarbon group, or aromatic heterocyclic group. From the viewpoint of a high triplet excitation level and from the viewpoint of avoiding a decrease in electric durability due to biased electric charge distribution, the substituent is preferably a monovalent group derived from a 6-membered single ring or from a condensed ring containing 2 to 5 condensed rings, such as a benzene ring, naphthalene ring, anthracene ring, phenanthrene ring, perylene ring, tetracene ring, pyrene ring, benzpyrene ring, crycene ring, triphenylene ring, or fluoranthene ring; or a monovalent group formed by linking a plurality of such rings (for example, biphenyl group or terphenyl group).

When Cz has a substituent, the substituent at 3-position or 6-position of Cz is preferably a group other than that which may decrease the triplet excitation level, such as a benzene group.

The substituent of Cz preferably has a molecular weight of 500 or less in total, more preferably 250 or less. Most preferably, Cz does not have substituents.

<Z>

Z in Formula (I) denotes a direct link or an optional linking group.

The optional linking group is preferably a divalent linking group derived from a 6-membered single ring or from a condensed ring containing 2 to 5 condensed rings, such as a benzene ring, naphthalene ring, anthracene ring, phenanthrene ring, perylene ring, tetracene ring, pyrene ring, benzpyrene ring, crycene ring, triphenylene ring, or fluoranthene ring; or a divalent linking group formed by linking a plurality of such rings (for example, biphenyl group and terphenyl group). Z is preferably a direct link or a divalent linking group formed by linking 1 to 8 benzene groups such as phenylene group, biphenyl group, or terphenylene group.

When Z denotes an optional linking group, Z may have an optional substituent. The substituent is preferably an alkyl group, aromatic hydrocarbon group, acyl group, alkoxy group, aryloxy group, alkylthio group, arylthio group, alkoxycarbonyl group, aryloxycarbonyl group, halogen atom, arylamino group, alkylamino group, or aromatic heterocyclic group; more preferably an alkyl group, aromatic hydrocarbon group, or aromatic heterocyclic group; most preferably a monovalent group derived from a 6-membered single ring or from a condensed ring containing 2 to 5 condensed rings, such as a benzene ring, naphthalene ring, anthracene ring, phenanthrene ring, perylene ring, tetracene ring, pyrene ring, benzpyrene ring, crycene ring, triphenylene ring, or fluoranthene ring; or a monovalent group formed by linking a plurality of such rings (for example, biphenyl group and terphenyl group).

Z preferably has a molecular weight of 1000 or less, more preferably 500 or less.

In particular, Z is preferably a direct link or -(Ph)$_p$-. Here, Ph denotes a phenylene group which may have a substituent. In addition, p is an integer of 1 to 8, preferably an integer of 1 or 2.

Most preferably, Z is a direct link.

<Example of Formula (I)>

Examples of the partial structure represented by Formula (I) excluding a part represented by Formula (II) are shown below, but the present invention is not limited to them.

[Compound 15]

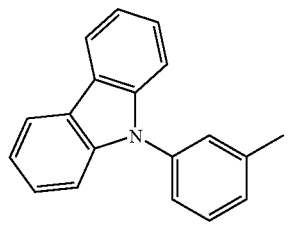

V-1

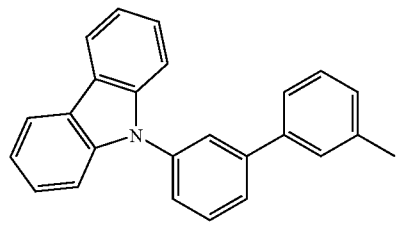

V-2

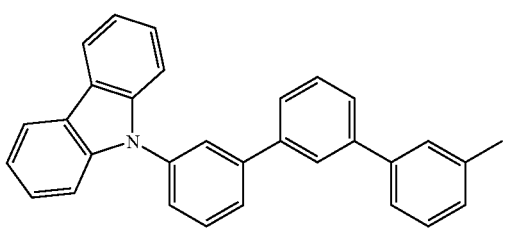

V-3

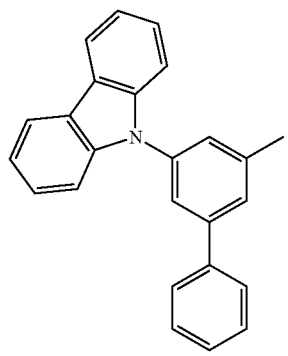

V-4

-continued
V-5
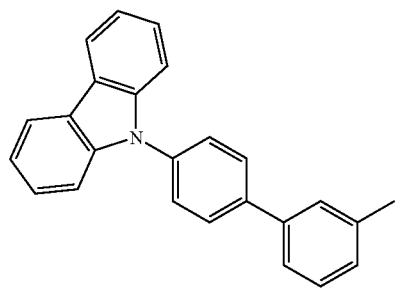
V-6
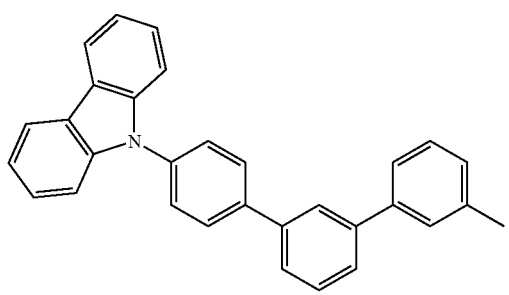
V-7
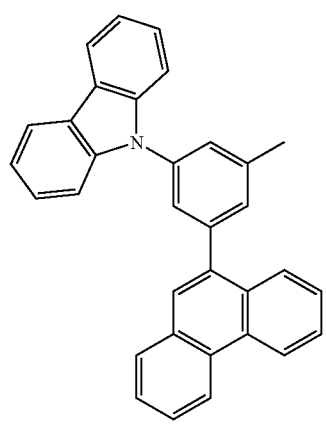
V-8
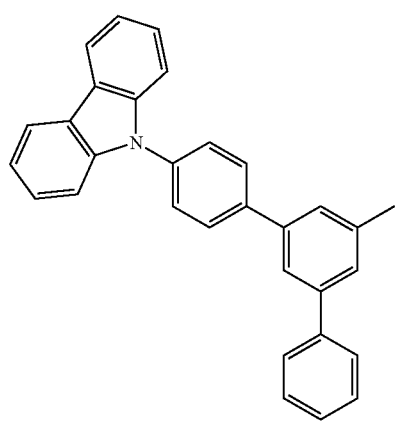
V-9
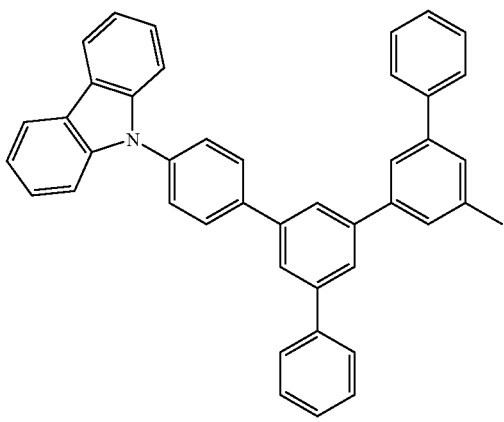
V-10
V-11
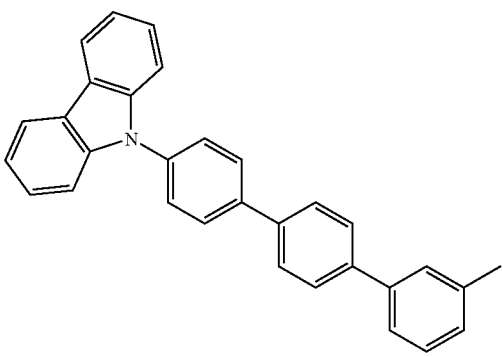
V-12

V-13
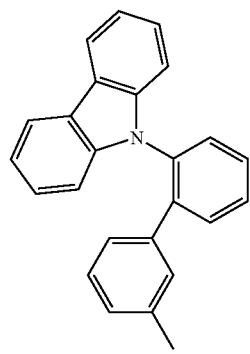
V-17
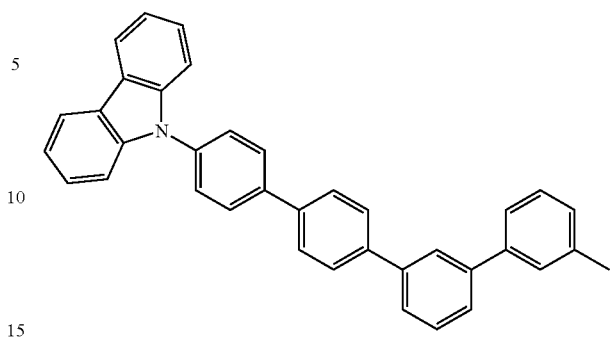
V-14
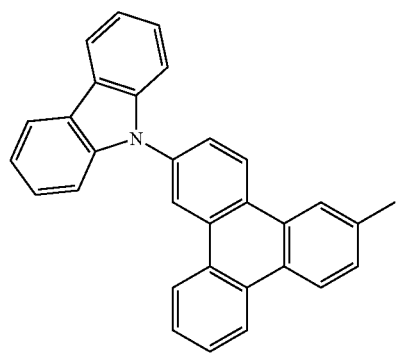
V-15
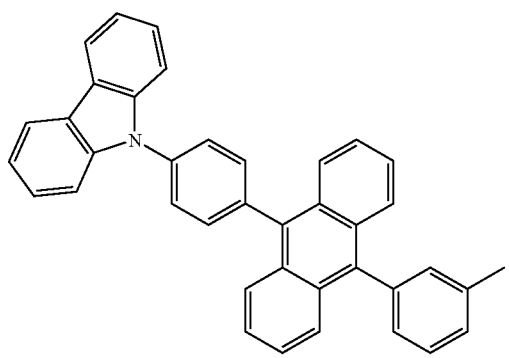
[Compound 16]
V-16
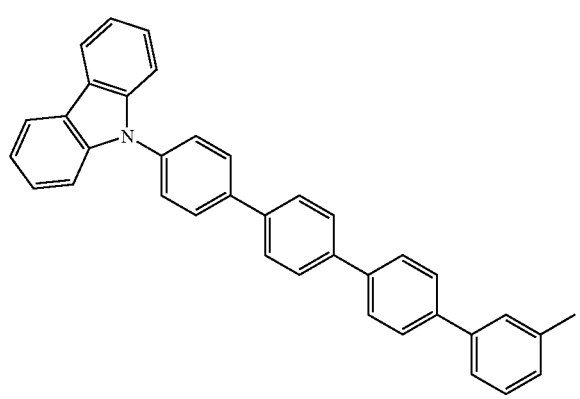
V-18
V-19
V-20
V-21
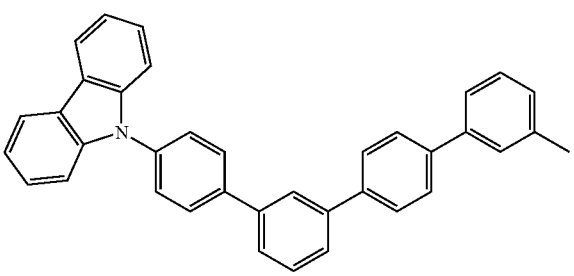

V-22
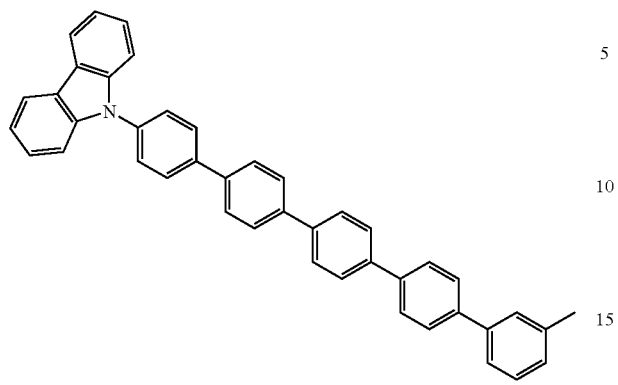
[Compound 17]
V-23
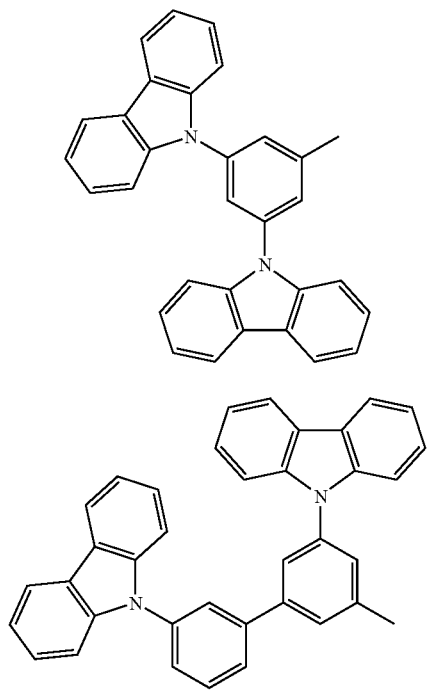
V-24
V-25
V-26
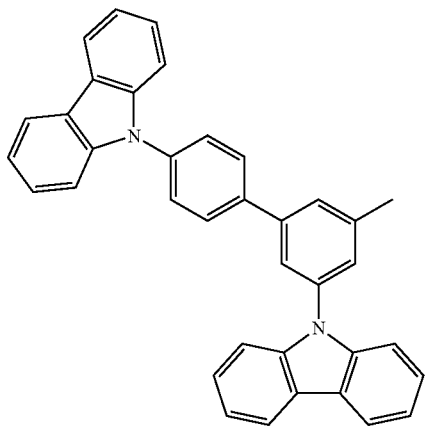
V-27
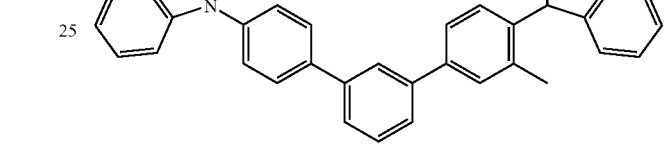
V-28
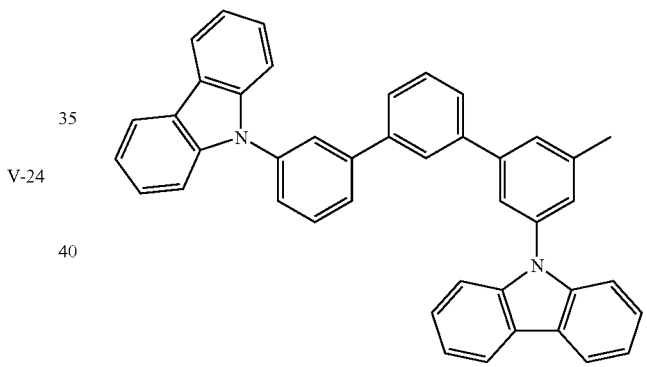
[Compound 18]
V-29
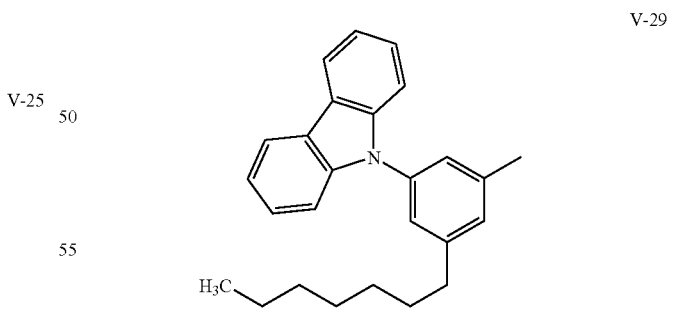
V-30
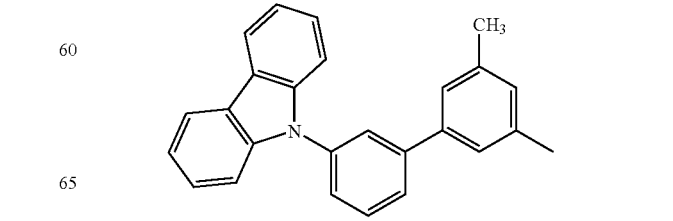

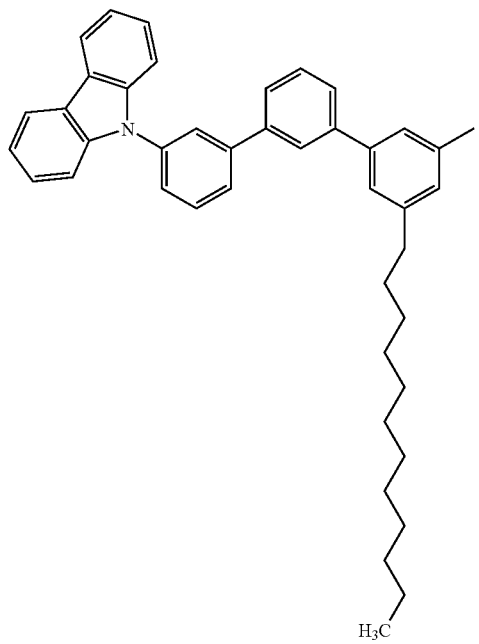
V-31
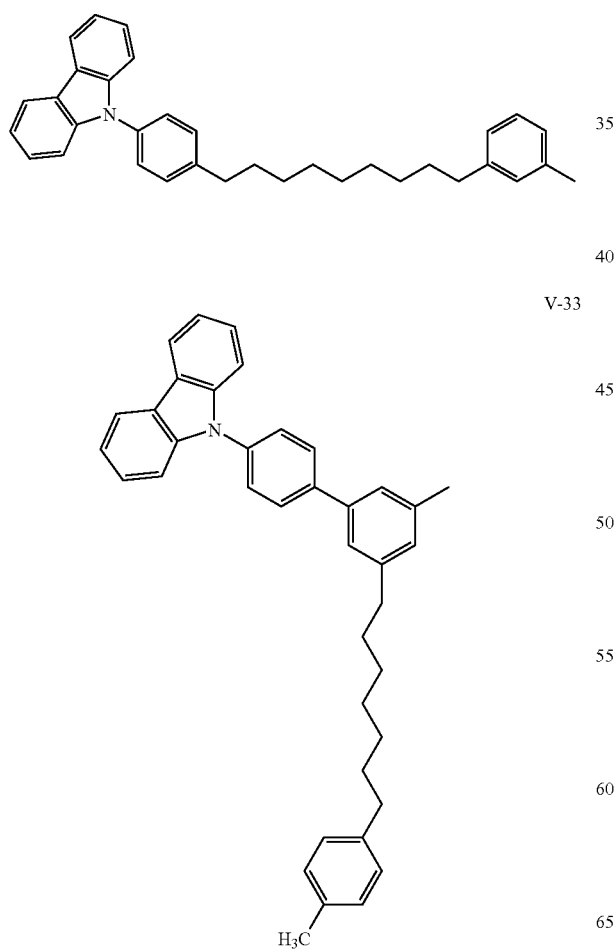
V-32
V-33
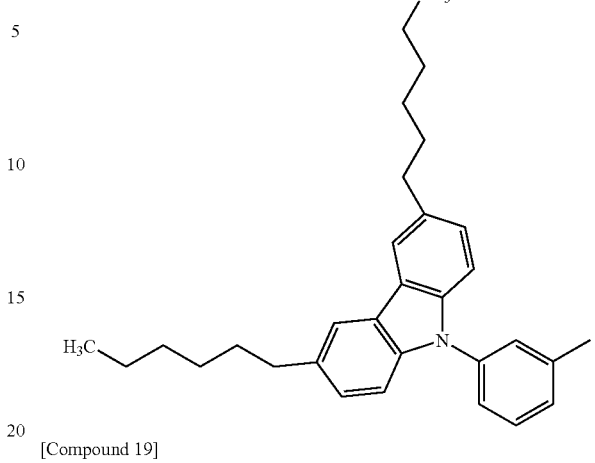
V-34
[Compound 19]
V-35
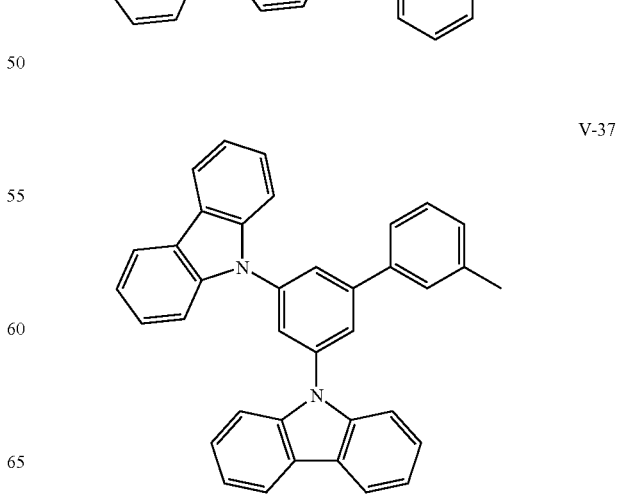
V-36
V-37

V-38

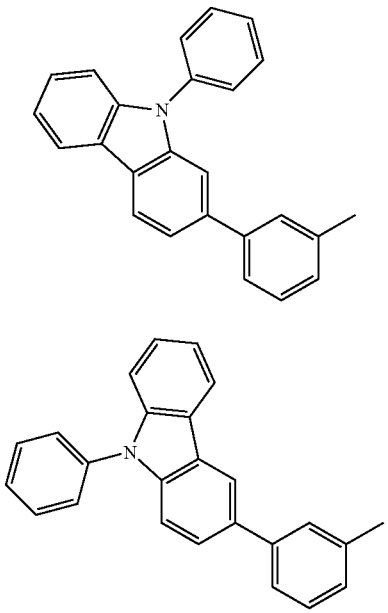

V-39

Among the examples shown above, particularly, V-1 to 6, 8, 9, 12, 13, 16 to 22, 24, 27, 28, and 35 to 37 are more preferable, V-1, 2, 3, 5, 6, and 12 are most preferable.

<Q>

Q denotes a direct link which is connected to at least one G of the following Formula (II).

[Compound 20]

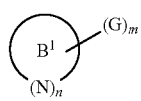
(II)

The part represented by Formula (II) preferably has a molecular weight of 70 or more, more preferably 75 or more and preferably 1000 or less, more preferably 500 or less. When the molecular weight is lower than this lower limit, the aromatic property may be undesirably deteriorated. When the molecular weight is higher than the upper limit, it may increase the evaporation temperature to make film-forming by a vacuum deposition method difficult or may decrease the solubility to make film-forming by a wet method difficult.

In Formula (II), $B^1$ ring is a 6-membered aromatic heterocycle containing n N atoms as a hetero atom, wherein n is an integer of 1 to 3. When one molecule of the organic compound according to the present invention has a plurality of $B^1$ rings, the $B^1$ rings may be the same or different.

Preferably, Formula (II) is specifically represented by the following Formulae (II-1) to (II-4):

[Compound 21]

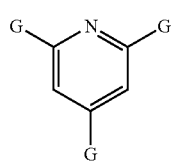
(II-1)

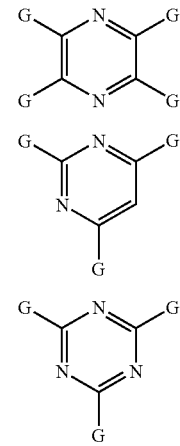

A group represented by Formula (II), in particular, by any one of Formulae (II-1) to (II-4) is mainly involved in electron transportation in the organic compound according to the present invention. The group characteristically has excellent durability against electrical reduction.

The number of the group represented by any one of Formulae (II-1) to (II-4) contained in one molecule may be 1 to 8 as long as they are not conjugated with each other in the molecule. Generally, the electron-transporting property, namely, a purpose, can be sufficiently achieved if one group is present in one molecule. Therefore, the number of the groups in one molecule is preferably one, with the view of balance of hole-transporting property and electron-transporting property, heat resistance and vaporization property required for depositing a film, solubility required for wet film-forming, stability in the air (oxidation resistance), or ease of highly purifying the compound.

Groups represented by each Formula will now be described individually.

Group Represented by Formula (II-1)

A pyridine ring represented by Formula (II-1) can be provided with durability against electrical reduction by being substituted at 2-, 4-, and 6-positions thereof.

In addition, each of 3- and 5-positions of the pyridine ring may have a substituent. The substituent is preferably an aryl group such a phenyl group, heteroaryl group such as a pyridyl group, or an alkyl group such as a methyl group. However, from the viewpoint of excellent electrochemical stability, most preferably, the 3- and 5-positions are not substituted.

Group Represented by FORMULA (II-2)

A pyrazine ring represented by Formula (II-2) can be provided with durability against electrical reduction by being substituted at 2-, 3-, 5-, and 6-positions thereof.

Group Represented by Formula (II-3)

A pyrimidine ring represented by Formula (II-3) can be provided with durability against electrical reduction by being substituted at 2-, 4-, and 6-positions thereof.

In addition, 5-position of the pyrimidine ring may have a substituent. The substituent is preferably an aryl group such a phenyl group, heteroaryl group such as a pyridyl group, or an alkyl group such as a methyl group. However, from the viewpoint of excellent electrochemical stability, most preferably, the 5-position is not substituted.

Group Represented by Formula (II-4)

A triazine group represented by Formula (II-4) can be provided with durability against electrical reduction by being substituted at 2-, 4-, and 6-positions thereof.

As $B^1$ ring, from the viewpoints of a high triplet excitation level and excellent electrochemical stability, a pyridine ring represented by the above-mentioned Formula (II-1), namely, n is most preferably 1.

In Formula (II), G denotes a direct link or an optional linking group which is linked to Q or denotes an aromatic hydrocarbon group. Further, G is linked to a C atom in an ortho-position or para-position with respect to an N atom of $B^1$ ring. In addition, m is an integer of 3 to 5. One molecule includes a plurality of G's which may be the same or different.

When G is a direct link or an optional linking group which is linked to Q, the G is preferably a direct link; a divalent linking group derived from a 6-membered single ring or from a condensed ring containing 2 to 5 condensed rings, such as a benzene ring, naphthalene ring, anthracene ring, phenanthrene ring, perylene ring, tetracene ring, pyrene ring, benzpyrene ring, crycene ring, triphenylene ring, or fluoranthene ring; or a divalent linking group formed by linking a plurality of such rings (for example, biphenyl group and terphenyl group). More preferably, G is a direct link or a divalent linking group formed by linking 1 to 8 benzene rings represented by -(Ph)$_p$—(Ph denotes a phenylene group which may have a substituent, and p is an integer of 1 to 8), such as a phenylene group, biphenylene group, or terphenylene group.

The molecular weight of G when G is linked to Q is preferably 1000 or less, more preferably 500 or less. When the molecular weight is higher than this upper limit, the aromatic property may be undesirably deteriorated. In addition, disadvantageously, the evaporation temperature may be decreased to make film-forming by a vacuum deposition method difficult or the solubility may be decreased to make film-forming by a wet method difficult, when the molecular weight is higher than the upper limit.

When G is not linked to Q, G denotes an aromatic hydrocarbon group. G not linking to Q is not specifically limited as long as the G is an aromatic hydrocarbon group, but is preferably a monovalent group derived from a 6-membered single ring or from a condensed ring containing 2 to 5 condensed rings, such as a benzene ring, naphthalene ring, anthracene ring, phenanthrene ring, perylene ring, tetracene ring, pyrene ring, benzpyrene ring, crycene ring, triphenylene ring, or fluoranthene ring; or a monovalent group formed by linking a plurality of such rings (for example, biphenyl group or terphenyl group), and more preferably, a monovalent group formed by linking 1 to 8 benzene rings, such as a phenyl group, biphenyl group, or terphenyl group.

The molecular weight of G when G is not linked to Q is preferably 2000 or less, more preferably 1000 or less. When the molecular weight is higher than this upper limit, the aromatic property may be undesirably deteriorated. In addition, disadvantageously, the evaporation temperature may be decreased to make film-forming by a vacuum deposition method difficult or the solubility may be decreased to make film-forming by a wet method difficult, when the molecular weight is higher than the upper limit.

G may have an optional substituent. The substituent is preferably an alkyl group, aromatic hydrocarbon group, acyl group, alkoxy group, aryloxy group, alkylthio group, arylthio group, alkoxycarbonyl group, aryloxycarbonyl group, halogen atom, arylamino group, alkylamino group, or aromatic heterocyclic group; more preferably an alkyl group, aromatic hydrocarbon group, or aromatic heterocyclic group. Most preferably, G does not have any substituents or has a substituent of a monovalent group derived from a 6-membered single ring or from a condensed ring containing 2 to 5 condensed rings, such as a benzene ring, naphthalene ring, anthracene ring, phenanthrene ring, perylene ring, tetracene ring, pyrene ring, benzpyrene ring, crycene ring, triphenylene ring, or fluoranthene ring; or a monovalent group formed by linking a plurality of such rings (for example, biphenyl group or terphenyl group).

[4] Molecular Weight

The molecular weight of the organic compound according to the present invention is generally 4000 or less, preferably 3000 or less, and more preferably 2000 or less. The molecular weight is generally 200 or more, preferably 300 or more, and more preferably 400 or more.

When the molecular weight of the organic compound according to the present invention is higher than this upper limit, the sublimation property may be significantly decreased to induce disadvantages when a vacuum deposition method is used for preparing an electroluminescent element or the molecular weights of impurities may be increased to make purification difficult. In addition, when the molecular weight is lower than the lower limit, the glass-transition temperature, melting point, and vaporization temperature are decreased. Consequently, the heat resistance may be significantly deteriorated.

[5] Physical Properties

The organic compound according to the present invention generally has a glass-transition temperature of 50° C. or more. When the organic compound is used in an organic electroluminescent element, from the viewpoint of heat resistance, the glass-transition temperature is preferably 90° C. or more, more preferably 110° C. or more. The upper limit of the glass-transition temperature is generally about 400° C.

The organic compound according to the present invention generally has a vaporization temperature of 800° C. or less at atmospheric pressure. When the organic compound is used in an organic electroluminescent element, from the viewpoint of stability of a film deposition process, the vaporization temperature is preferably 700° C. or less, more preferably 600° C. or more. The lower limit of the vaporization temperature is generally about 300° C.

The organic compound according to the present invention generally has a melting point of 100° C. or more. When the organic compound is used in an organic electroluminescent element, from the viewpoint of heat resistance, the melting point is preferably 150° C. or more, more preferably 200° C. or more. The upper limit of the melting point is generally about 500° C.

[6] Preferable Structure

Particularly preferably, the organic compound according to the present invention which has two or more partial structures represented by the above-mentioned Formula (I) in one molecule has a structure represented by the following Formula (III) from the viewpoints of a high triplet excitation level and excellent electrochemical stability.

[Compound 22]    (III)

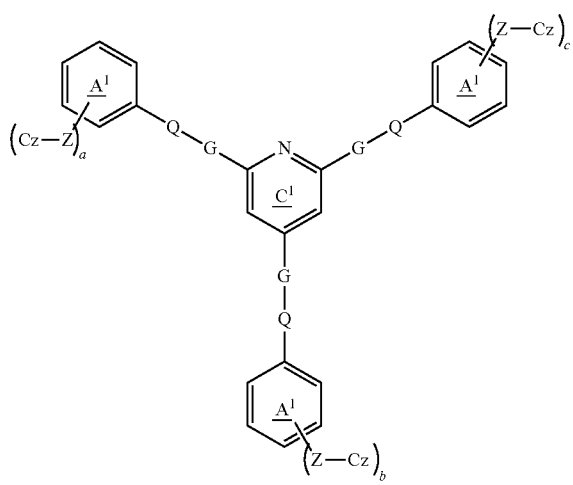

In the Formula, the definitions of Cz, Z, A¹ ring, and Q are the same as those in Formula (I), and the definition of G is the same as that in Formula (II).

a, b, and c each represent the number of Z-Cz.

In addition, a, b, and c are each independently an integer of 0 to 5.

Further, a+b+c is an integer not less than 2.

Further, the 3-position and/or 5-position of C¹ ring may be substituted with an optional substituent.

In Formula (III), at least two of (Z-Cz)s are in meta-positions with respect to Q in A¹ ring.

In Formula (III), G is preferably -(Ph)$_p$- (where Ph denotes a phenylene group which may have a substituent, and p is an integer of 1 to 8).

Preferably, a and c are each independently 1, 2, or 4, more preferably 1 or 2, and most preferably 1. That is, the resistance to electrical reduction of C¹ ring may be decreased by introducing electron-donating groups such as Cz's in large numbers. Therefore, the smaller numbers of a and c are preferable.

When a molecule is charged with positive or negative charges, deterioration phenomenon caused by the localization of the electric charges can be more suppressed when the molecule has high symmetric property. Therefore, it is preferably that a=c, consequently, it is most preferable that a=c=1.

Preferably, b is 0, 1, 2, or 4, more preferably 0, 1, or 2, and most preferably 0 or 1. That is, the durability against electrical reduction of C¹ ring may be decreased by introducing electron-donating groups such as Cz's in large numbers. Therefore, the smaller number of c is preferable.

Among the organic compounds represented by the above-mentioned Formula (III), an organic compound further represented by the following Formula (IV) has a structure of enhancing durability against electrical reduction and therefore is preferable.

[Compound 23]    (IV)

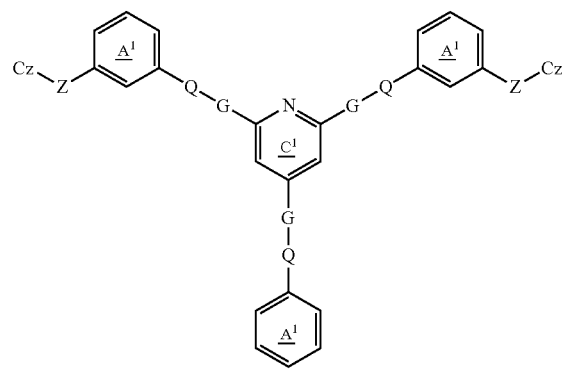

In the Formula, the definitions of Cz, Z, Q, and A¹ ring are the same as those in Formula (I), and the definition of G is the same as that in Formula (II). The definition of C¹ ring is the same as that in Formula (III).

Above all, specifically, an organic compound represented by the following Formula (IV-1) has a preferable structure.

[Compound 24]

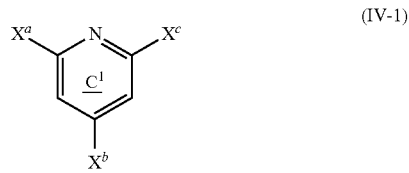

(IV-1)

In the Formula, $X^a$ and $X^c$ are each independently a monovalent group selected from the above-mentioned V-1 to 39, and $X^b$ is a monovalent group selected from the following W-1 to 37. C¹ ring is the same as that in Formula (III).

In the above-mentioned Formula (IV-1), from the viewpoint of the improvement in durability against electrical oxidation/reduction, from the viewpoint of the improvement in amorphous property, or from the viewpoint of the improvement in heat resistance, preferably, $X^a$ and $X^c$ are each independently any one of V-1 to 6, 8, 9, 12, 13, 16 to 22, 24, 27, 28, and 35 to 37; more preferably any one of V-1, 2, 3, 5, 6, 12, and 35 to 37; and most preferably any one of V-1, 2, and 5. In addition, $X^b$ is preferably any one of W-1 to 3, 6, 8, 10, 11, 20, 29, 31, 32, and 34 to 37; more preferably W-1 to 3, 6, 8, 11, 31, 32, and 34 to 36; and most preferably any one of W-2, 6, 34, and 36, from the viewpoint of the improvement in durability against electrical oxidation/reduction.

[Compound 25]

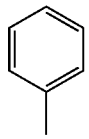

W-1

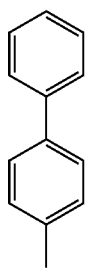

W-2

W-3
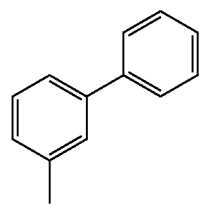
W-4
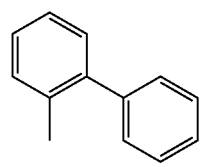
W-5
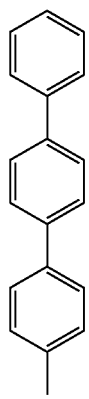
W-6
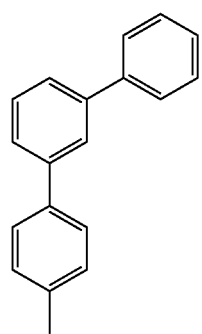
W-7
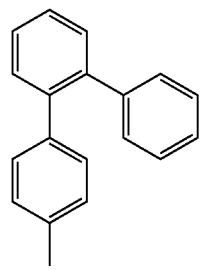
W-8
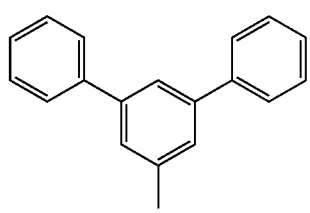
W-9
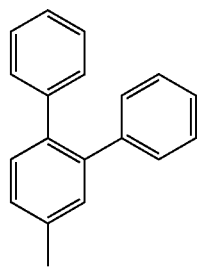
W-10
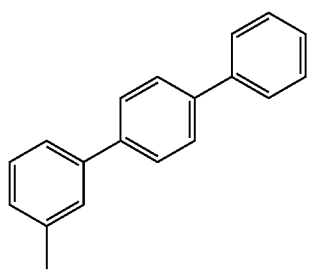
W-11
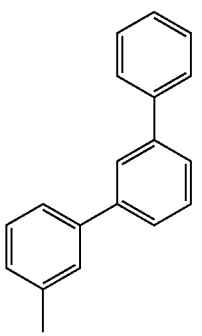
W-12
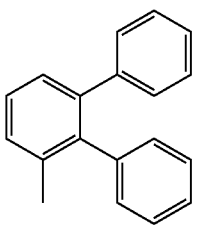
W-13
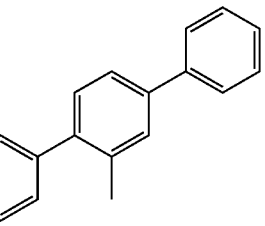
W-14
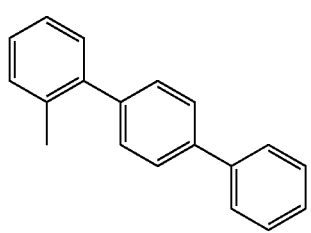

-continued
W-15
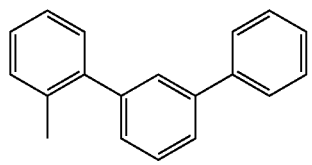
W-16
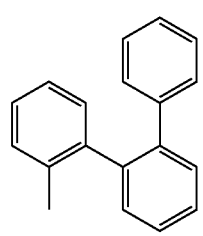
W-17
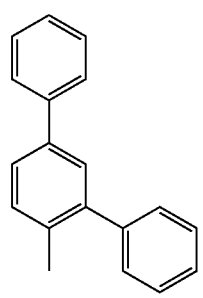
W-18
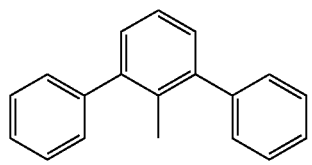
[Compound 26]
W-19
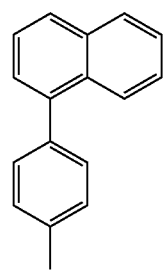
W-20
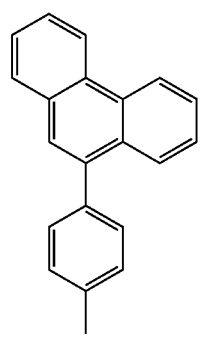
-continued
W-21
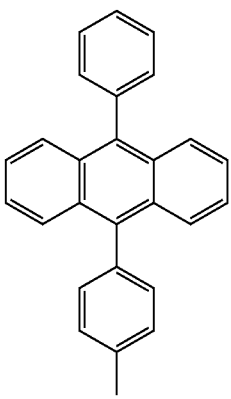
W-22
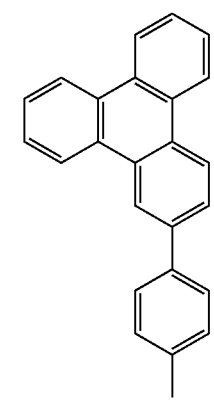
W-23
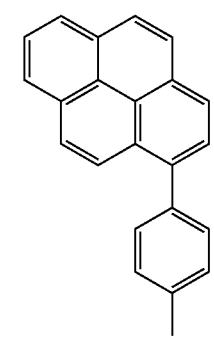
W-24
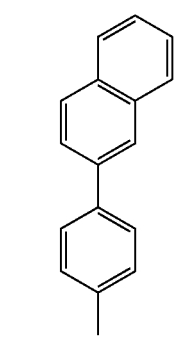

W-25 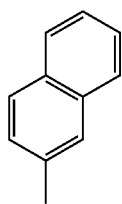
W-26 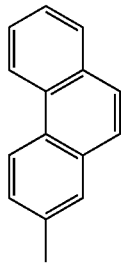
W-27 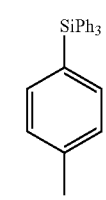
W-28 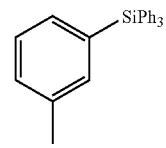
W-29 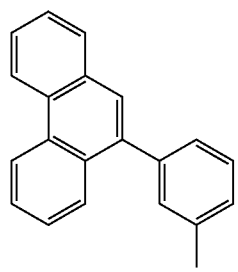
W-30 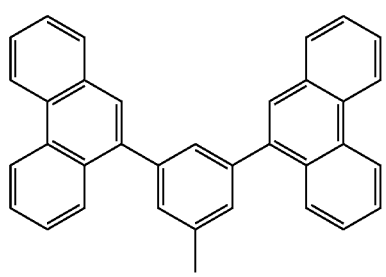
W-31 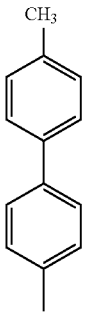
W-32 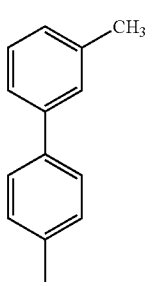
W-33 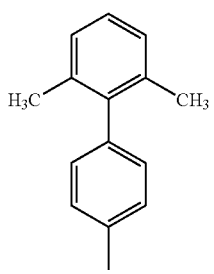
W-34 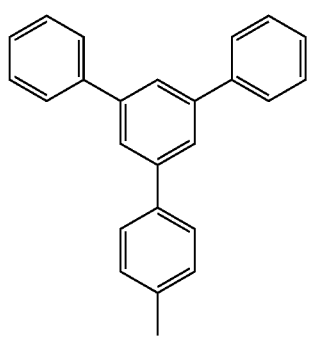
W-35 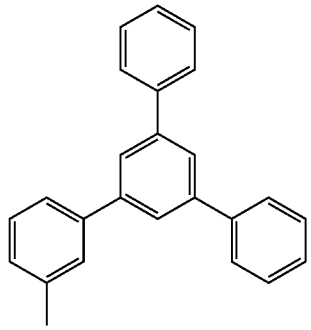

-continued

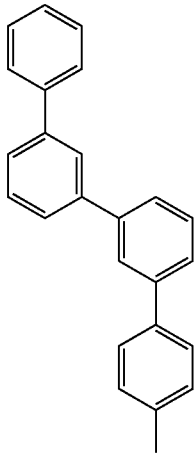
W-36

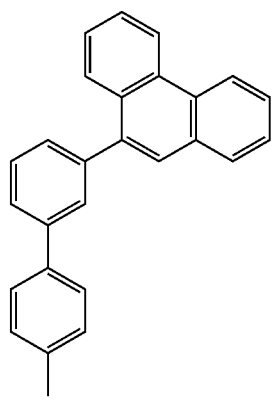
W-37

Another preferably specific structure of the organic compound according to the present invention is represented by the following Formula (V).

[Compound 27]

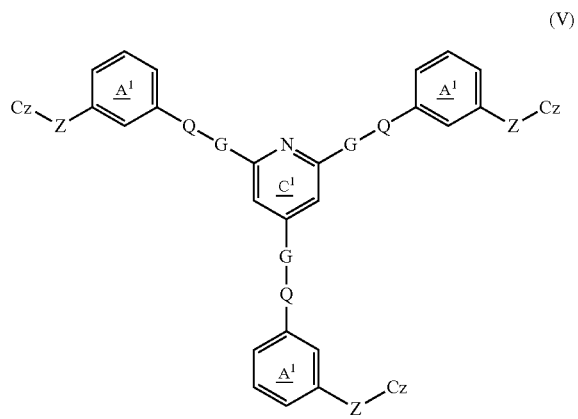
(V)

In the Formula, the definitions of Cz, Z, Q, and $A^1$ ring are the same as those in Formula (I), and the definition of G is the same as that in Formula (II). The definition of $C^1$ ring is the same as that in Formula (III).

Above all, specifically, the structure of an organic compound represented by the following Formula (V-1) or (V-2) is preferable.

[Compound 28]

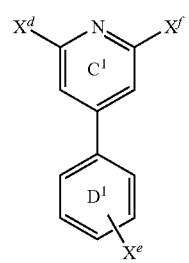
(V-1)

In the Formula, $X^d$, $X^e$, and $X^f$ are each independently a monovalent group selected from the above-mentioned V-1 to 39, and the definition of $C^1$ ring is the same as that in Formula (III). $D^1$ ring is a phenylene linking group which linking $C^1$ ring and $X^e$.

In the above-mentioned Formula (V-1), from the viewpoint of the improvement in durability against electrical oxidation/reduction, the improvement in amorphous property, or the improvement in heat resistance, preferably, $X^d$, $X^e$, and $X^f$ are each independently any one of V-1 to 6, 8, 9, 12, 13, 16 to 22, 24, 27, 28, and 35 to 37; more preferably any one of V-1, 2, 3, 5, 6, 12, and 35 to 37; and most preferably any one of V-1, 2, and 5. When 1-position of $D^1$ ring is defined to the position linking to $C^1$ ring, $X^e$ may be linked to any position of 2 to 6-positions of $D^1$ ring. However, from the viewpoint of the improvement in durability against electrical reduction, $X^e$ is preferably linked to any position of 3 to 5-positions, more preferably to 4-position.

[Compound 29]

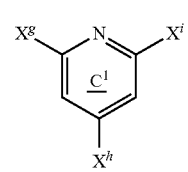
(V-2)

In the Formula, $X^g$, $X^h$, and $X^i$ are each independently a monovalent group selected from the above-mentioned V-1 to 39, and the definition of $C^1$ ring is the same as that in Formula (III).

In the above-mentioned Formula (V-2), from the viewpoint of the improvement in durability against electrical oxidation/reduction, the improvement in amorphous property, or the improvement in heat resistance, preferably, $X^g$, $X^h$, and $X^i$ are each independently any one of V-1 to 6, 8, 9, 12, 13, 16 to 22, 24, 27, 28, and 35 to 37; more preferably any one of V-1, 2, 3, 5, 6, 12, and 35 to 37; and most preferably any one of V-1, 2, and 5.

[7] Illustrative Embodiment

Preferable specific examples of the organic compound according to the present invention will now be described, but the present invention is not limited to them. Here, in the structural formulae shown below, —N-Cz denotes an N-carbazolyl group.
[Compound 30]
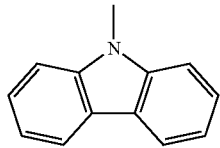
[Compound 31]
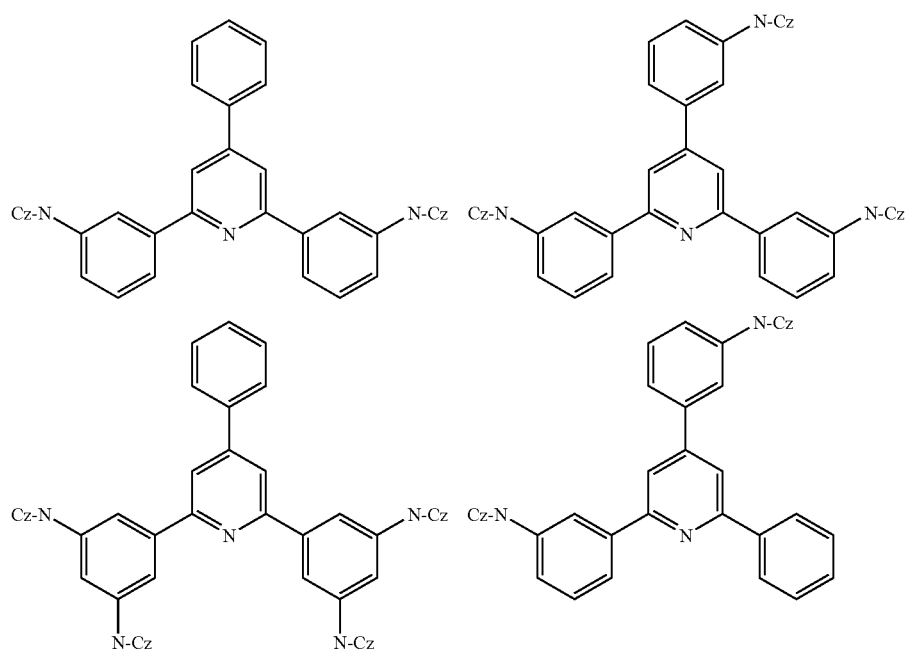
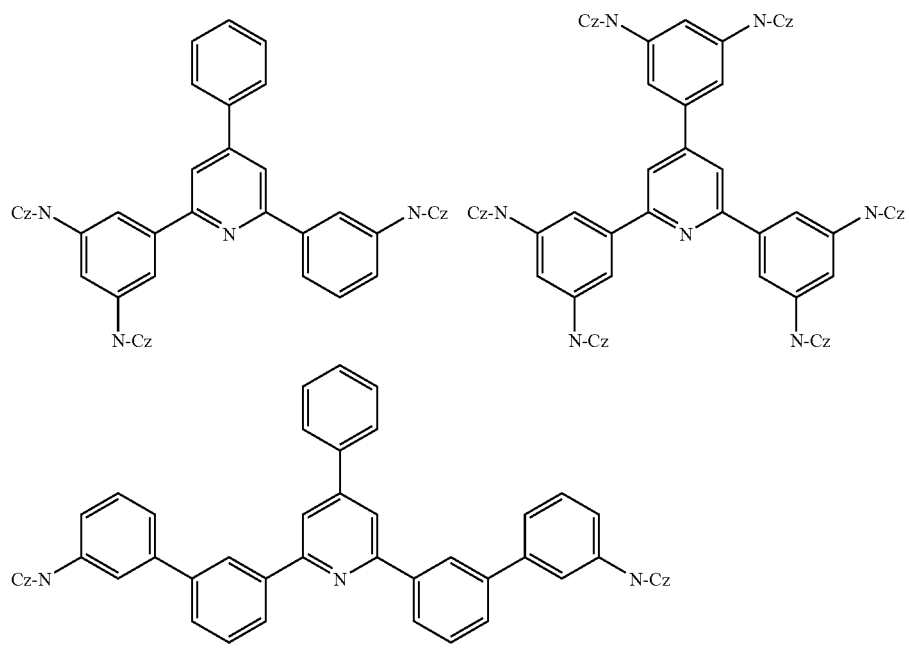

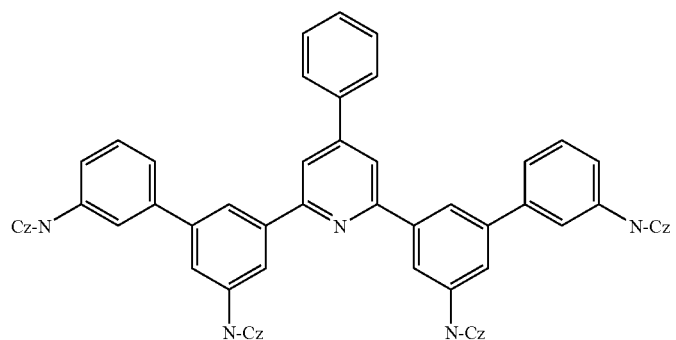
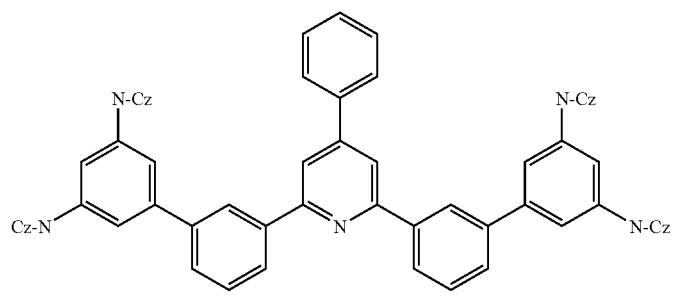
[Compound 32]
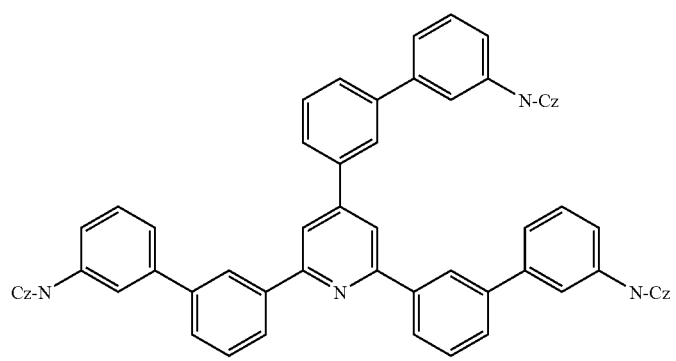
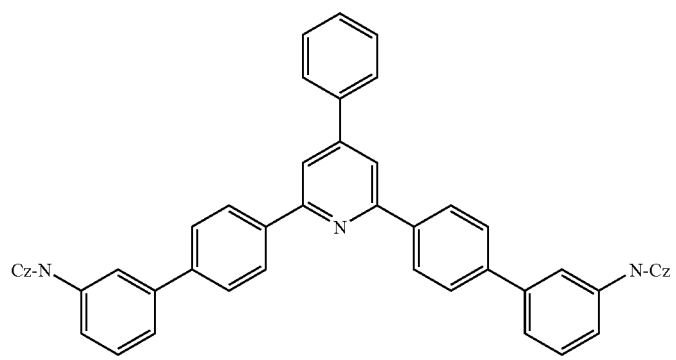
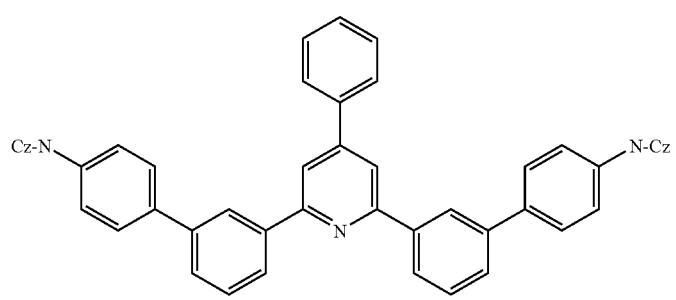

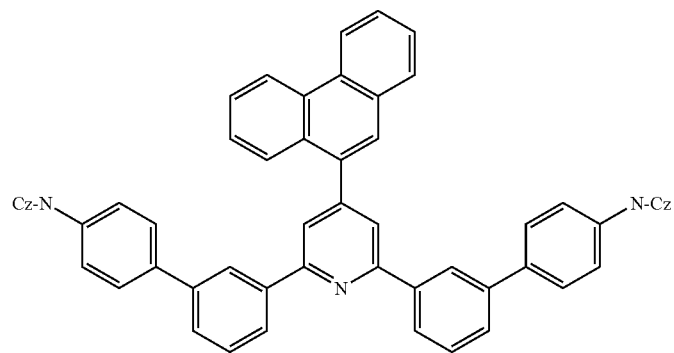
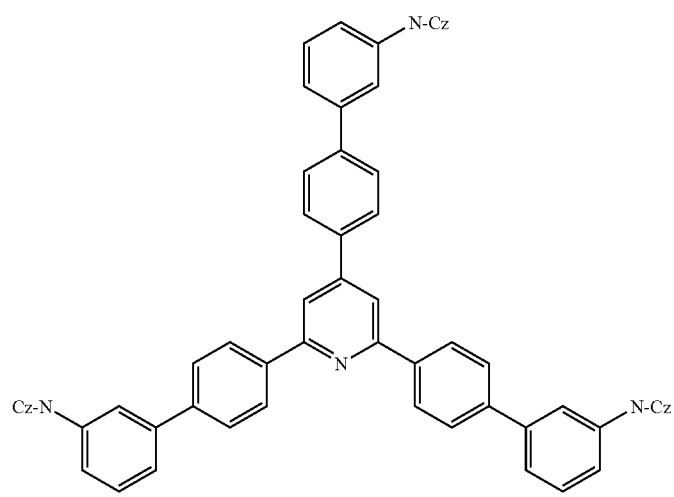
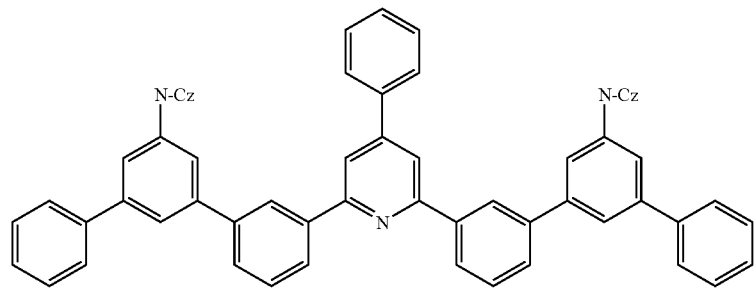
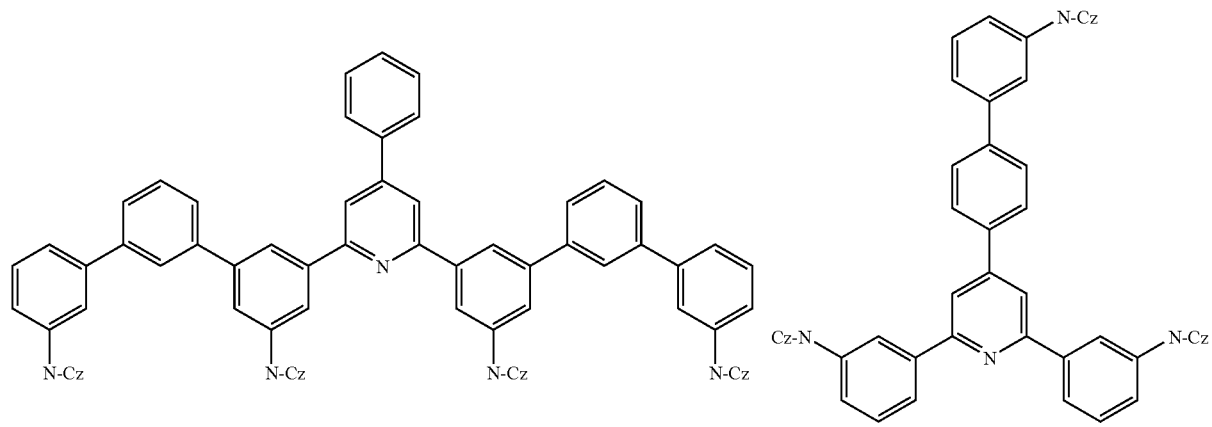

-continued
[Compound 33]
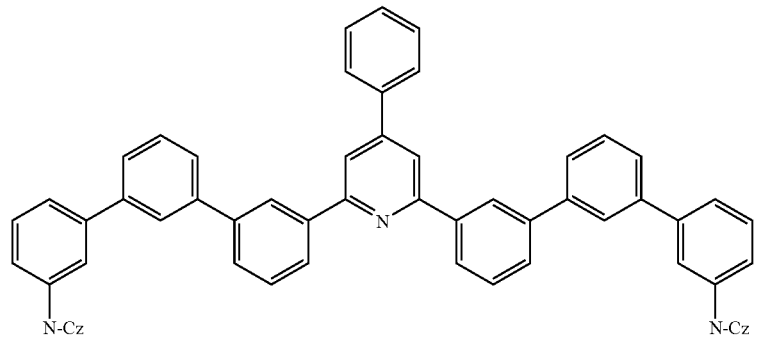
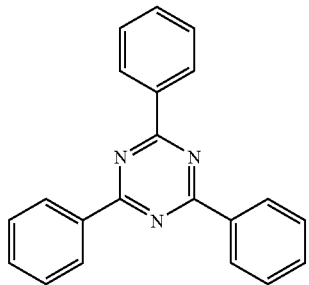
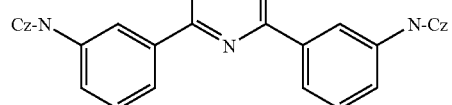
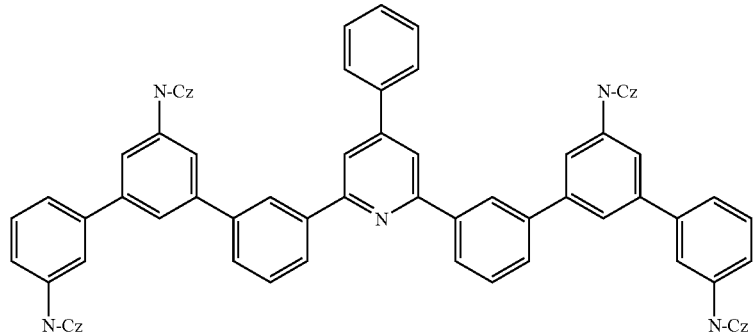
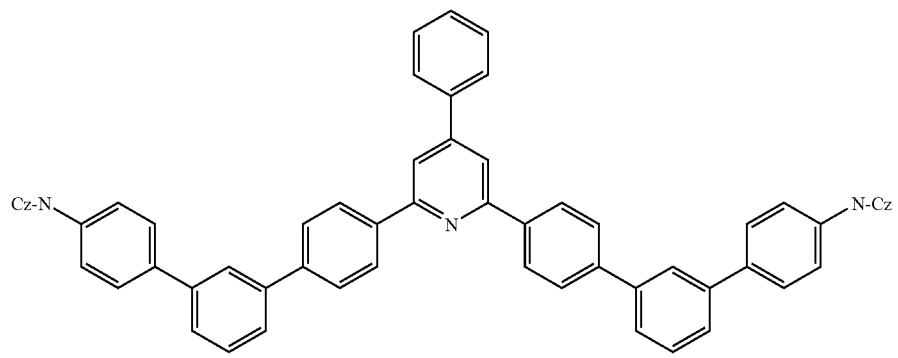

-continued
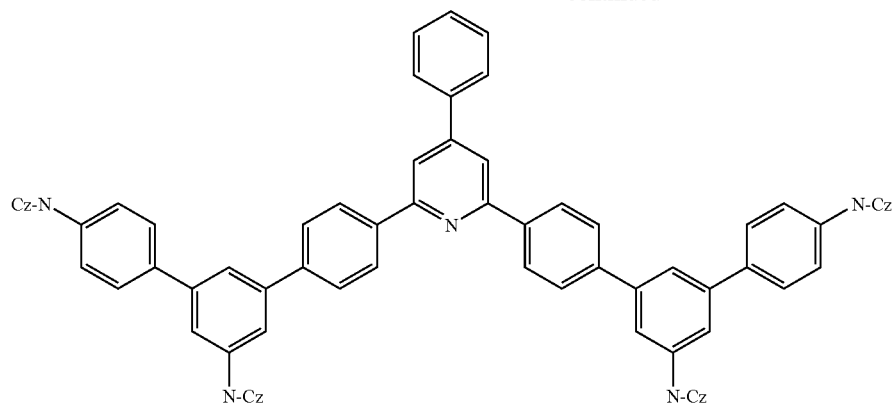
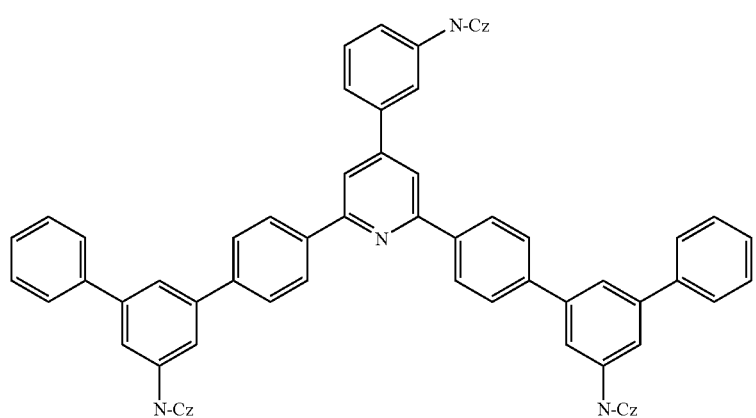
[Compound 34]
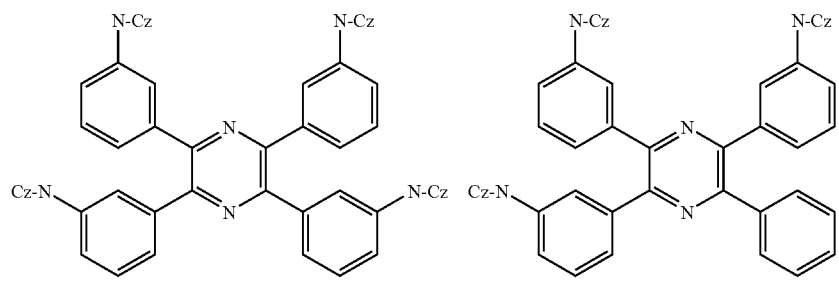
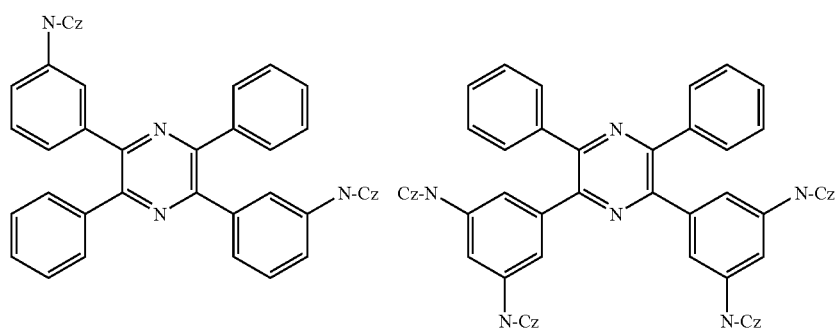

-continued
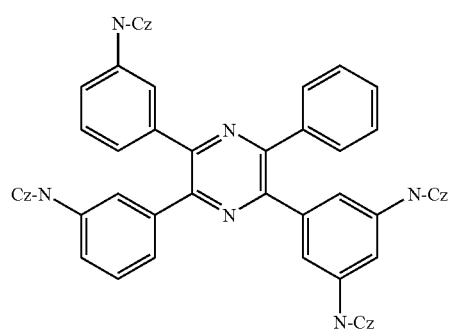
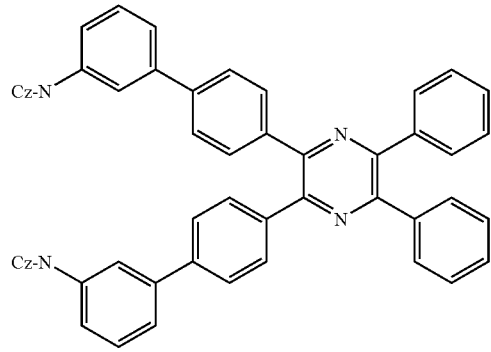
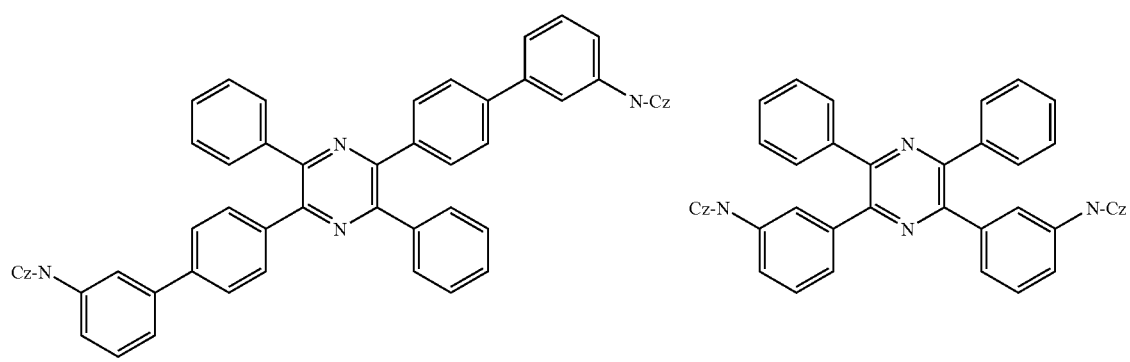
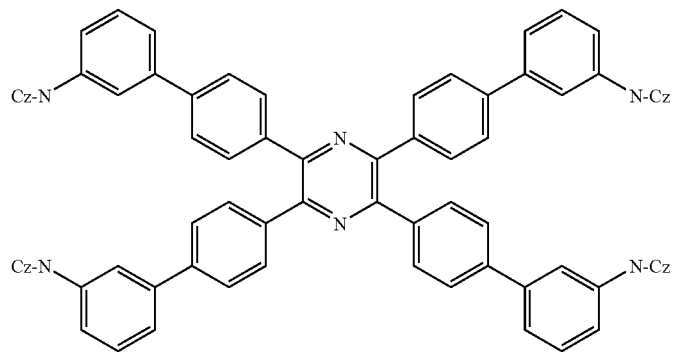
[Compound 35]
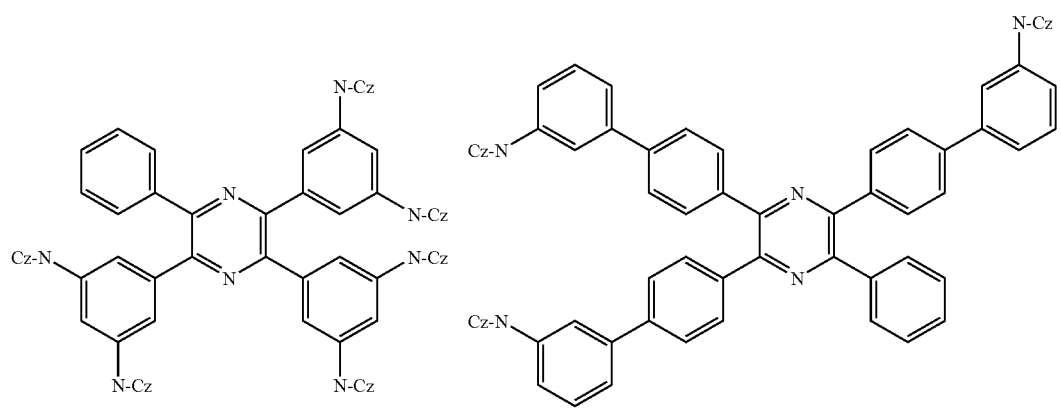

-continued
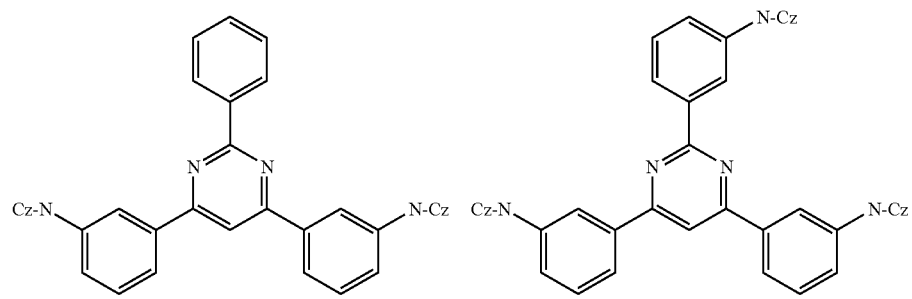
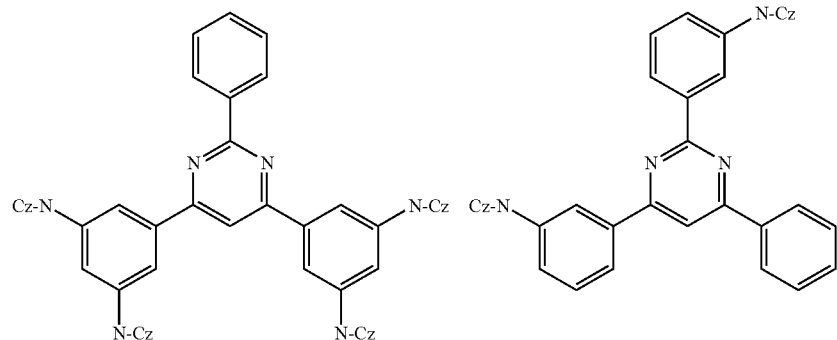
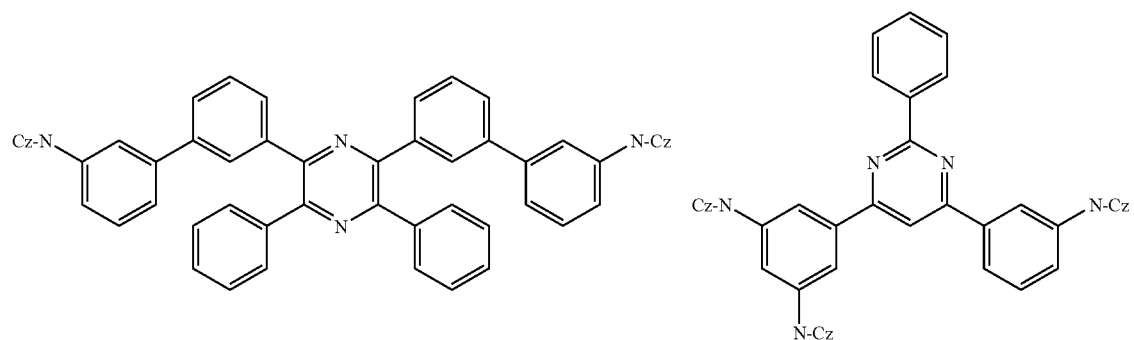
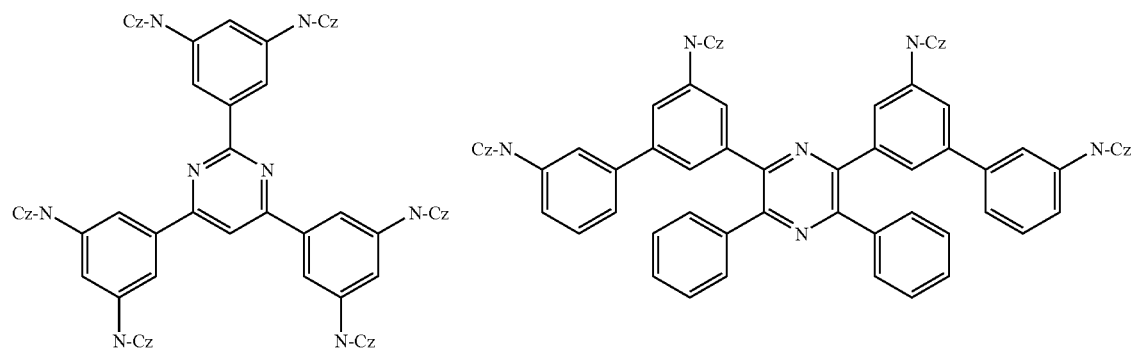
[Compound 36]
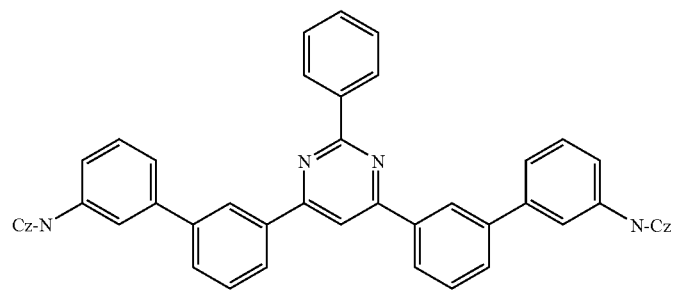

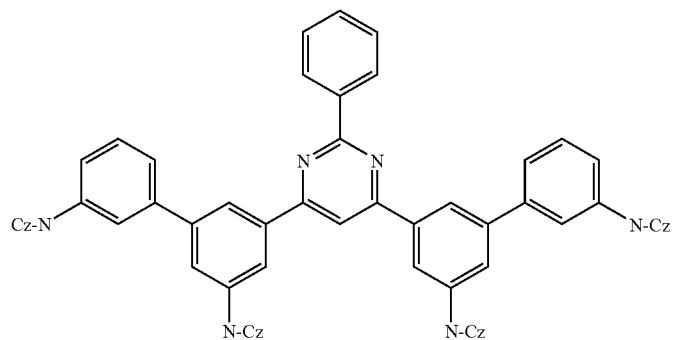
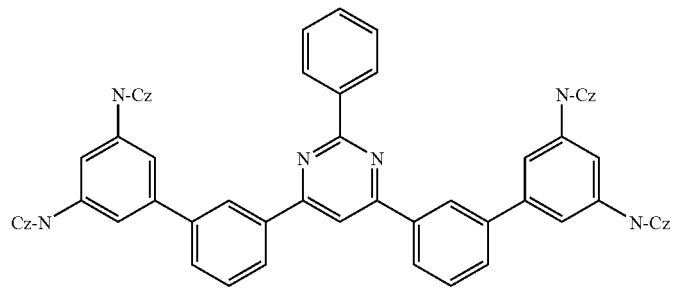
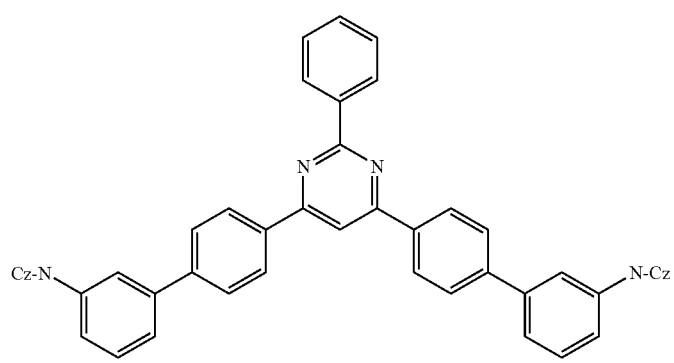
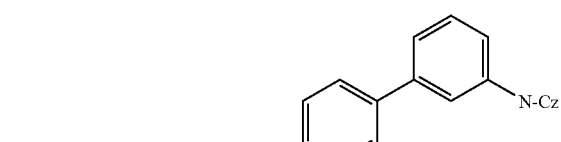
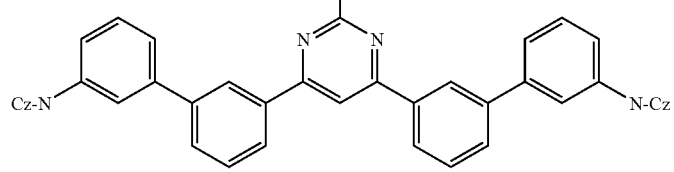
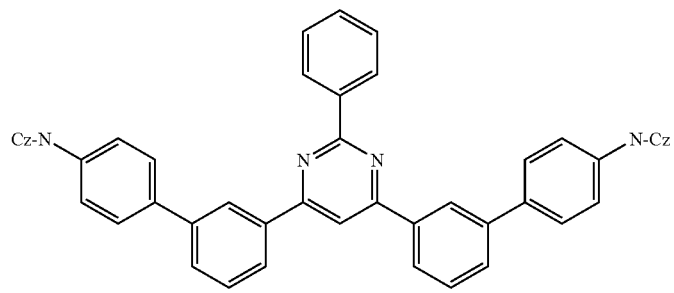

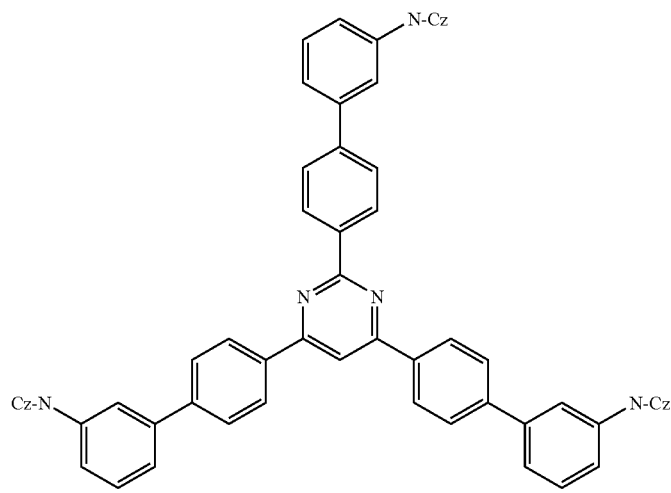
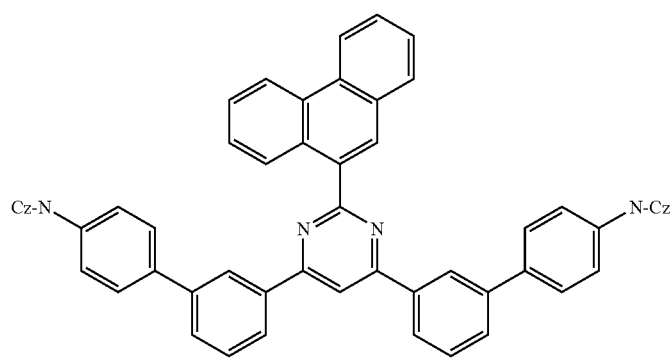
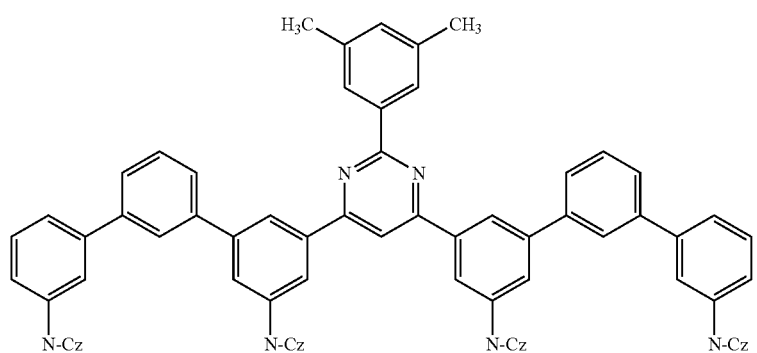
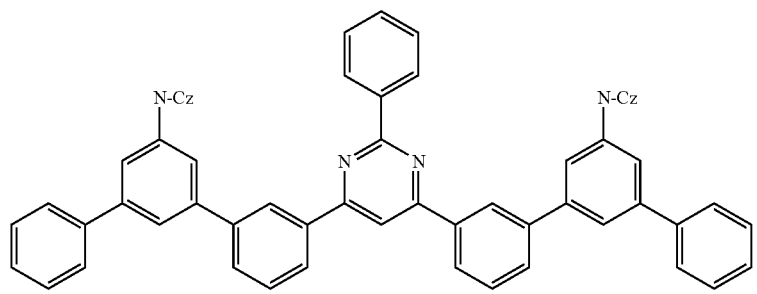

[Compound 37]
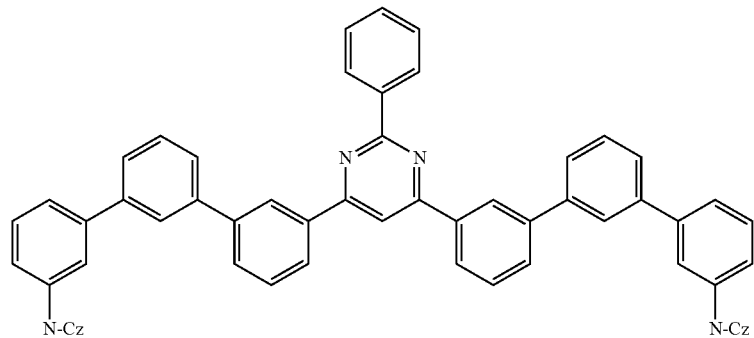
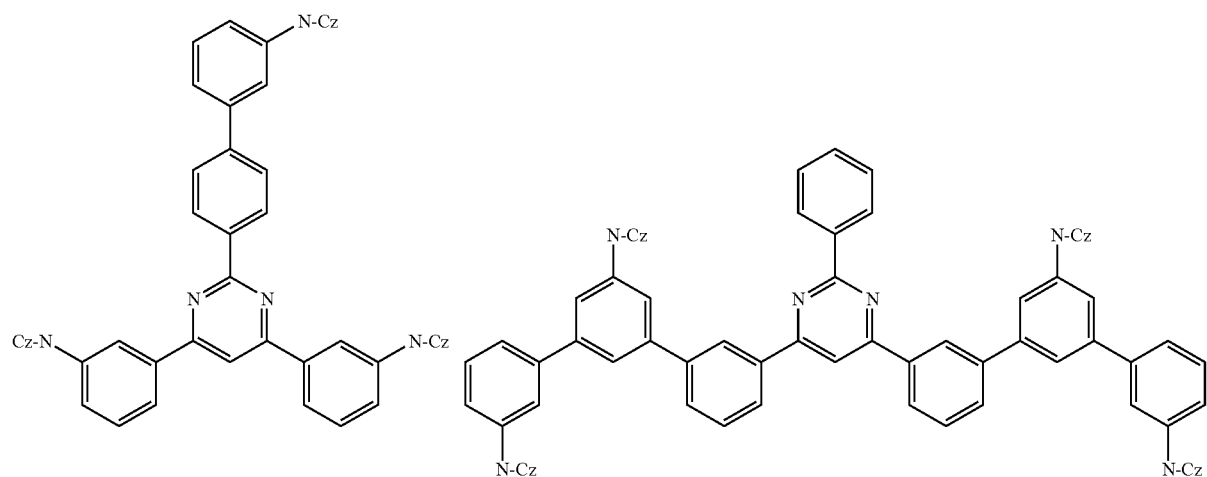
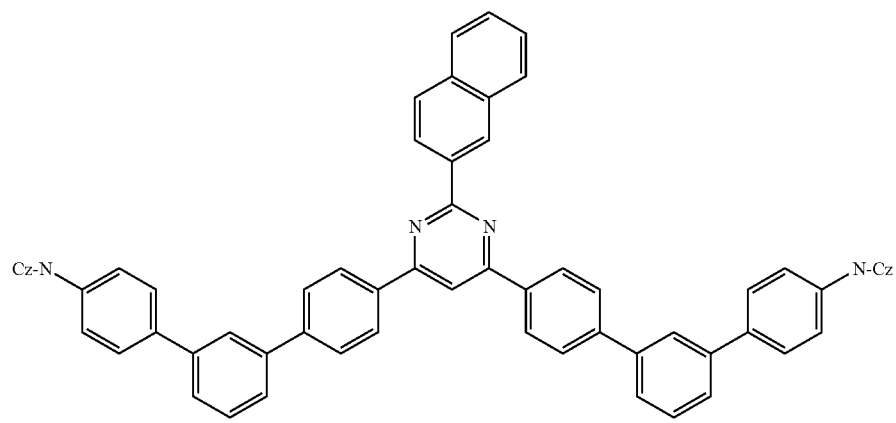

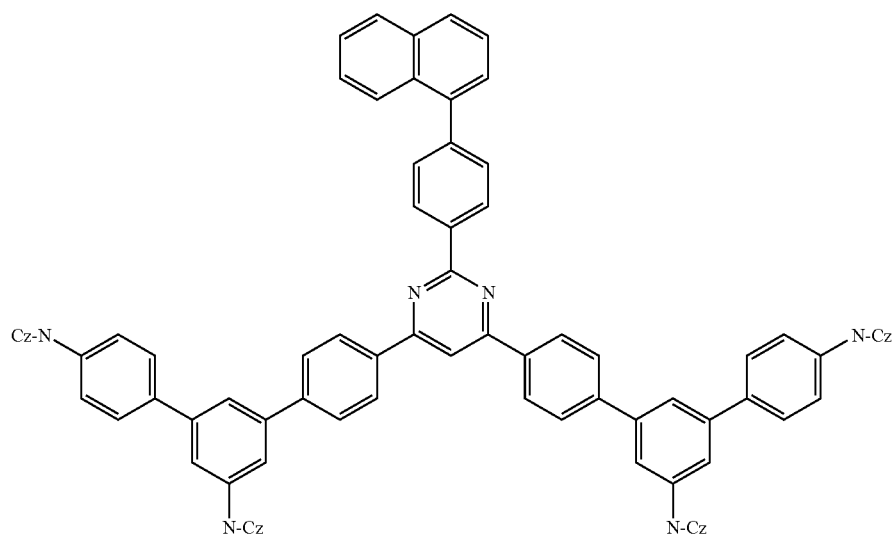
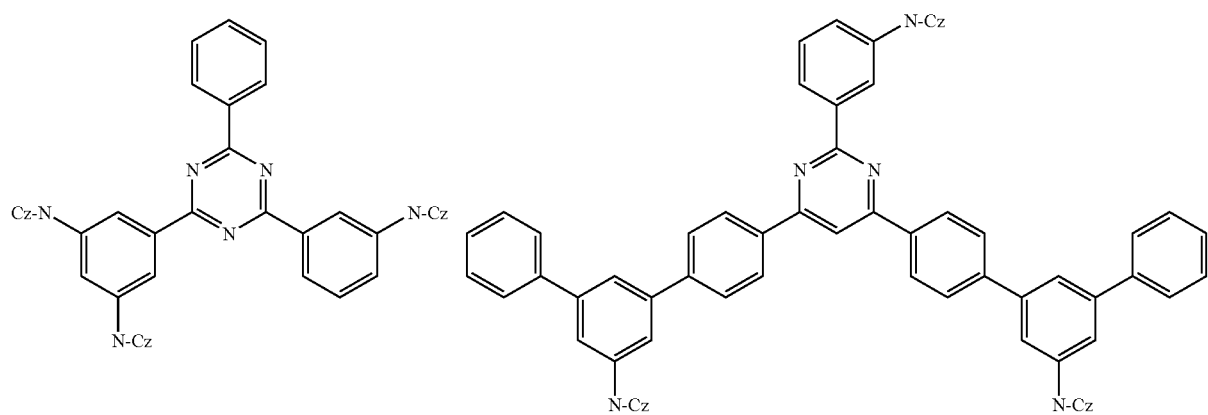
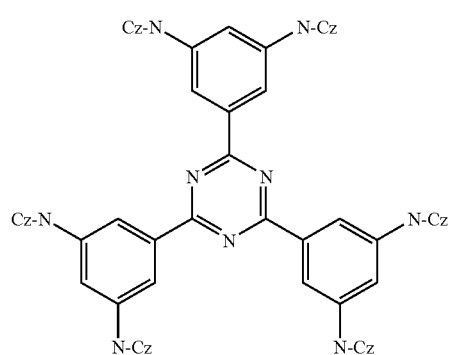
[Compound 38]
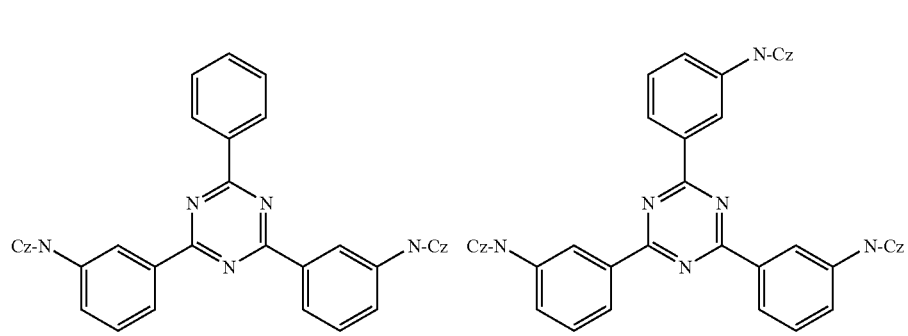

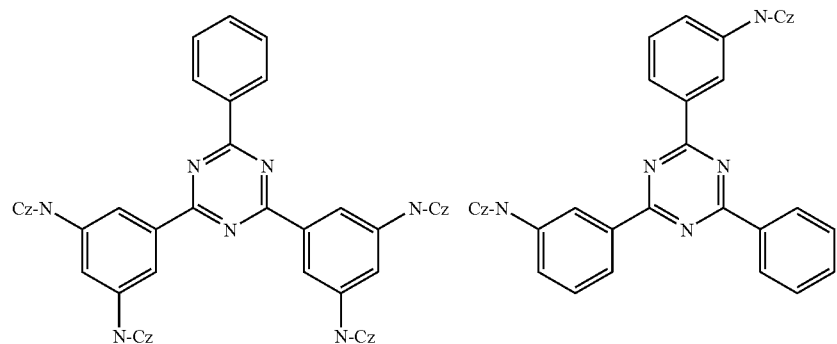
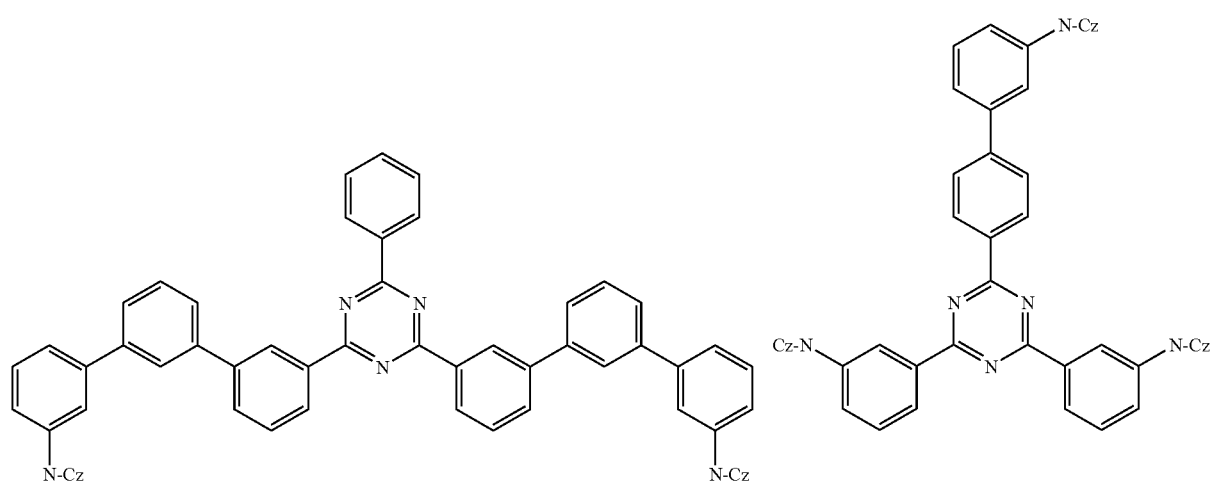
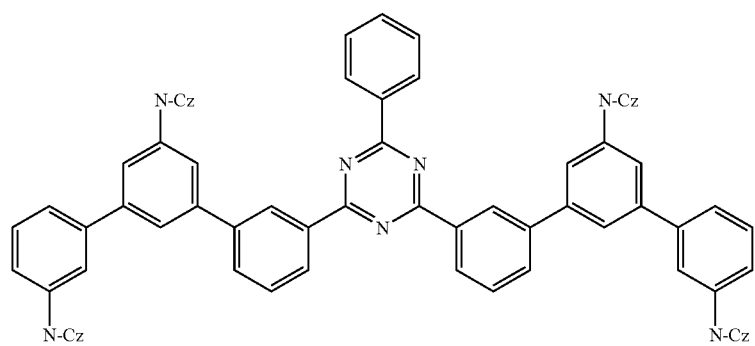
[Compound 39]
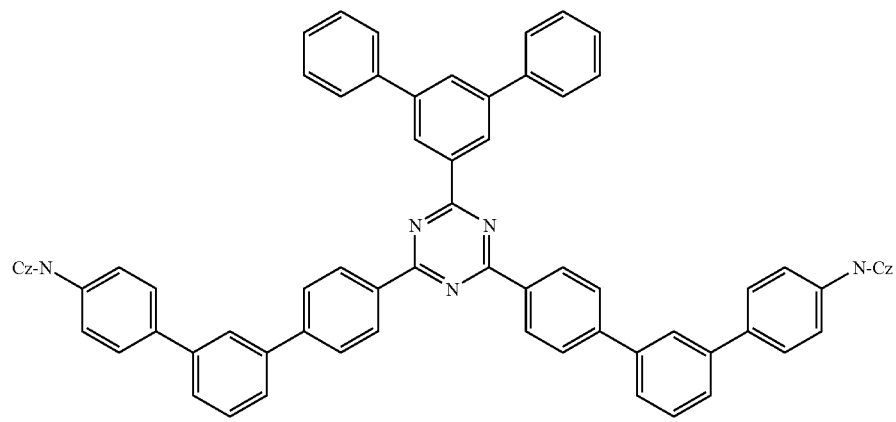

-continued
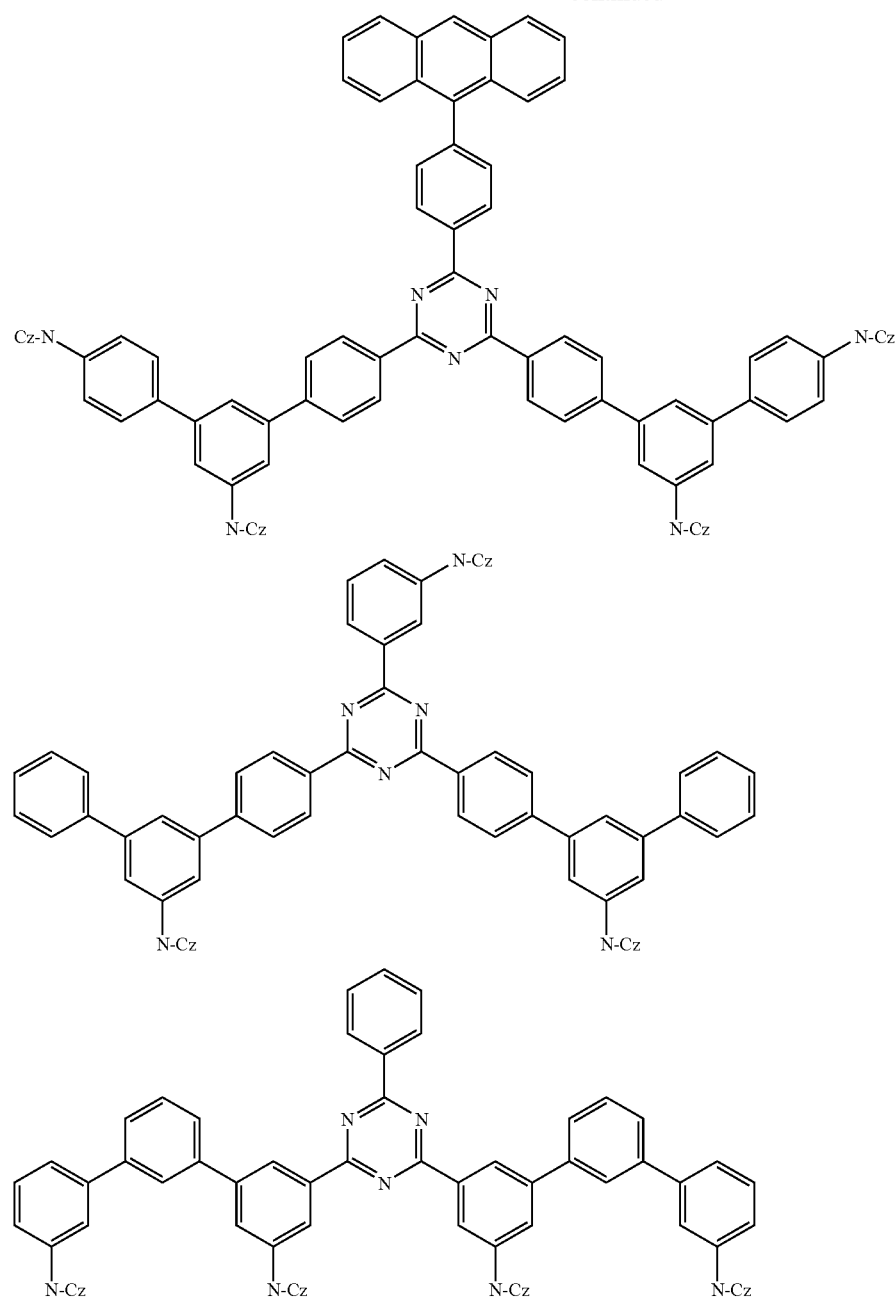
[Compound 40]
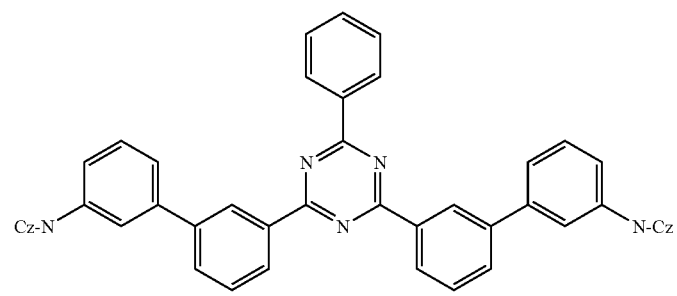

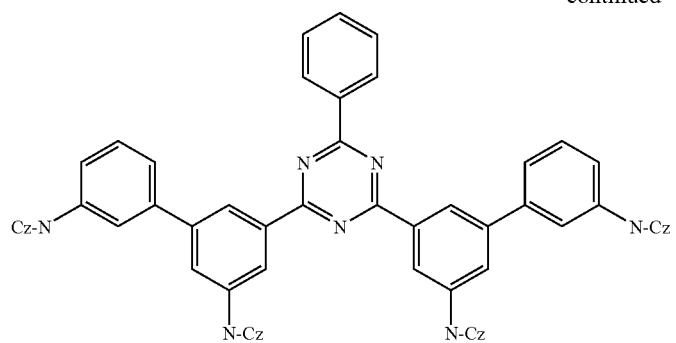
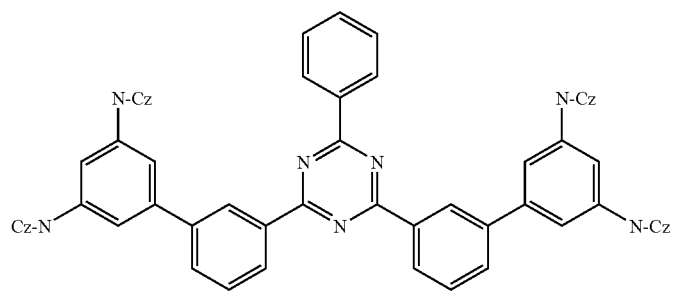
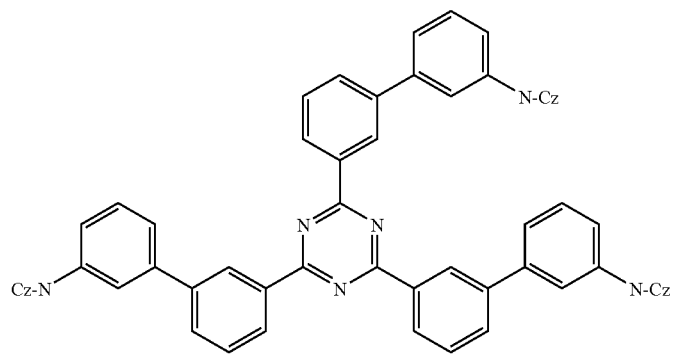
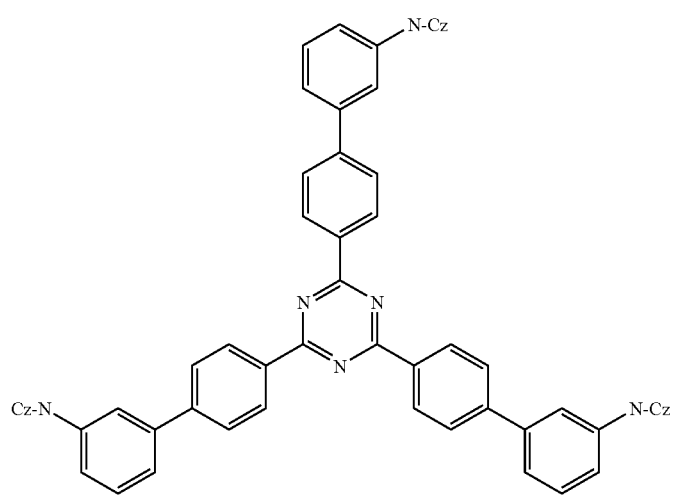

-continued
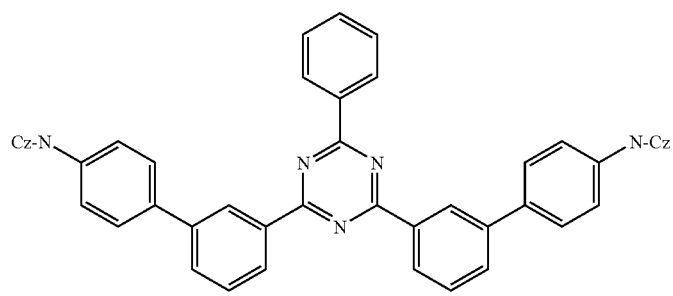
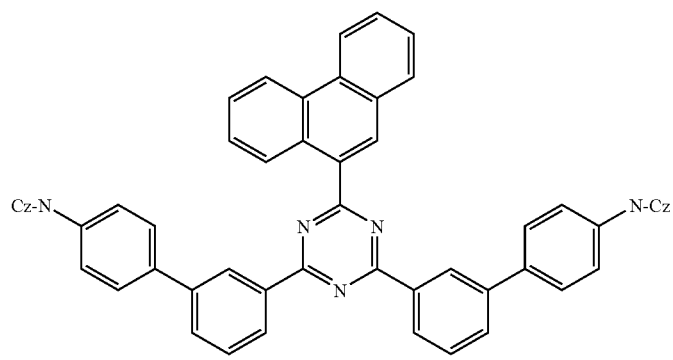
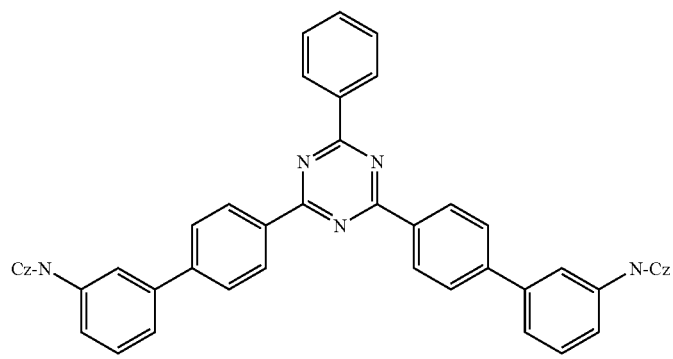
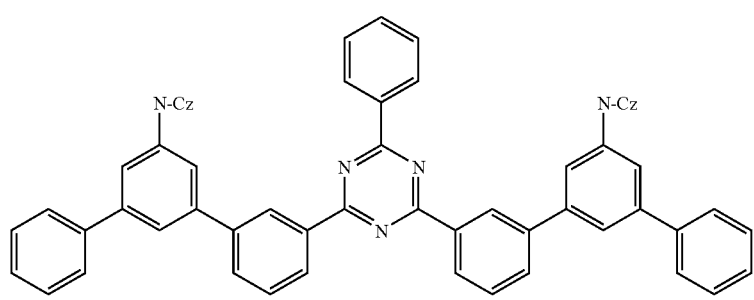

-continued
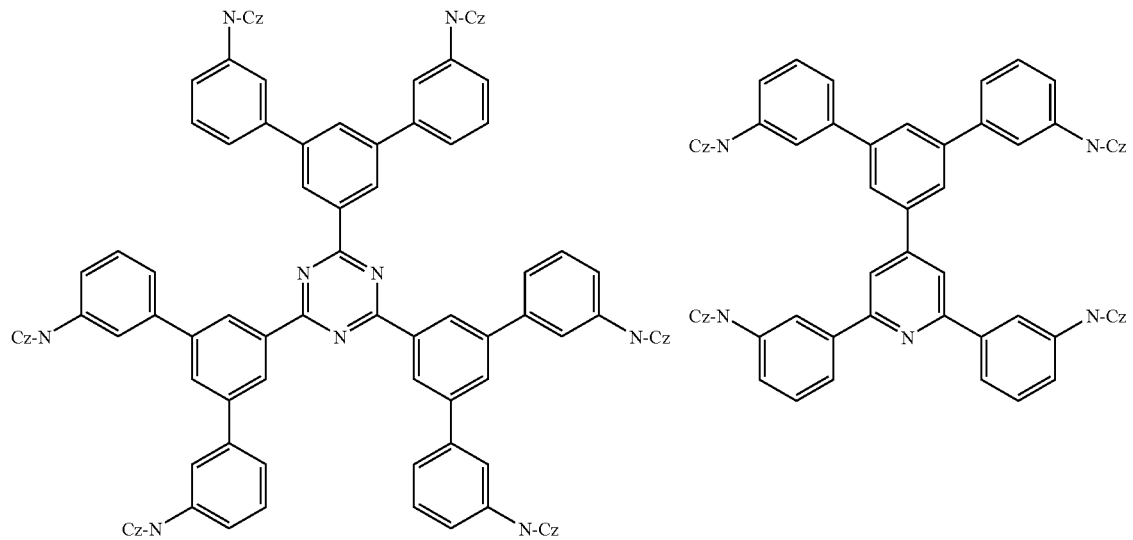
[Compound 41]
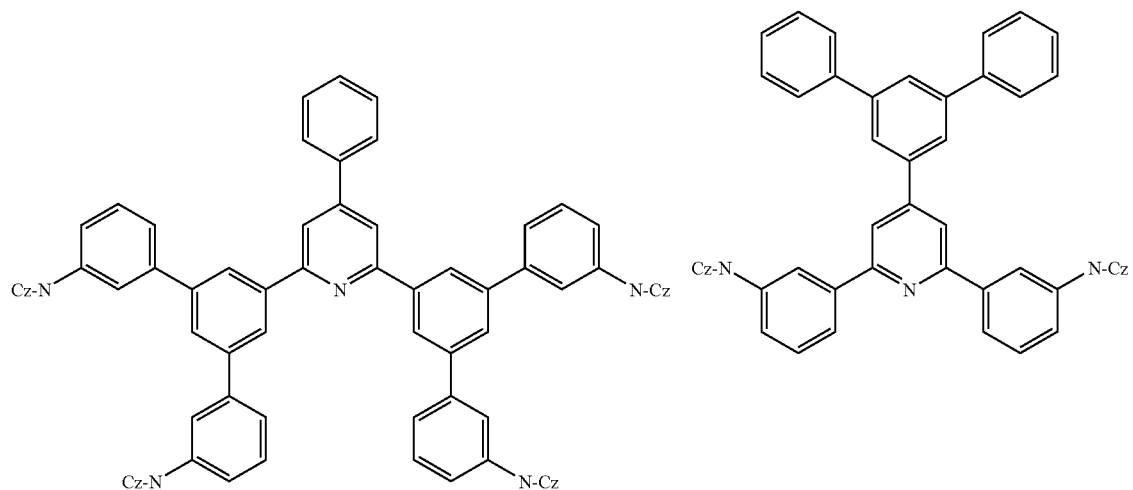
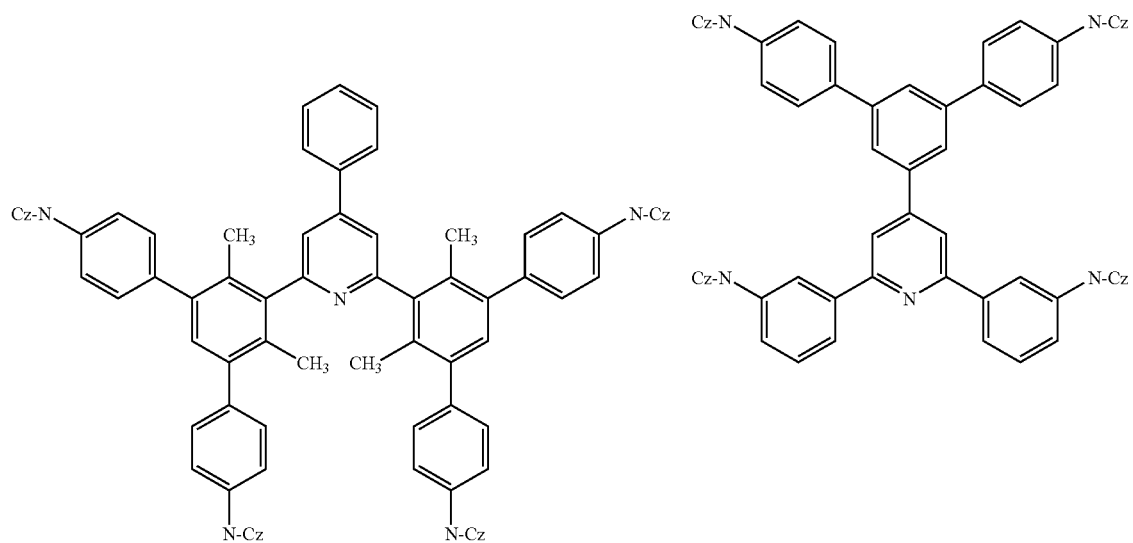

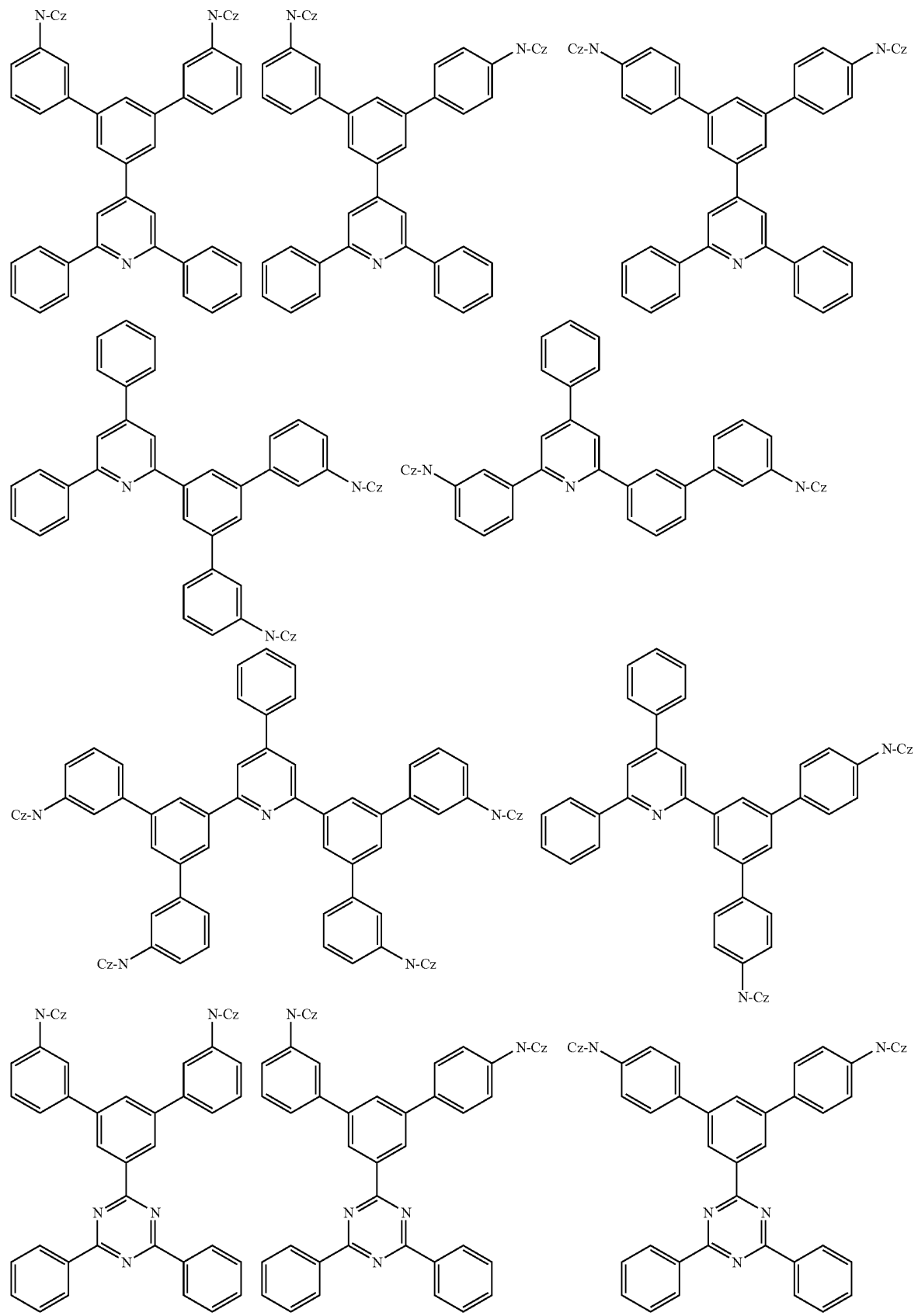
[Compound 42]

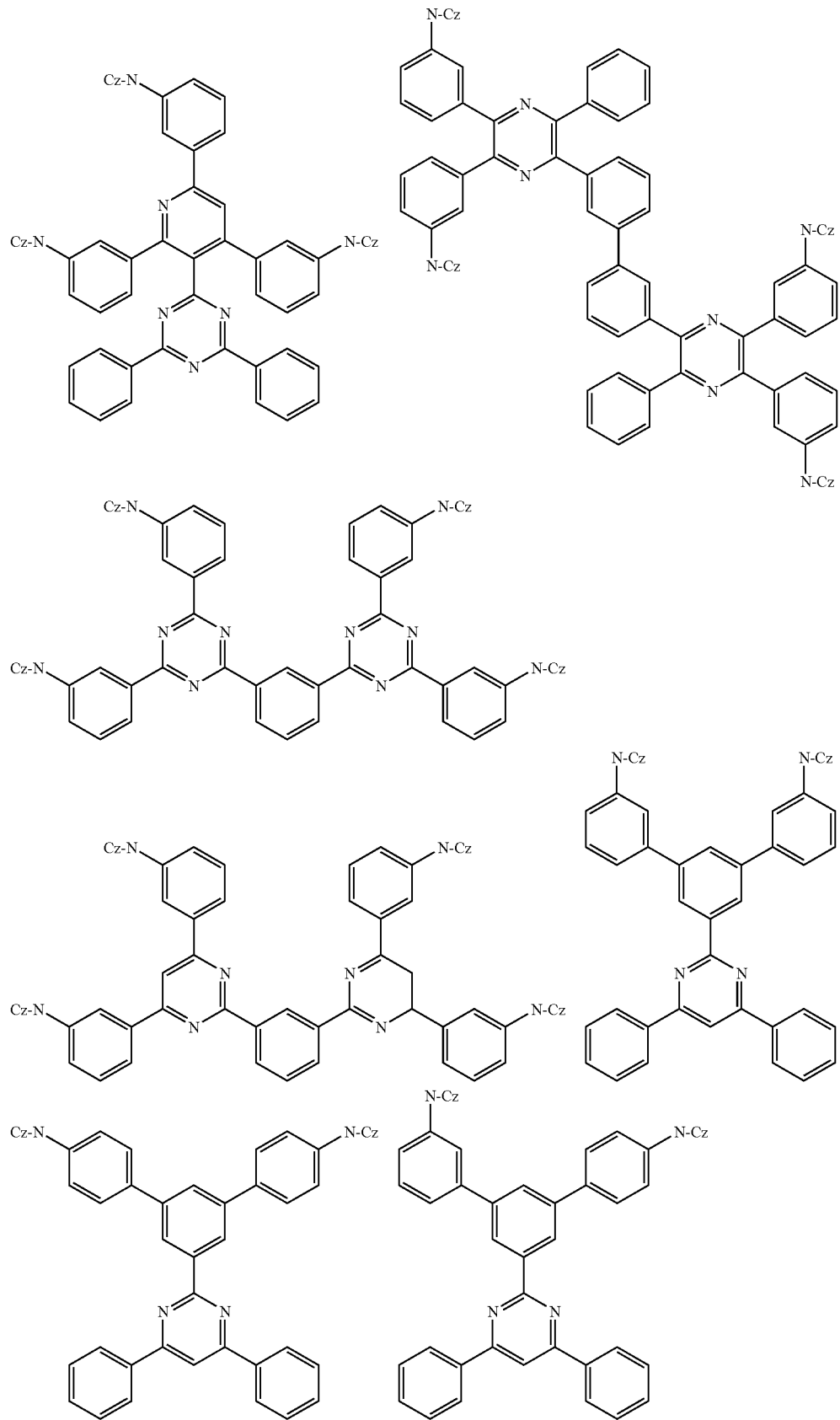
[Compound 43]

[Compound 44]
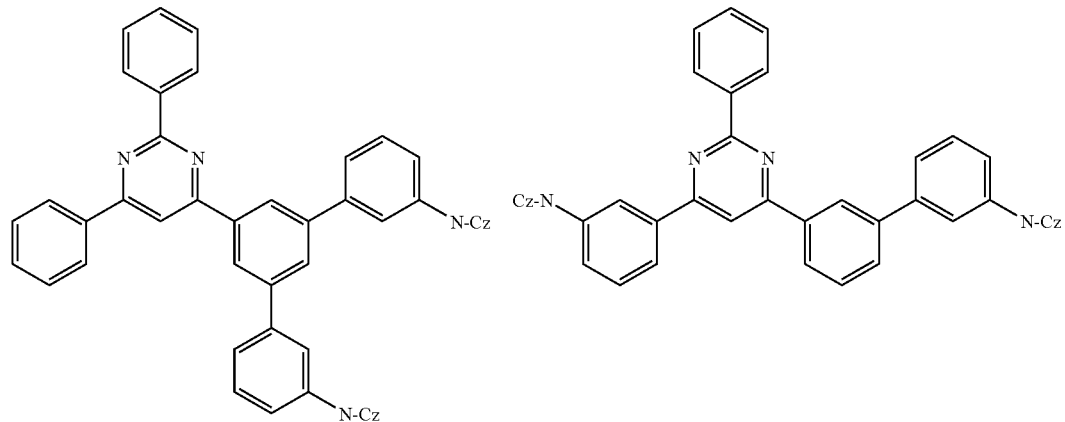
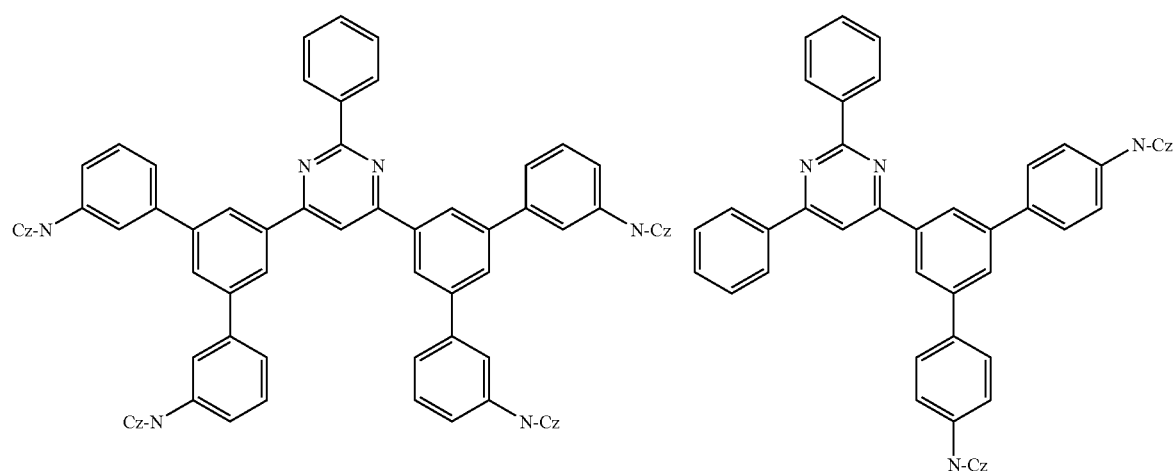
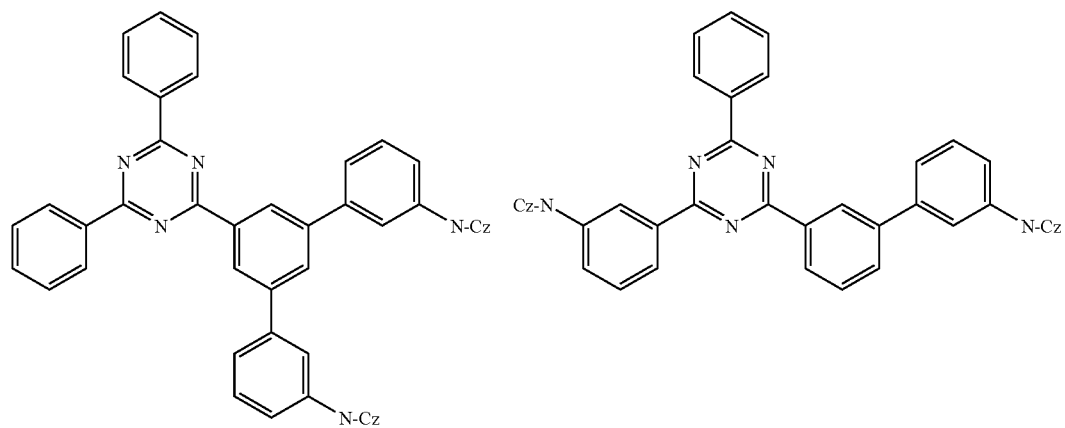

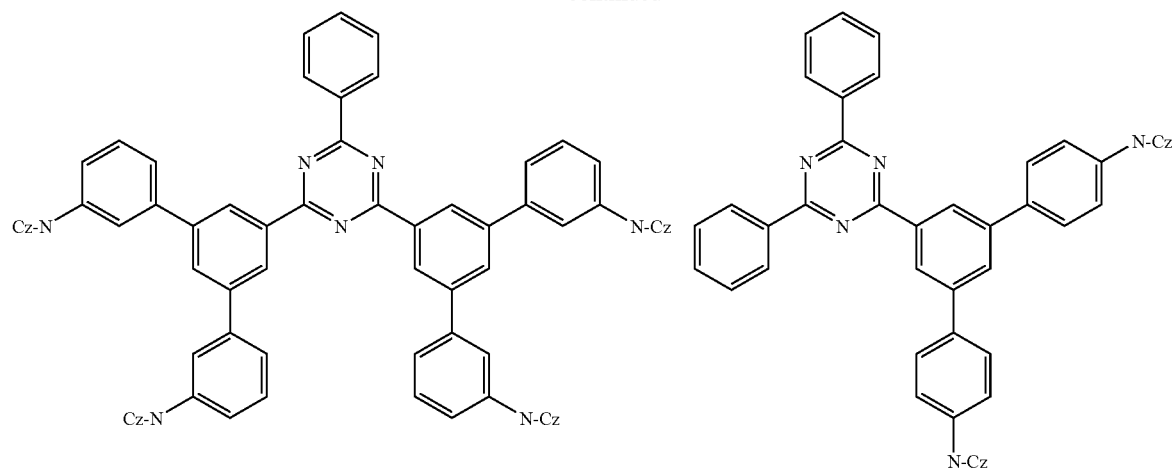
[Compound 45]
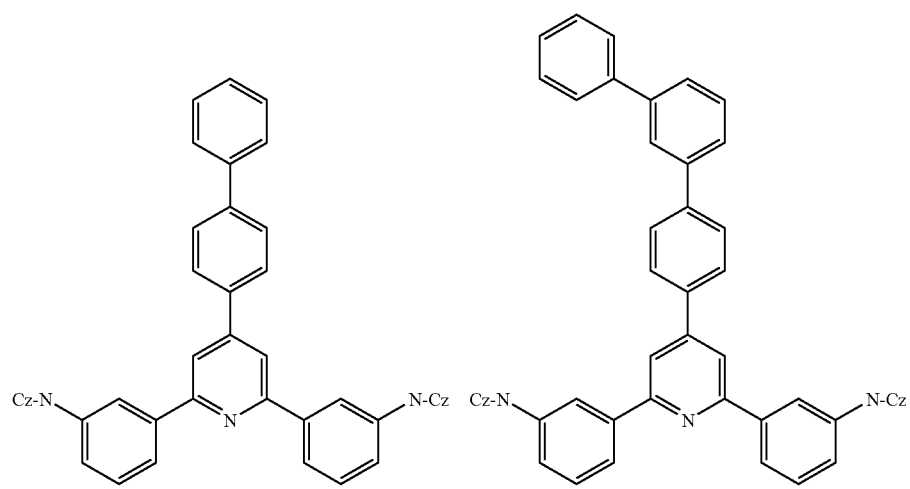
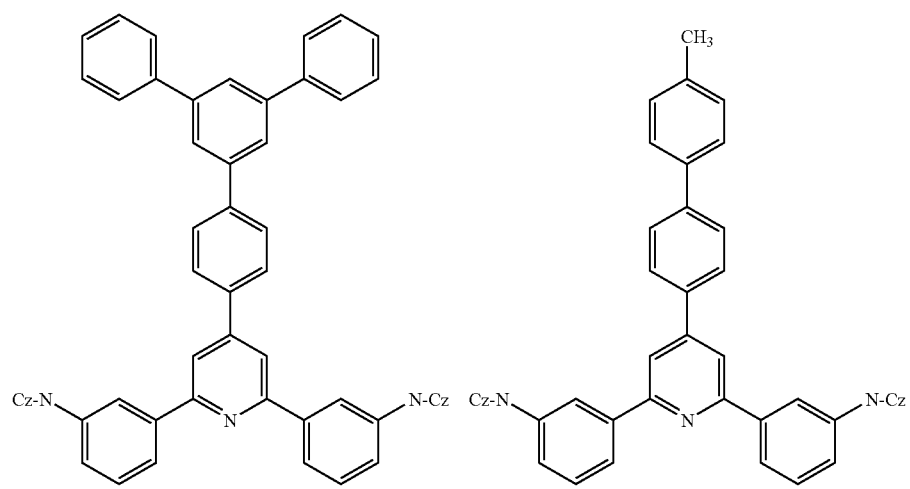

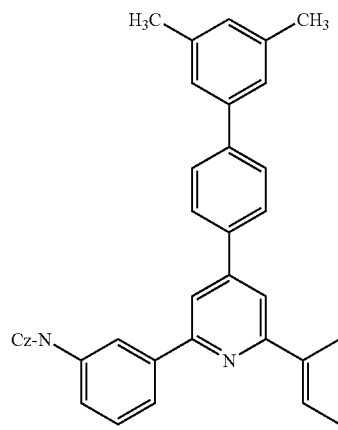
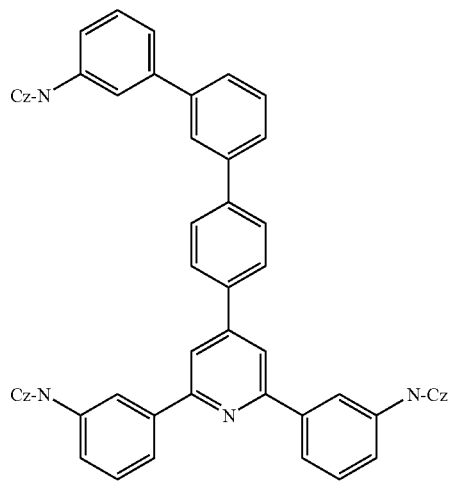
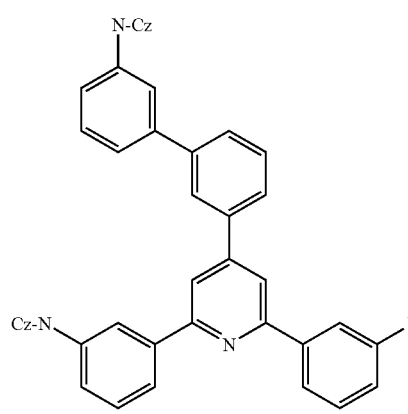
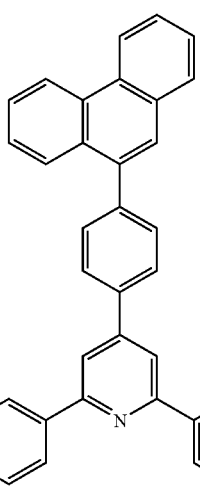
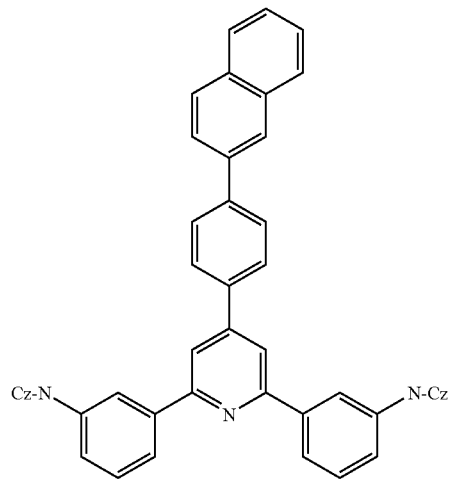

[Compound 46]
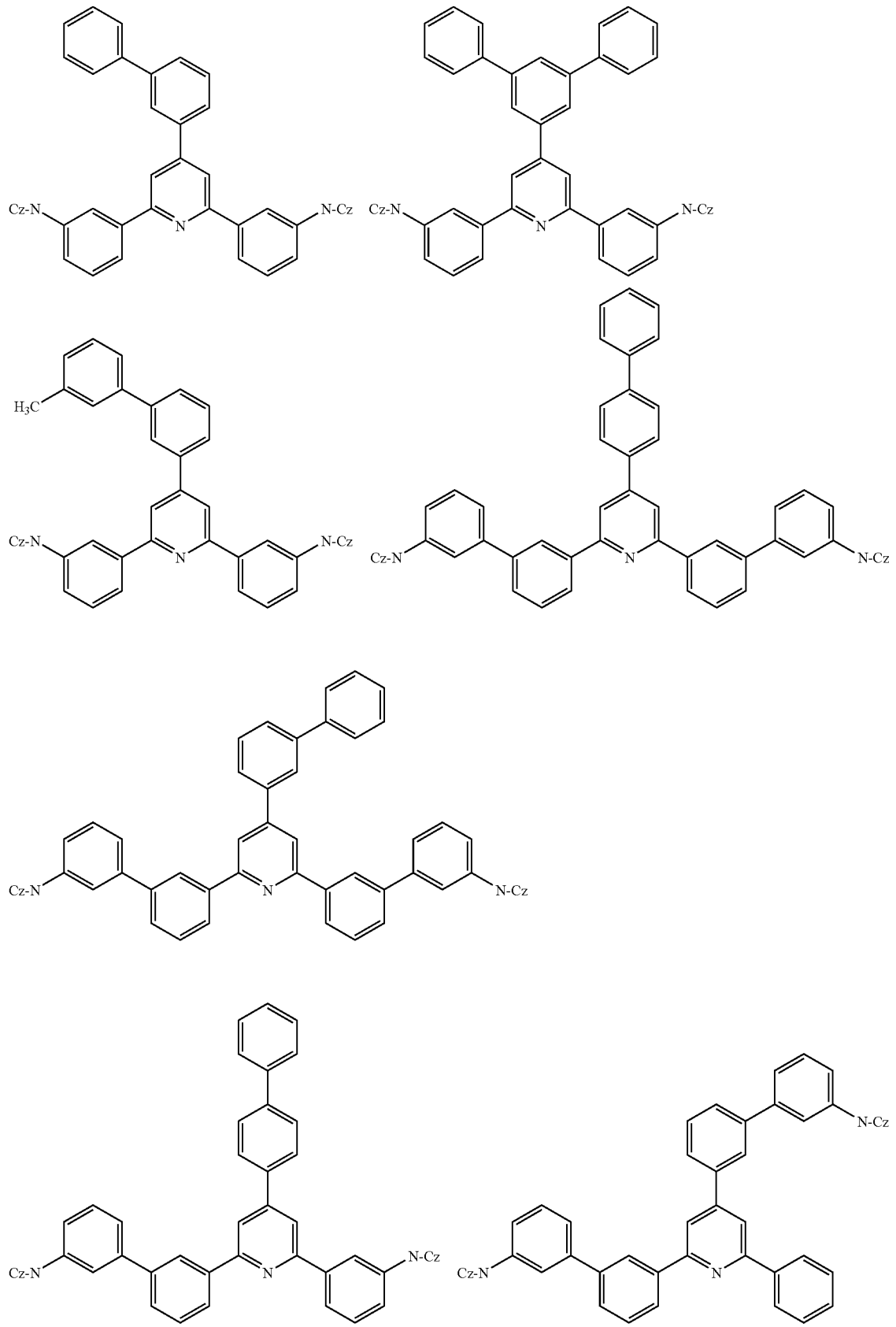

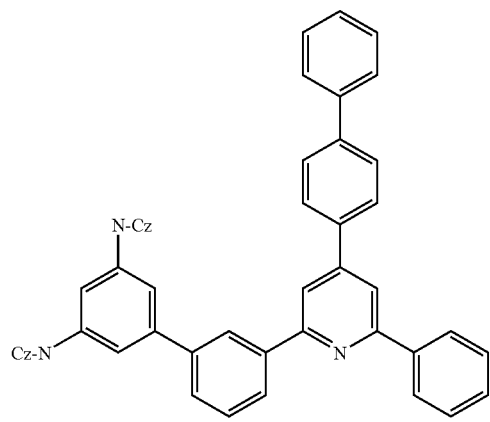
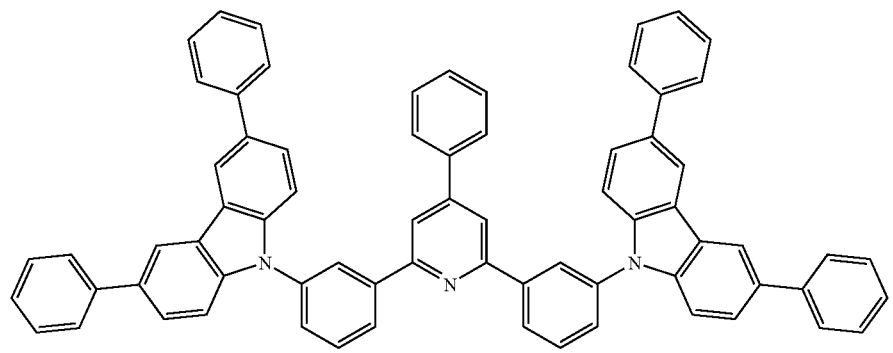
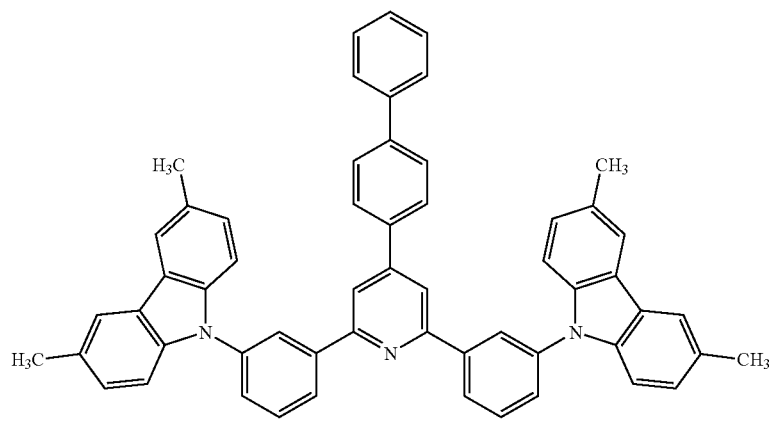
[Compound 47]
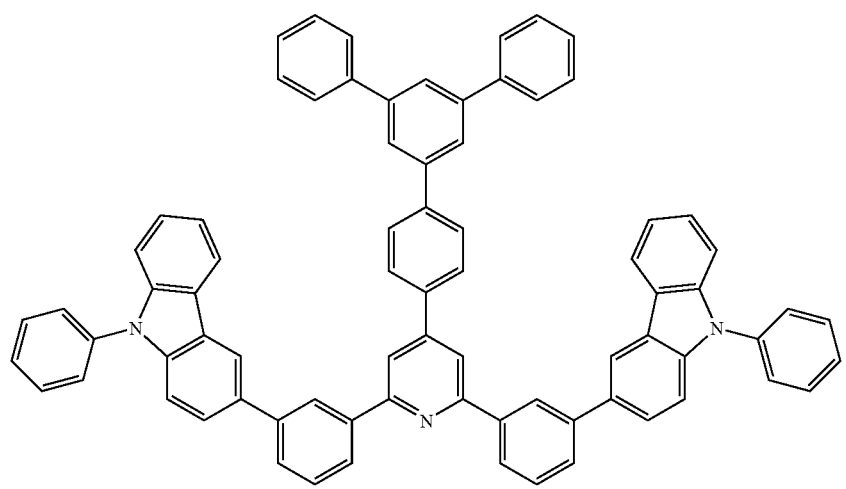

-continued

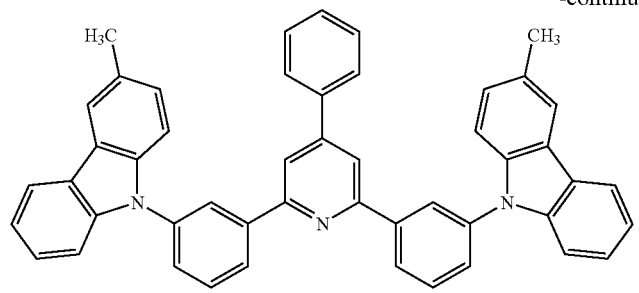

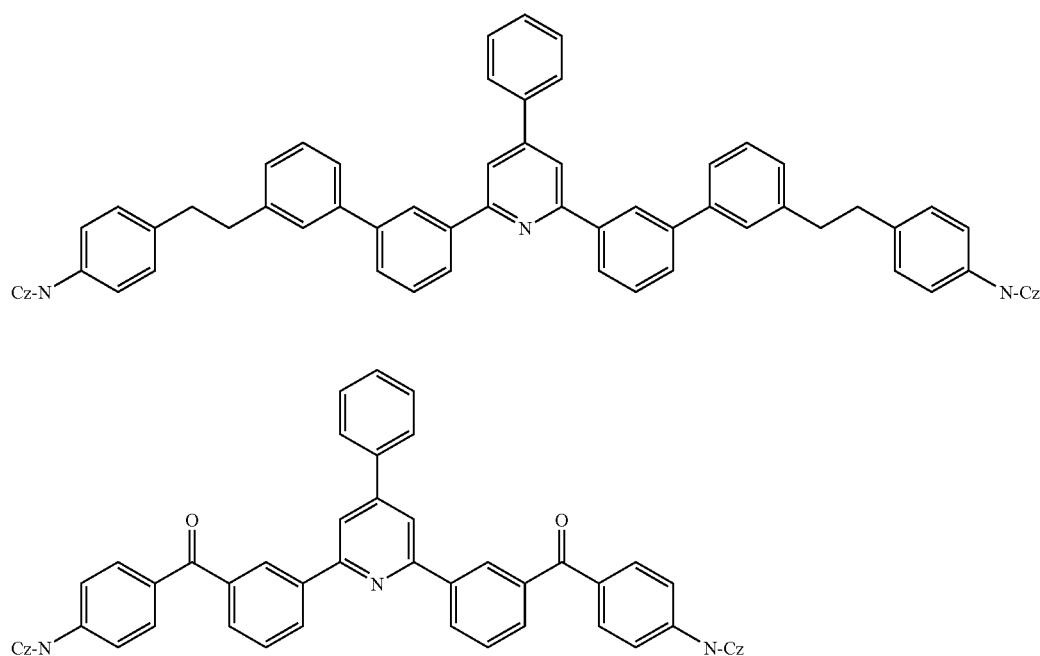

[8] Synthesis Method

In the synthesis of the organic compound according to the present invention, raw materials are selected depending on the structure of a desired compound.

(1) A pyridine ring can be introduced by employing any one of methods described in the following A) to C).

A) When $R^0$—(CHO) is used as a raw material (here, $R^0$ denotes an optional substituent or a linking group), the following methods 1) to 5) can be employed.

1) As disclosed in Angew. Chem. Int. Ed. Engl. (1962) 1626; Synthesis (1976), 1-24; J. Heterocyclic Chem. (1977) 14, 147; Collect. Czech. Commun. 57 (1992) 2, 385-392; or CS-262585, a target organic compound is synthesized by stirring 1 equivalent of an aldehyde and 0.5 to 2 equivalents of an acetylide in the presence of a strong acid such as sulfuric acid in a single solvent such as acetic acid, alcohol, nitrobenzene, toluene, chlorobenzene, dichlorobenzene, or cyclohexane or in a mixed solvent thereof at room temperature for 1 to 10 hr or stirring them in the presence of a strong base such as sodium hydroxide in an alcohol and/or an aqueous solvent under heating condition for 1 to 10 hr to obtain an intermediate (—CH═CR—CO—), and then reacting the resulting intermediate with an acylpyridinium salt and ammonium acetate in an acetic acid solvent under heating condition in the presence of oxygen.

2) As disclosed in Liebigs Ann. Chem. (1974), 1415-1422; J. Org. Chem. 38, (2002) 6, 830-832; or Japanese Unexamined Patent Application Publication No. 2000-186066, a target organic compound is synthesized by reacting an aldehyde and an acetylide in the presence of an oxidizing agent such as boron trifluoride or perchloric acid under heating condition in a toluene solvent to produce a pyrylium salt, and reacting the pyrylium salt with ammonia in water or an alcohol solvent.

[Compound 48]

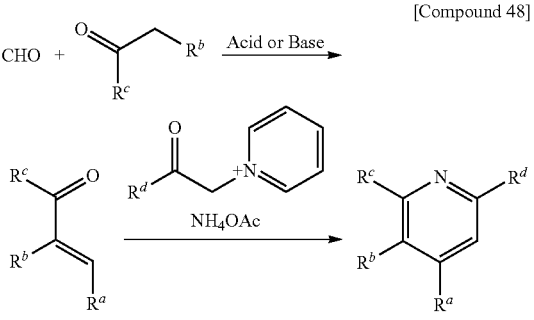

[Compound 49]

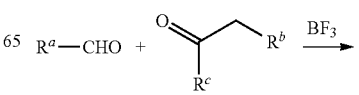

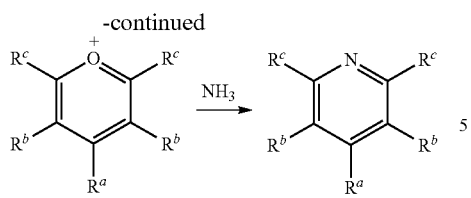

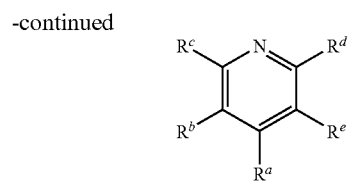

3) As disclosed in J. Am. Chem. Soc. (1952) 74, 200, a target organic compound is synthesized in one step from ammonium acetate, an aldehyde, and an acetylide in a single solvent such as acetic acid, alcohol, nitrobenzene, toluene, chlorobenzene, dichlorobenzene, or cyclohexane or a mixed solvent thereof under heating condition.

[Compound 50]

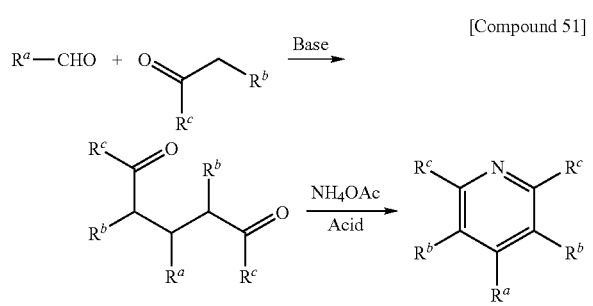

4) As disclosed in Chem. Commun. (Cambridge) (2000) 22, 2199-2200, a target organic compound is synthesized by grinding an aldehyde and 2 equivalents of an acetylide in the presence of a strong base such as sodium hydroxide and in the absence of a solvent at room temperature using a mortar to produce an intermediate (diketone), and then reacting the intermediate with ammonium acetate in a single solvent such as acetic acid, alcohol, nitrobenzene, toluene, chlorobenzene, dichlorobenzene, or cyclohexane or a mixed solvent thereof under heating condition.

[Compound 51]

5) As disclosed in J. Org. Chem. (1988), 53, 5960, a target organic compound is synthesized in one step from an aldehyde and ethylidenevinylamine.

[Compound 52]

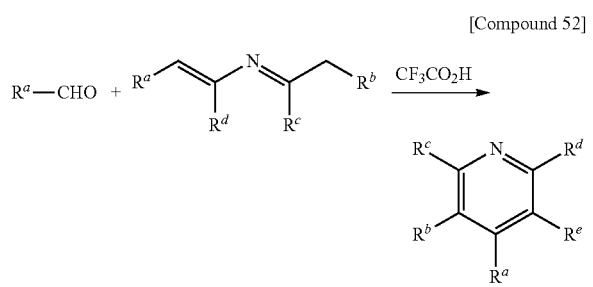

B) When a pyridine ring substituted with a halogen atom such as chlorine, bromine, or iodine at least in one position of 2-, 4- and 6-positions is used as a raw material, the halogen element can be converted to an optional substituent.

For example, as disclosed in Org. Lett. 3 (2001) 26, 4263-4265, a target organic compound is synthesized by reacting zinc bromide or boric acid in the presence of a palladium catalyst under heating condition. In the reaction formula below, dba denotes dibenzylideneacetone.

[Compound 53]

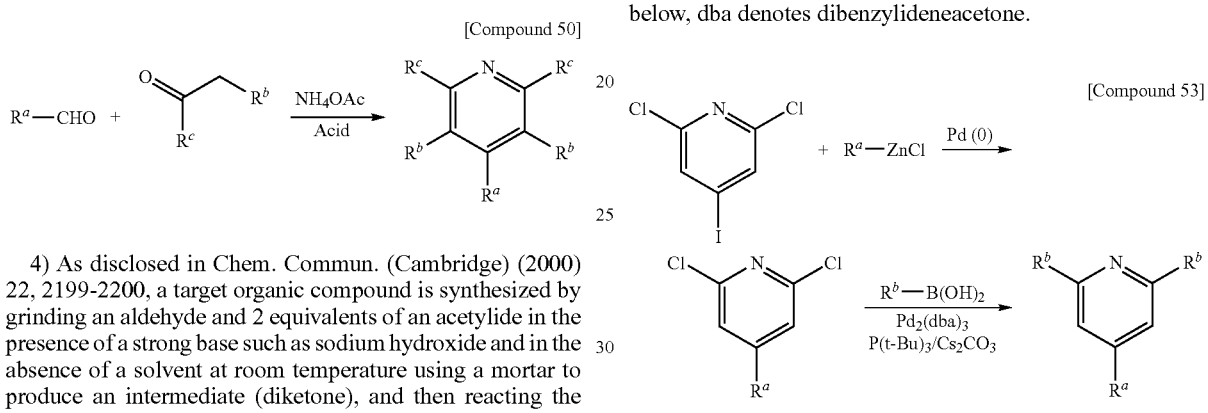

C) Additionally, in introducing various substituents or forming the linking group G or Z, any known technique may be employed according to need. For example, the following 1) to 3) processes can be employed.

1) A target organic compound is synthesized by synthesizing pyridine having an aromatic ring group at 2- and 6-positions thereof by using paraformaldehyde as an aldehyde and an aromatic acyl compound as an acetylide, halogenating 4-position of the pyridine ring by using a halogenating agent such as N-bromosuccinimide to obtain a halide product, converting the halogen atom to B(OH)$_2$ group, ZnCl group, or MgBr group, and coupling this product with the halide product.

2) A second pyridine ring is synthesized by converting the halide product to its lithio product with n-butyllithium, treating the lithio product with N,N-dimethylformamide to synthesize pyridine having aromatic ring groups at 2- and 6-positions thereof and having a CHO group at 4-position thereof, and then reacting the product with an acetylide.

3) A target organic compound is synthesized by stirring 2,6-dichloro-4-iodopyridine described as a starting material in the foregoing B) in the presence of a base using a copper catalyst such as copper powder by heating at 150 to 250° C. to synthesize 2,6,2',6'-tetrachloro-[4,4']bipyridyl, and treating this product in the same manner as in the foregoing B).

The aldehyde (R$^a$—CHO) used in the above-described synthesis processes may be a commonly available reagent. However, if necessary, the aldehyde can be readily synthesized by any one of the following 1) to 13) processes.

1) For example, a halide (R$^a$—X) or a hydrocarbon compound (R$^a$—H) having an active hydrogen atom is reacted with an alkyllithium such as butyllithium or a strong base such as sodium hydride, triethylamine, potassium tert-butoxide, or sodium hydroxide (preferably alkyllithium such as butyllithium), and then the product is treated with N,N-dimethylformamide (Organic & Biomolecular Chemistry (2003) 1, 7, 1157-1170; Tetrahedron Lett. 42 (2001) 37, 6589-6592).

2) A $CO_2R$ group (where R denotes a hydrogen atom, a chlorine atom, an alkyl group, an aromatic ring group, or an amino group) is reduced with lithium aluminum hydride or sodium boron hydride to alcoholize, and then the alcoholized product is oxidized with pyridinium chlorochromate, manganese dioxide, iodoxybenzoic acid, peroxodisulfate, or 2,3-dichloro-5,6-dicyano-1,4-benzoquinone to be converted into CHO (J. Med. Chem. (1990) 33, 2408-2412; Angew. Chem., Int. Ed. 40 (2001) 23, 4395-4397; J. Am. Chem. Soc. (2002) 124, 10, 2245-58; J. Am. Chem. Soc. (1993) 115, 9, 3752-3759; J. Chem. Res., Synop. (2001) 7, 274-276; Synthesis (2001) 15, 2273-2276; Bull. Korean Chem. Soc. 20 (1999) 11, 1373-1374; Arzneim. Forsch. 47 (1997) 1, 13-18; J. Org. Chem. 63 (1998) 16, 5658-5661; J. Chem. Soc. Sec. C; Organic (1968) 6, 630-632).

3) A $CO_2R$ group (where R denotes a hydrogen atom, a chlorine atom, an alkyl group, an aromatic ring group, or an amino group) is reduced with lithium tris(dialkylamino)aluminum hydride or sodium tris(dialkylamino)aluminum hydride to be converted into CHO in one step (Bull. Korean Chem. Soc., 13 (1992) 6, 670-676; Bull. Korean Chem. Soc., 12 (1991) 1, 7-8; Org. Prep. Proced. Int. 24 (1992) 3, 335-337).

4) A $CO_2R$ group (where R denotes a hydrogen atom, a chlorine atom, an alkyl group, an aromatic ring group, or an amino group) is converted into CHO in the presence of hydrogen and a palladium catalyst in one step (Chem. Ber. (1959) 92, 2532-2542; WO00/12457; Bull. Chem. Soc. Jpn. (2001) 74, 1803-1815).

5) A CN group is reduced with lithium tris(dialkylamino) aluminum hydride to be converted into CHO in one step (Bull. Korean Chem. Soc., 13 (1992) 6, 670-676).

6) An Ar—$CH_3$ group (where Ar denotes an aromatic ring group) is directly converted into Ar—CHO by reacting with o-iodylbenzoic acid, Dess-Martin periodinane, or acetoxyiodosylbenzoic acid (J. Am. Chem. Soc. (2002) 124, 10, 2245-58).

7) An Ar—$CH_3$ group (where Ar denotes an aromatic ring group) is converted into Ar—$CH_2OH$ via Ar—$CH_2Br$ and Ar—$CH_2OCH_3COO$, and then oxidized with pyridinium chlorochromate, manganese dioxide, or iodoxybenzoic acid to be converted into CHO (J. Org. Chem. (1993) 58, 3582-3585).

8) An arylcarboxyaldehyde is synthesized by the reaction of a Vilsmeier reagent and 1-ethyl-1-arylallyl alcohol (Indian Journal of Chemistry (1988) 27B, 213-216).

9) An arylcarboxyaldehyde is synthesized by the reaction of a Vilsmeier reagent and a 1,4-cyclohexadiene (Synthesis (1987), 197-199; Synthesis (1985), 779-781).

10) An Ar—$CH_3$ group (where Ar denotes an aromatic ring group) is brominated to Ar—$CH_2Br$ with bromine or N-bromosuccinimide, and the Ar—$CH_2Br$ is reacted with a 2-nitropropane carboanion reagent or hexamethylenetetramine to be converted into Ar—CHO (Collect. Czech. Chem. Commun. (1996) 61, 1464-1472; Chem. Eur. J. (1996) 2, 12, 1585-1595; J. Chem. Research (S), (1999) 210-211).

11) An arylaldehyde (e.g., 1,3,5-triformylbenzene) is obtained from a polymethinium salt (e.g., heptamethinium salt) (Collect. Czech. Chem. Commun. (1965) 30, 53-60).

12) 1,3,5-Triformylbenzene is obtained by self-condensation of triformylmethane (Collect. Czech. Chem. Commun. (1962) 27, 2464-2467).

13) An Ar—$CHBr_2$ group (where Ar denotes an aromatic ring group) is converted into ArCHO by using a dialkylamine (Bulletin de La Societe Chmique De France (1966) 9, 2966-2971).

The ketone ($R^c$—CO—$CH_2$—$R^b$) used in the above-described synthesis processes may be a commonly available reagent. However, if necessary, the ketone can be readily synthesized by the following process 1) or 2).

1) An $R^c$—$CO_2R$ group (where R denotes a hydrogen atom, a chlorine atom, an alkyl group, an aromatic ring group, or an amino group) is treated with various types of alkylating agents (e.g., alkyllithium, dimethylsulfuric acid, or dimethyl sulfoxide) to obtain $R^c$—CO—$CH_2$—$R^b$ (J. Am. Chem. Soc. (1959) 81, 935-939; J. Am. Chem. Soc. (1961) 83, 4668; Tetrahedron Lett. (1967) 1073; J. Chem. Soc. (1960) 360; J. Chem. Soc., Perkin Trans. 1 (1977) 680; JP-5-5062039).

2) $R^c$—CO—$CH_2$—$R^b$ is synthesized by a reaction of an acylating agent such as an acid chloride in the presence of Lewis acid catalyst such as aluminum chloride (extremely popular Friedel-Crafts reaction).

In addition, synthesis processes described or cited in "Heterokan No Kagaku—Iyakuhin No Kiso (Chemistry of Heterocyclic Compounds—Basics of Medicine" (2002, Kunieda, et al., Kagaku-Dojin), "Heterocyclic Chemistry" (4th ed., 2000, J. A. Joule and K. Mills, Blackwell Science Co.), "Shinpen Heterokan Kagobutsu Kiso-hen, Oyo-hen (New Heterocyclic Compounds, Basics and Advanced)" (2004, Nakayama, et al., Kodansya), and "Boruharuto/Syoa Gendai Yuki Kagaku, Ge (Vollhardt & Schore Organic Chemistry II" (2004, K. P. C. Vollhardt, Kagaku-Dojin) can be employed.

A pyrazine ring can be introduced, for example, by employing any one of the following processes 1] to 7].

1] A pyrazine is synthesized by synthesizing a benzoin intermediate from the same or different aromatic aldehydes (Khim, -Farm. Zh. 25 (1991) 4, 28-31; Helvetica Chimica Acta (1985) 68(3), 592-599; J. Chem. Res. Synop. (2002) 6, 262-263; Ser C. (19966) 263, 1156; J. Am. Chem. Soc. (2002) 124, 12084-12085; Advanced Synthesis & Catalysis (2002) 344, 96-103; PCT Int. Appl., 2002002753, 10 Jan. 2002; J. Org. Chem. (2001) 66, 8010-8014; J. Chem. Soc., Perkin Trans. 1 (2001) 7, 633-635; Tetrahedron Lett. (2000) 41, 10159-10162; J. Org. Chem. (1983) 48, 459-464; Journal fuer Praklische Chemie (Leipzig) (1962) 16, 1-7), from α-dihydro form (Tetrahedron: Asymmetry (1998) 9, 4117-4122), from aryllithium (J. Org. Chem. (1982) 47, 4347-4348; Tetrahedron Lett. (1989) 30, 989-992), from α-diketone form (Journal fuer Praklische Chemie (Leipzig) (1962) 16, 1-7), or from arylester (Tetrahedron Lett. (1980) 21, 2227-2228); and reacting the benzoin intermediate with ammonia and/or ammonium acetate in the presence of oxygen (J. Org. Chem. (1937) 2, 328; Bull. Soc. Chim. Fr. (1968) 4970; Helvetica Chimica Acta (1985) 68(3), 592-599; C. R. Seances Acad. Sci., Ser C. (1966) 263, 1156).

[Compound 54]

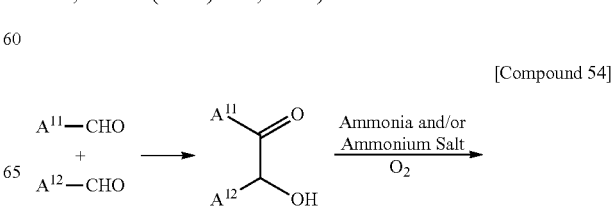

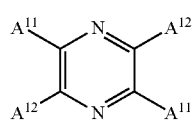

2] A pyrazine is synthesized by cyclizing α-diketone and α-diamine (J. Org. Chem. 57 (1992) 24, 6653-6657; Helvetica Chimica Acta (1976) 59, 1169; Helvetica Chimica Acta (1973) 56, 610) and subjecting the product to oxidation treatment (Helvetica Chimica Acta (1976) 59, 1169).

[Compound 55]

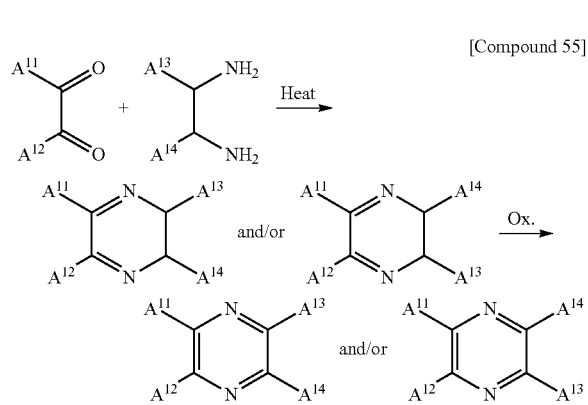

4] A pyrazine is synthesized by reacting the same or different aromatic amides with ammonia or ammonium salt (Helvetica Chimica Acta (1985) 68, 592-599; Japanese Unexamined Patent Application Publication No. 06-065212).

[Compound 57]

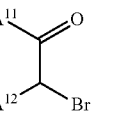 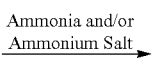 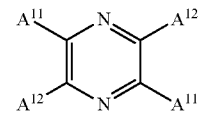

5] A target compound is obtained by preparing a dihalide of pyrazine via an amino-acid anhydride from amino acid (Bull. Soc. Chem. Fr. (1942) 9, 487; J. Am. Pharm. Assoc., Sci. Ed. (1957) 46, 391) or another path (J. Heterocyclic Chem. (1986) 23, 871-875; Chemical & Pharmaceutical Bull. (1979) 27, 2980-2987; J. Am. Chem. Soc. (1956) 78, 4071-4077), and subjecting the dihalide of pyrazine to a coupling reaction with arylboronic acid (Suzuki Coupling method), an azole such as carbazole, indole, pyrrole, or pyrazole (Suzuki Coupling method (Tetrahedron 48 (1992) 37, 8117-8126) or Ullman method), or tetraaryl tin (Heterocycles (1986) 24, 785-792).

[Compound 58]

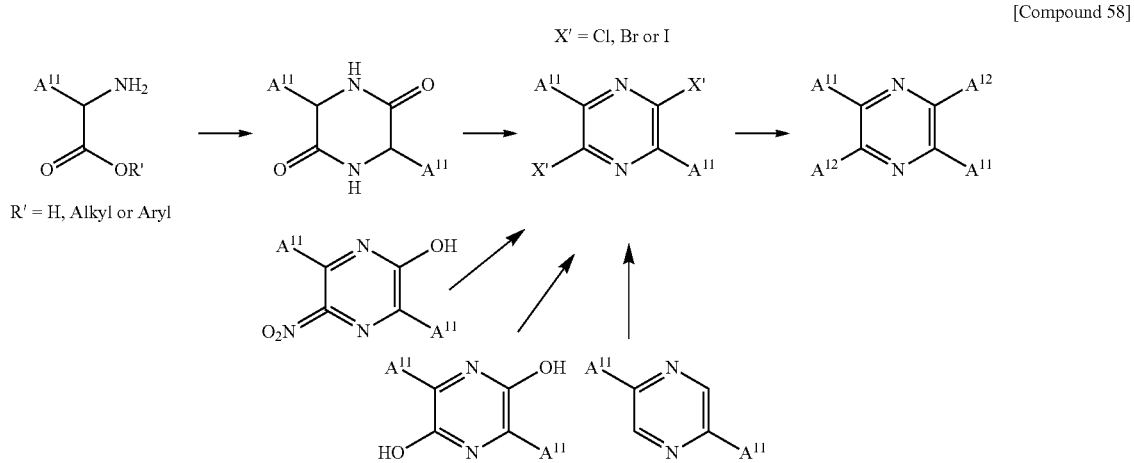

3] A pyrazine is synthesized by reacting α-haloketone with ammonia and/or ammonium salt (Japanese Unexamined Patent Application Publication No. 03-048666).

6] A pyrazine is synthesized from pyrrole (Justus Liebigs Ann. Chem. (1952) 578, 226).

[Compound 59]

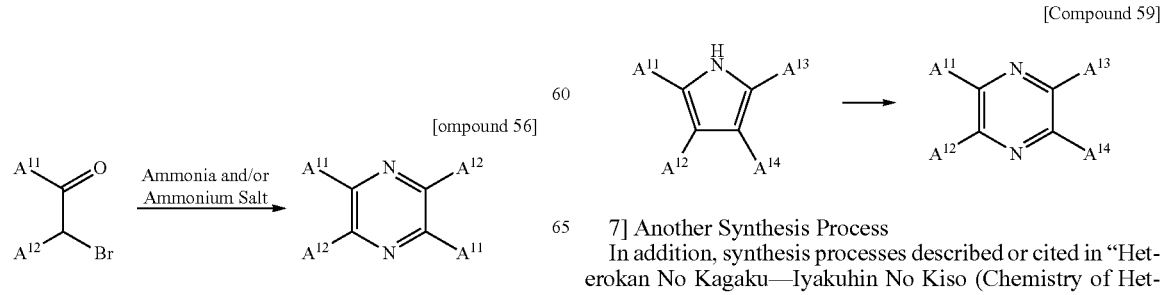

[ompound 56]

7] Another Synthesis Process

In addition, synthesis processes described or cited in "Heterokan No Kagaku—Iyakuhin No Kiso (Chemistry of Heterocyclic Compounds—Basics of Medicine" (2002, Kunieda, et al., Kagaku-Dojin), "Heterocyclic Chemistry" (4th ed., 2000, J. A. Joule and K. Mills, Blackwell Science Co.), "Shinpen Heterokan Kagobutsu Kiso-hen, Oyo-hen (New Heterocyclic Compounds, Basics and Advanced)" (2004, Nakayama, et al., Kodansya), and "Boruharuto/Syoa GendaiYuki Kagaku, Ge (Vollhardt & Schore Organic Chemistry II" (2004, K. P. C. Vollhardt, Kagaku-Dojin) can be employed.

(3) The introduction of a pyrimidine ring may be conducted by a method using a palladium catalysis disclosed in Journal of Organometallic Chemistry, 663 (1-2), 46-57, 2002 or Journal of Organic Chemistry, 66 (21), 7125-7128, 2001. In addition, synthesis processes described or cited in "Heterokan No Kagaku—Iyakuhin No Kiso (Chemistry of Heterocyclic Compounds—Basics of Medicine" (2002, Kunieda, et al., Kagaku-Dojin), "Heterocyclic Chemistry" (4th ed., 2000, J. A. Joule and K. Mills, Blackwell Science Co.), "Shinpen Heterokan Kagobutsu Kiso-hen, Oyo-hen (New Heterocyclic Compounds, Basics and Advanced)" (2004, Nakayama, et al., Kodansya), and "Boruharuto/Syoa GendaiYuki Kagaku, Ge (Vollhardt & Schore Organic Chemistry II" (2004, K. P. C. Vollhardt, Kagaku-Dojin) can be employed.

(4) As a process for introducing a triazine ring, the following processes 1> to 3> can be employed.

1> Process for Synthesizing from an Aryl Cyanide

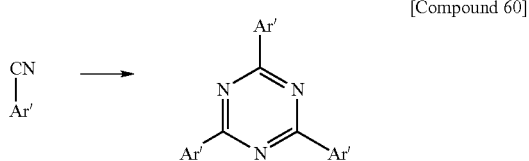

[Compound 60]

(In the formula, Ar' denotes an arylene group, heteroarylene group, or unsaturated hydrocarbon group which may have an optional substituent (e.g., a halogen atom, aryl group, or heteroaryl group) and (Ar')s may be the same or different.)

As the above-mentioned synthesis process, specifically, a method described or cited in Faming Zhuanli Shenqing Gongkai Shuomingshu, 1382687, 04 Dec. 2002; Journal of Organic Chemistry, 68(12), 4855-4861, 2003; Green Chemistry, 4(4), 339-343, 2002; Chinese Journal of Chemistry, 20(11), 1334-1339, 2002; Synthetic Communications, 30(6), 1017-1022, 2000; Chemistry Letters, (7), 545-546, 1999; Mendeleev Communications, (5), 166-167, 1994; Journal of Heterocyclic Chemistry, 25(3), 767-770, 1988; or Journal of Organic Chemistry, 52(16), 3674-3680, 1987 can be used.

2> Process for Synthesizing from a Triazine trihalogenide

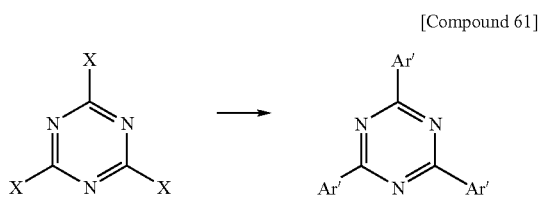

[Compound 61]

In the formula, X denotes any one of fluorine, chlorine, bromine, and iodine, and Ar denotes an arylene group, heteroarylene group, or unsaturated hydrocarbon group which may have an optional substituent (e.g., a halogen atom, aryl group, or heteroaryl group) and (Ar)s may be the same or different from each other.

In the above-mentioned processes, specifically, when X is chlorine, bromine, or iodine, a synthesis process described or cited in Journal of Organic Chemistry 68(9), 3367-3379, 2003; Journal of Organic Chemistry, 67(24), 8424-8429, 2002; Inorganic Chemistry 41(9), 2543-2547, 2002; Synthetic Metals, 122(3), 485-493, 2001; Organic Letters, 3(15), 2419-2421, 2001; U.S. Pat. No. 5,726,310, 10 Mar. 1998; Tetrahedron Letters, 38(46), 8017-8020, 1997; Eur. Pat. Appl., 779280, 18 Jun. 1997; Mendeleev Communications, (5), 166-167, 1994; or U.S. Pat. No. 4,826,978, 02 May 1989 can be used.

When X is fluorine, a synthesis process described or cited in Chemistry of Materials, 16(1), 185-194, 2004 can be used.

3> Other Synthesis Process

Further, synthesis processes described or cited in Journal of Organic Chemistry, 68(12), 4855-4861, 2003; European Journal of Organic Chemistry, (10), 1948-1953, 2003; Tetrahedron, 56(37), 7153-7161, 2000; Journal of the Indian Chemical Society, 73(6), 283-284, 1996; Eur. Pat. Appl. 649841, 26 Apr. 1995; Archiv der Pharmazie (Weinheim, Germany), 327(6), 389-391, 1994; Izvestiya Natsional'noi Akademii Nauk Respubliki Kazakhstan, Seriya Khimicheskaya, (2), 13-20, 1993; Eur. Pat. Appl. 497734, 05 Aug. 1992; Heterocycles, 34(2), 341-347, 1992; Sibirskii Khimicheskii Zhurnal, (4), 96-98, 1991; Bulletin of the Chemical Society of Japan, 62(10), 3171-3176, 1989; Journal of the Chemical Society, Perkin Transactions 2: Physical Organic Chemistry (1972-1999), (2), 117-122, 1988; Zeitschrift fuer Chemie, 26(8), 295-297, 1986; Khimiya Geterotsiklicheskikh Soedinenii, (1), 107-113, 1986; Synthesis, (1), 95-98, 1985; Journal of Heterocyclic Chemistry, 18(6), 1197-1201, 1981; Tetrahedron Letters, (43), 4193-4196, 1979; and Ber., 96, 1213-1217, 1963 can be used.

In addition, synthesis processes described or cited in "Heterokan No Kagaku—Iyakuhin No Kiso (Chemistry of Heterocyclic Compounds—Basics of Medicine" (2002, Kunieda, et al., Kagaku-Dojin), "Heterocyclic Chemistry" (4th ed., 2000, J. A. Joule and K. Mills, Blackwell Science Co.), "Shinpen Heterokan Kagobutsu Kiso-hen, Oyo-hen (New Heterocyclic Compounds, Basics and Advanced)" (2004, Nakayama, et al., Kodansya), and "Boruharuto/Syoa GendaiYuki Kagaku, Ge (Vollhardt & Schore Organic Chemistry II" (2004, K. P. C. Vollhardt, Kagaku-Dojin)" (2004, K. P. C. Vollhardt, Kagaku-Dojin) can be employed.

(4) In a process for introducing an N-carbazolyl group, for example, the following processes a) to c) can be employed as a process for introducing a carbazolyl group in the last step of the synthesis.

a) A little excessive amount (about 0.7 to 1.5 times equivalents to a halogen atom of a halide described below) of a halogenated aromatic boron compound such as fluorophenylboronic acid, difluorophenylboronic acid, fluorobiphenylboronate ester, or pentafluorophenylboronic acid and a 2- or 3-substituted aromatic halide such as dibromofluorobenzene, diiodobenzene, tribromobenzene, trichlorotriazine, or diiodobiphenyl are heated under reflux in the presence of a palladium catalyst (about 0.1 to 10 mol %) such as tetrakis(triphenylphosphine)palladium and a base (about 2 to 10 times equivalents to a halogen atom of the halide described above) such as cesium carbonate, potassium phosphate, or sodium carbonate in a solvent of toluene-ethanol, toluene-water, tetrahydrofuran, dioxane, dimethoxyethane, N,N-dimethylformamide, or a solvent mixture thereof (about 1 to 1000 mmole % as the above-mentioned boronic acid content)

under inert gas atmosphere for about 5 to 24 hr to form a fundamental skeleton having a fluorine atom as a substituent.

Then, a substituted or unsubstituted carbazole (about 1.1 to 10 equivalents to the fluorine atom of the fundamental skeleton having a fluorine atom) is reacted with a strong base (about 0.9 to 2 equivalents to hydrogen on N atom of an azole compound described below) such as sodium hydride, tert-butoxypotassium, or n-butyllithium under dry gas atmosphere and/or inert gas atmosphere in a solvent such as tetrahydrofuran, dioxane, ether, or N,N-dimethylformamide at a temperature range of −78 to +60° C. under stirring for 0.1 to 60 hr, and the reaction product is mixed with a solution of tetrahydrofuran, dioxane, ether, or N,N-dimethylformamide containing the above-prepared fundamental skeleton having a fluorine atom as a substituent, and the mixture is stirred under reflux while heating for 1 to 60 hr to obtain an organic compound according to the present invention.

b) A little excessive amount (about 1.1 to 1.5 times equivalents to a halogen atom of a halide described below) of a halogenated aromatic boronic acid such as bromophenylboronic acid, dibromophenylboronic acid, or dichlorophenylboronic acid and a 2- or 3-substituted halide such as diiodobenzene, bromodiiodobenzene, triiodobenzene, trichlorotriazine, or diiodobiphenyl are heated under reflux in the presence of a palladium catalyst (about 0.01 to 1 equivalent to a halogen atom of the above-mentioned halide) such as tetrakis(triphenylphosphine)palladium and a base (about 2 to 10 equivalents to a halogen atom of the halide described above) such as cesium carbonate, potassium phosphate, or sodium carbonate in a solvent such as toluene, ethanol, water, tetrahydrofuran, dioxane, dimethoxyethane, N,N-dimethylformamide, or a solvent mixture thereof (about 1 to 1000 mmole % as the above-mentioned boronic acid content) under inert gas atmosphere for about 5 to 24 hr to form a fundamental skeleton having a bromine atom and/or chlorine atom as a substituent.

Further, if necessary, a fundamental skeleton having an iodine group can be obtained from the resulting fundamental skeleton having a bromine group by converting the bromine group to the iodine group by stirring the compound having the fundamental skeleton in the presence of potassium iodide (1.5 to 10 equivalents to the bromine atom of the above-mentioned fundamental skeleton) and copper iodide (1 to 10 equivalents) in a solvent such as N,N-dimethylformamide (about 0.1 to 10 mol % as the halide content) at 100 to 300° C. for 0.5 to 60 hr.

Then, an organic compound according to the present invention can be obtained by treating the fundamental skeleton having a bromine atom and/or a chlorine atom as a substituent and carbazole (about 1.0 to 100 equivalents to the bromine atom and/or chlorine atom of the above-mentioned fundamental skeleton having a bromine atom and/or a chlorine atom as a substituent) as in the following (1) or (2):

(1) mixing the both in the presence of a copper catalyst (about 1 to 5 equivalents to the bromine atom and/or chlorine atom of the above-mentioned fundamental skeleton having a bromine atom and/or a chlorine atom as a substituent) such as copper powder, copper wire, copper halide (CuX$^r$ (X$^r$=Cl, Br, I)), or copper oxide (CuO), under inert gas flow in the absence of solvents or in the presence of a solvent (about 0.1 to 2 liters to 1 mole of the fundamental skeleton) such as tetraglyme or polyethylene glycol at a temperature range of 20 to 300° C. for 1 to 60 hr; or (2) mixing the both in the presence of a combination of a divalent palladium catalyst such as Pd$_2$(dba)$_3$ (Pd=palladium, dba=dibenzylideneacetone), Pd(dba)$_2$, or palladium acetate and a ligand such as BINAP (2,2'-bis(diphenylphosphino-1, 1'-binaphthyl), tri(tert-butyl)phosphine, triphenylphosphine, 1,2-bis(diphenylphosphino)ethane, 1,3-bis(diphenylphosphino)propane, 1,3-bis(diphenylphosphino)butane, or dppf (1,1'-bis(diphenylphosphino)ferrocene) or in the presence of a catalyst (usually, about 0.01 to 1 equivalent to the bromine atom and/or chlorine atom of the above-mentioned fundamental skeleton having a bromine atom and/or a chlorine atom as a substituent) of a nonvalent palladium complex such as Pd(PPh)$_4$ (Ph=phenyl) or a palladium chloride complex such as PdCl$_2$(dppf)$_2$ and, if necessary, a strong base (usually, 1.1 to 10 equivalents to 1 equivalent of hydrogen halide which may be generated depending on the reaction) such as tert-butoxypotassium, tert-butoxysodium, potassium carbonate, or triethylamine, and further, if necessary, in the coexistence of a copper catalyst (usually, 1 to 10 equivalents to 1 equivalent of hydrogen halide which may be generated depending on the reaction) such as copper iodide in a solvent (about 0.1 to 100 mmole % of the fundamental skeleton having a bromine atom and/or chlorine atom as a substituent) such as tetrahydrofuran, dioxane, dimethoxyethane, N,N-dimethylformamide, dimethylsulfoxide, xylene, toluene, or triethylamine at 30 to 200° C. for 1 to 60 hr.

c) In addition, the coupling may be conducted by a known method such as Grignard reaction, a method using zinc, or a method using tin. Examples of the catalyst include transition metal catalysts such as palladium, nickel, and copper. Generally, the catalyst is used in about 0.1 to 200 mole % to an intermediate having a carbazole ring. In addition, examples of the basic material include potassium carbonate, calcium carbonate, potassium phosphate, cesium carbonate, and tert-butoxysodium. Generally, the basic material is used in 50 to 1000 mole % to an intermediate having a carbazole ring. The reaction temperature is generally 0° C. or more, preferably 50° C. or more, but not more than 300° C., preferably not more than 200° C. Examples of the solvent used for the reaction include aromatic solvents such as toluene, xylene, and nitrobenzene and ether solvents such as tetrahydrofuran, ethyleneglycol dimethylether, and tetraglyme.

(5) As a method for introducing 2- to 8-carbazolyl group, a coupling reaction of a carbazole having a halogen atom such as chlorine, bromine, or iodine at a position at which the linking group Z is linked and an aryl borate, or a coupling reaction of an aryl halide and a carbazolyl borate can be used. Specifically, known coupling methods (linking (coupling)) reaction among rings described or cited in "Palladium in Heterocyclic Chemistry: A guide for the Synthetic Chemist", (2nd ed., 2002, Jie Jack Li and Gordon W. Gribble, Pergamon Co.), "Senikinzoku ga Hiraku Yuki Gosei, Sono Tasaina Hannoukeisiki to Saishin no Seika (Organic synthesis using transition metal, the various patterns of reaction and the latest developments)" (1997, Jiro TSUJI, Kagaku-Dojin), or "Boruharuto/Syoa Gendai Yuki Kagaku, Ge (Vollhardt & Schore Organic Chemistry II" (2004, K. P. C. Vollhardt, Kagaku-Dojin)) can be used.

(6) Furthermore, in addition to the above-mentioned synthesis processes, a linking group for linking Cz group in the above-mentioned Formula (I) to a pyridine ring in Formula (II-1), a pyrazine ring in Formula (II-2), a pyrimidine ring in Formula (II-3), or a triazine ring in Formula (II-4) (namely, -G-Q-(A$^1$ ring)-Z—) may be formed, according to need, by a known coupling process (linking (coupling)) reaction among rings described or cited in "Palladium in Heterocyclic Chemistry: A guide for the Synthetic Chemist", (2nd ed., 2002, Jie Jack Li and Gordon W. Gribble, Pergamon Co.), "Senikinzoku ga Hiraku Yuki Gosei, Sono Tasaina Hannoukeisiki to Saishin no Seika (Organic synthesis using transition metal, the various patterns of reaction and the latest developments)"

(1997, Jiro TSUJI, Kagaku-Dojin), or "Boruharuto/Syoa GendaiYuki Kagaku, Ge (Vollhardt & Schore Organic Chemistry II" (2004, K. P. C. Vollhardt, Kagaku-Dojin)).

(7) The purification of the resulting compound can be conducted by known technique such as methods described in "Bunriseiseigizyutsu Handbook (Handbook of separation and purification)" (1993, The Chemical Society of Japan), "Kagakuhenkanhoniyoru Biryoseibun oyobi Nanseiseibushitsu no Kodobunri (Chemical conversion for high separation of minor components or substances which cannot be readily purified)" (1988, I.P.C. (Industrial Publishing & Consulting) Inc.), or the section "Bunri to Seisei (Separation and Purification)" of "Jikken Kagaku Koza (4th ed.) 1 (Experimental Chemistry Series No. 1)" (1990, The Chemical Society of Japan). Specifically, the purification is carried out by extraction (including suspension washing, boiling washing, ultrasonic cleaning, and acid/base washing), adsorption, occlusion, fusion, crystallization (including recrystallization and reprecipitation from a solvent), distillation (atmospheric distillation and vacuum distillation), evaporation, sublimation (atmospheric sublimation and vacuum sublimation), ion-exchange, dialysis, filtration, ultrafiltration, reverse osmosis, pressure permeation, zone melting, electrophoresis, centrifugation, flotation separation, precipitation separation, magnetic separation, and various types of chromatography (shape classification: column, paper, thin-layer, and capillary; mobile-phase classification: gas, liquid, micelle, and supercritical fluid; separation mechanism: adsorption, distribution, ion-exchange, molecular sieve, chelate, gel-filtration, exclusion, and affinity).

(8) The confirmation of products and analysis of purity can be carried out by gas chromatography (GC), high-performance liquid chromatography (HPLC), rapid amino acid analysis (AAA), capillary electrophoresis (CE), size-exclusion chromatography (SEC), gel permeation chromatography (GPC), cross-fractionation chromatography (CFC) mass spectrometry (MS, LC/MS, GC/MS, MS/MS), nuclear magnetic resonance (NMR ($^1$HNMR, $^{13}$CNMR)), Fourier transform infrared spectroscopy (FT-IR), ultraviolet, visible, or near-infrared spectroscopy (UV, VIS, NIR), electron spin resonance (ESR), transmission electron microscopy (TEM-EDX) electron-probe microanalysis (EPMA), metallic elemental analysis (ion chromatography, inductively coupled plasma-atomic emission spectrometry (ICP-AES) atomic absorption spectrometry (AAS) X-ray fluorescence spectrometry (XRF)), non-metallic elemental analysis, or trace analysis (ICP-MS, GF-AAS, GD-MS), according to need.

[Charge-Transporting Material]

The organic compound according to the present invention can be used as a charge-transporting material.

The charge-transporting material according to the present invention does not have any limitation as long as the material contains an organic compound according to the present invention. However, generally, the charge-transporting material according to the present invention preferably consists of an organic compound according to the present invention.

[Organic Electroluminescent Device]

Next, an organic electroluminescent device according to the present invention using the above-described organic compound of the present invention will be described.

An organic electroluminescent device according to the present invention includes an anode, a cathode, and an organic light-emitting layer disposed between these electrodes on a substrate. The organic electroluminescent device has a layer containing an organic compound according to the present invention. The organic compound according to the present invention is preferably contained in the organic light-emitting layer. Particularly preferably, the organic light-emitting layer contains the organic compound according to the present invention as a host material, and the host material is doped with an organometallic complex.

When the organic compound according to the present invention is thus used as a host material of the organic light-emitting layer of an organic electroluminescent device of the present invention, the organic compound may be a single compound or a combination of two or more compounds.

An exemplary structure of the organic electroluminescent device according to the present invention will now be described with reference to the drawings, but the structure of the organic electroluminescent device according to the present invention is not limited to those shown in the drawings.

FIGS. 1 to 4 are cross-sectional views illustrating structure examples of organic electroluminescent devices according to the present invention. Reference numeral 1 denotes a substrate, reference numeral 2 denotes an anode, reference numeral 3 denotes a hole injection layer (anode buffer layer), reference numeral 4 denotes a hole transport layer, reference numeral 5 denotes a light-emitting layer, reference numeral 6 denotes a hole blocking layer, reference numeral 7 denotes an electron transport layer, and reference numeral 8 denotes a cathode.

[Substrate]

The substrate 1 is a base material of an organic electroluminescent device and is a quartz or glass plate, a metal plate or sheet, or a plastic film or sheet. In particular, glass plates and transparent plastic plates or films, such as polyester, polymethacrylate, polycarbonate, or polysulfone, are preferable. When a plastic substrate is employed, the gas-barrier property is important. When the gas barrier property of the substrate is too small, the organic electroluminescent device may be deteriorated by air passing through the substrate. This is disadvantageous. Therefore, as one favorable method, a dense silicon oxide film is preferably formed on at least one surface of the plastic substrate in order to retain a proper gas barrier property.

[Anode]

On the substrate 1, an anode 2 is disposed. The anode 2 has a function of injecting holes to a hole transport layer 4. The anode 2 is usually composed of a metal such as aluminum, gold, silver, nickel, palladium, or platinum; a metal oxide such as an indium tin oxide; a metal halide such as copper iodide; carbon black; or a conductive polymer such as poly (3-methylthiophene), polypyrrole, or polyaniline. The anode 2 is typically formed by a sputtering method or a vacuum deposition method. In addition, when the anode 2 is formed of microparticles of a metal such as silver, microparticles of copper iodide, carbon black, conductive metal oxide microparticles, or conductive polymer fine powder, the anode 2 may be formed by dispersing the particles in an appropriate binder resin solution and applying the solution on the substrate 1. Further, when the anode 2 is formed of a conductive polymer, the anode 2 may be formed by directly forming a polymerized thin film on the substrate 1 by electrolytic polymerization or by applying the conductive polymer on the substrate 1 (Appl. Phys. Lett., vol. 60, 2711, 1992).

The anode 2 usually has a single layer structure, but may have a laminated structure made of a plurality of materials, according to need.

The thickness of the anode 2 varies according to required transparency. When transparency is required, the transmissivity of visible light is usually 60% or more, preferably 80% or more. In such a case, the thickness of the anode is usually 5 nm or more, preferably 10 nm or more and usually 1000 nm or less, preferably about 500 nm or less. When transparency is not required, the thickness of the anode 2 does not have any limitation. Further, the anode may be formed of a metal so as to also function as the substrate 1, according to need.

[Hole Transport Layer]

In the device having a structure shown in FIG. 1, a hole transport layer 4 is disposed on the anode 2. The material for the hole transport layer is required to have a high efficiency of introducing holes from the anode 2 and to efficiently transport the injected holes. Therefore, the material is required to have low ionization potential, high transmissivity of visible light, high hole mobility, and excellent stability and also required to hardly generate impurities which become traps during manufacturing or in use. Furthermore, the hole transport layer 4 is required not to quench light from the light-emitting layer 5 and not to decrease efficiency by the formation of exciplex with the light-emitting layer 5 due to the contact of the hole transport layer 4 with the light-emitting layer 5. In addition to the above-mentioned generic requirements, the device is required to have heat resistance when the device is applied to a car-mounted display device. Therefore, a material having a glass-transition temperature of 85° C. or more is preferable.

Examples of the hole-transporting material, as in hole-transporting materials used as host materials of the light-emitting layer 5, include aromatic diamines containing two or more tertiary amines and having two or more condensed aromatic rings substituted to nitrogen atoms, represented by 4,4'-bis[N-(1-naphthyl)-N-phenylamine]biphenyl (Japanese Unexamined Patent Application Publication No. 5-234681), aromatic amine compounds having a starburst structure, such as 4,4',4''-tris(1-naphtyhlphenylamino)triphenylamine (J. Lumin. vol. 72-74, 985, 1997), aromatic amine compounds including a tetramer of triphenylamine (Chem. Commun. P. 2175, 1996), spiro compounds such as 2,2',7,7'-tetrakis-(diphenylamino)-9,9'-spirobifluorene (Synth. Metals, vol. 91, p. 209, 1997), and carbazole derivatives such as 4,4'-N,N'-dicarbazole-biphenyl. These compounds may be used alone or as a mixture thereof, according to need.

In addition to the above-mentioned compounds, polymer materials such as polyvinyl carbazoles, polyvinyl triphenylamines (Japanese Unexamined Patent Application Publication No. 7-53953), and polyarylene ether sulfones containing tetraphenylbenzidine (Polym. Adv. Tech. vol. 7, p. 33, 1996) may be used as a material for the hole transport layer 4.

The hole transport layer 4 may be formed by a usual coating method such as spraying, printing, spin coating, dip coating, or die coating; any method of various types of printing such as ink-jet printing and screen printing; or dry film-forming such as a vacuum deposition method.

When a coating method is employed, a coating solution is prepared by, according to need, adding an additive such as a binder resin or coating property-improving agent which does not trap holes to one or more hole-transporting materials and dissolving the resulting mixture in an appropriate solvent; and a hole transport layer 4 is formed by coating the coating solution to the anode 2 by a method such as spin coating. Examples of the binder resin include polycarbonates, polyarylates, and polyesters. Hole mobility is decreased when the content of a binder resin is high. Therefore, a smaller amount of the binder resin is desirable. Usually, the content in a hole transport layer is preferably 50 wt % or less.

When a vacuum deposition method is employed, a hole-transporting material is put in a crucible placed in a vacuum chamber, the vacuum chamber is evacuated to about $10^{-4}$ Pa by an appropriate vacuum pump, and then the hole-transporting material is evaporated by heating the crucible. Consequently, a hole transport layer 4 is formed on anode 2 formed on the substrate 1 placed parallel to the crucible.

The thickness of the hole transport layer 4 is usually 5 nm or more, preferably 10 nm or more and usually 30 nm or less, preferably 100 nm or less. In order to uniformly form a thin film, a vacuum deposition method is generally employed.

[Light-Emitting Layer]

In the device shown in FIG. 1, a light-emitting layer 5 is formed on the hole transport layer 4. The light-emitting layer 5 is formed of a light-emitting material which exhibits strong luminescence by excitation due to recombination of holes and electrons between electrodes applied with an electric field. The holes are injected from the anode 2 and move in the hole transport layer 4. The electrons are injected from the cathode and move in a hole blocking layer 6. Generally, the light-emitting layer 5 contains a dopant material serving as a light-emitting material and a host material. In addition, in this description, materials, such as a dopant material and a host material, contained in a light-emitting layer are referred to as a light-emitting layer material.

The material used in the light-emitting layer 5 is required to be a compound which can be formed into a stable thin-film form, show high luminescence (fluorescence or phosphorescence) quantum yield in a solid state, and efficiently transport holes and/or electrons. Further, the material is required to be a compound which is electrochemically and/or chemically stable and hardly generates impurities become traps during manufacturing or in use.

Furthermore, in the present invention, as in a paragraph of hole blocking layer described below, a light-emitting material having a first oxidation potential lower than that of a hole-blocking material, which is obtained by a cyclic voltammetric method, in particular, a light-emitting material that satisfies the following expressions:

(oxidation potential of hole-blocking material)−(oxidation potential of light-emitting layer material)$\geq$0.1 V, and (reduction potential of hole-blocking material)$\geq$(reduction potential of light-emitting material) is preferable. However, in the above-mentioned expressions, when the light-emitting layer 5 contains a host material and a dopant material, the oxidation or reduction potential of a light-emitting layer material means the oxidation or reduction potential of the host material.

Examples of the material forming a light-emitting layer which satisfies the above-mentioned conditions and exhibits fluorescence include metal complexes such as aluminum 8-hydroxyquinoline complex (Japanese Unexamined Patent Application Publication No. 59-194393), metal complexes of 10-hydroxybenzo[h]quinoline (Japanese Unexamined Patent Application Publication No. 6-322362), bisstyrylarylene derivatives (Japanese Unexamined Patent Application Publication No. 2-247278), metal complexes of (2-hydroxyphenyl)benzothiazole, and silole derivatives.

These light-emitting layer materials are usually deposited on a hole transport layer by a vacuum deposition method. In addition, among the above-mentioned materials for a hole transport layer, aromatic amine compounds having a luminous property can be also used as light-emitting layer materials.

For the purpose of enhancing the luminous efficiency of the device and also changing the color of emitted color, for example, an aluminum 8-hydroxyquinoline complex is used as a host material and is doped with a laser fluorescent dye such as coumarin (J. Appl. Phys., vol. 65, p. 3610, 1989). This doping method may be applied also to the light-emitting layer 5. As the doping material, there may be used any fluorescent dye besides coumarin. Examples of the fluorescent dye which gives blue luminescence include perylene, pyrene, anthracene, coumarin, and derivative thereof. Examples of green fluorescent dye include quinacridone derivatives and coumarin derivatives. Examples of yellow fluorescent dye include rubrene and perimidone derivatives. Examples of red fluorescent dye include DCM compounds, benzopyrane derivatives, rhodamine derivatives, benzothioxanthene derivatives, and azabenzothioxanethene.

In addition to the above-mentioned doping fluorescent dyes, fluorescent dyes listed in "Laser Kenkyu (Study of Laser)", vol. 8, p. 694, p. 803, p. 958 (1980); vol. 9, p. 85 (1981) can be used as doping materials for light-emitting layer depending on the host material.

The amount of the above-mentioned fluorescent dye with which the host material is doped is preferably $10^{-3}$ wt % or more, preferably 0.1 wt % or more. In addition, the amount is preferably 10 wt % or less, more preferably 3 wt % or less. When the amount is lower the lower limit, the fluorescent dye may not enhance the luminous efficiency of the device. When the amount is higher than the upper limit, the concentration quenching may occur to decrease the luminous efficiency.

The organic compound according to the present invention, as described above, includes both a portion being mainly involved in hole transportation and a portion being mainly involved in electron transportation. Therefore, the organic compound has both excellent hole-transporting property and electron-transporting property and has excellent electrical oxidation/reduction durability and a high triplet excitation level. This organic compound is suitable as a host material of the organic light-emitting layer of an organic electroluminescent device. The organic light-emitting layer of an organic electroluminescent device of the present invention preferably includes an organic compound according to the present invention as the host material, and this host material is preferably doped with an organometallic complex suitable as a light-emitting material based on reasons described below.

A dopant material used in the light-emitting layer is preferably an organometallic complex containing a metal selected from Groups 7 to 11 of the periodic table. From the viewpoint of luminous efficiency, the T1 (triplet excitation level) of the metal complex is preferably higher than that of the organic compound according to the present invention used as a host material. In addition, since the light emission occurs in the dopant material, the dopant material is required to have chemical stability, such as oxidation and reduction.

The metal in the phosphorescent organometallic complex containing a metal selected from Groups 7 to 11 of the periodic table is preferably ruthenium, rhodium, palladium, silver, rhenium, osmium, iridium, platinum, or gold. These organometallic complexes are preferably compounds represented by the following general formula (VI-1) or (VI-2):

(VI-1)

wherein M denotes a metal, k denotes a valence of the metal, L and L' each denote a bidentate ligand, and j denotes 0, 1, or 2.

[Compound 62]

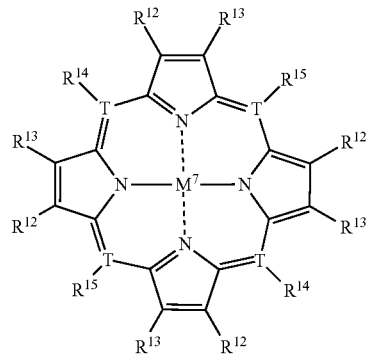
(VI-2)

wherein $M^7$ denotes a metal; T denotes carbon or nitrogen; when T is nitrogen, $R^{14}$ and $R^{15}$ are not present; when T is carbon, $R^{14}$ and $R^{15}$ each denote a hydrogen atom, halogen atom, alkyl group, aralkyl group, alkenyl group, cyano group, amino group, acyl group, alkoxycarbonyl group, carboxyl group, alkoxy group, alkylamino group, aralkylamino group, haloalkyl group, hydroxy group, aryloxy group, or an aromatic hydrocarbon or aromatic heterocyclic group which may have a substituent;

$R^{12}$ and $R^{13}$ each denote a hydrogen atom, halogen atom, alkyl group, aralkyl group, alkenyl group, cyano group, amino group, acyl group, alkoxycarbonyl group, carboxyl group, alkoxy group, alkylamino group, aralkylamino group, haloalkyl group, hydroxy group, aryloxy group, or an aromatic hydrocarbon or aromatic heterocyclic group which may have a substituent and $R^{12}$ and $R^{13}$ may form a ring by combining with each other.

Each of the bidentate ligands L and L' in general formula (VI-1) has a partial structure shown below:

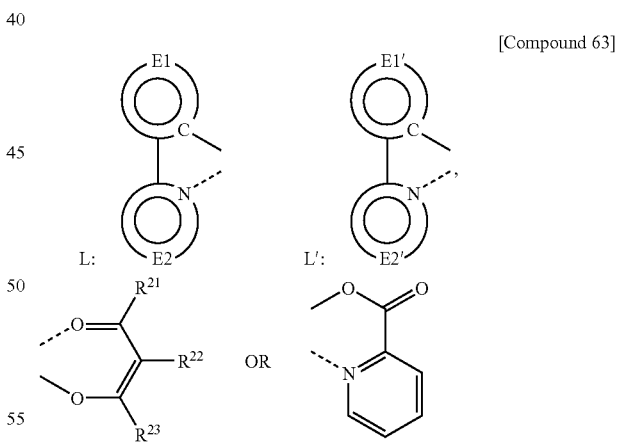

[Compound 63]

wherein E1 ring and E1' ring each independently denote an aromatic hydrocarbon group or an aromatic heterocyclic group and may each have a substituent; E2 ring and E2' ring each independently denote an aromatic heterocyclic group containing nitrogen and may each have a substituent; $R^{21}$, $R^{22}$, and $R^{23}$ each denote a hydrogen atom, alkyl group, alkenyl group, alkoxycarbonyl group, methoxy group, alkoxy group, aryloxy group, dialkylamino group, diarylamino group, carbazolyl group, acyl group, haloalkyl group, or cyano group.

The compounds represented by general formula (VI-1) are more preferably represented by the following general formula (VI-1a), (VI-1b), or (VI-1c):

[Compound 64]

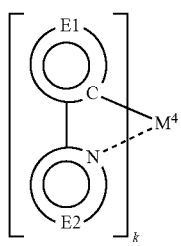

[Compound 64]

wherein $M^4$ denotes a metal; k denotes a valence of the metal; E1 ring denotes an aromatic hydrocarbon group which may have a substituent; and E2 ring denotes an aromatic hetrocyclic group containing nitrogen which may have a substituent;

[Compound 65]

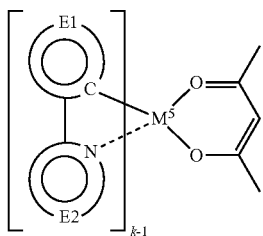

(VI-1b)

wherein $M^5$ denotes a metal; k denotes a valence of the metal; E1 ring denotes an aromatic hydrocarbon group or an aromatic heterocyclic group which may have a substituent; and E2 ring denotes an aromatic hetrocyclic group containing nitrogen which may have a substituent;

[Compound 66]

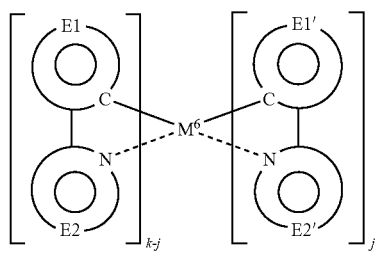

(VI-1 c)

wherein $M^6$ denotes a metal; k denotes a valence of the metal; j denotes 0, 1, or 2; E1 ring and E1' ring each independently denote an aromatic hydrocarbon group or an aromatic heterocyclic group which may have a substituent; and E2 ring and E2' ring each independently denote an aromatic hetrocyclic group containing nitrogen which may have a substituent.

Preferable examples of E1 ring and E1' ring of a compound represented by general formula (VI-1a), (VI-1b), or (VI-1c) include a phenyl group, a biphenyl group, a naphthyl group, an anthryl group, a thienyl group, a furyl group, a benzothienyl group, a benzofuryl group, a pyridyl group, a quinolyl group, an isoquinolyl group, and a carbazolyl group.

Preferable examples of E2 ring and E2' ring include a pyridyl group, a pyrimidyl group, a pyrazyl group, a triazyl group, a benzothiazole group, a benzoxazole group, a benzoimidazole group, a quinolyl group, an isoquinolyl group, a quinoxalyl group, and a phenanthrizyl group.

Examples of the substituent which may be added to the compound represented by general formula (VI-1a), (VI-1b), or (VI-1c) include halogen atoms such as a fluorine atom; alkyl groups having 1 to 6 carbon atoms such as a methyl group and an ethyl group; alkenyl groups having 2 to 6 carbon atoms such as a vinyl group; alkoxycarbonyl groups having 2 to 6 carbon atoms such as a methoxycarbonyl group and an ethoxycarbonyl group; alkoxy groups having 1 to 6 carbon atoms such as a methoxy group and an ethoxy group; aryloxy groups such as a phenoxy group and a benzyloxy group; dialkylamino groups such as a dimethylamino group and a diethylamino group; diarylamino groups such as a diphenylamino group; a carbazolyl group; acyl groups such as an acetyl group; haloalkyl groups such as a trifluoromethyl group; and a cyano group. These substituents may form a ring by combining with each other.

A condensed ring may be formed by combining a substituent of E1 ring and a substituent of E2 ring or a substituent of E1' ring and a substituent of E2' ring. An example such a condensed ring is a 7,8-benzoquinoline group.

More preferable examples of the substituents of E1 ring, E1' ring, E2 ring, and E2' ring include an alkyl group, an alkoxy group, an aromatic hydrocarbon group, a cyano group, a halogen atom, a haloalkyl group, a diarylamino group, and a carbazolyl group.

Preferable examples of $M^4$ and $M^5$ in formulae (VI-1a) and (VI-1b) include ruthenium, rhodium, palladium, silver, rhenium, osmium, iridium, platinum, and gold. Preferable examples of $M^7$ in formula (VI) include ruthenium, rhodium, palladium, silver, rhenium, osmium, iridium, platinum, and gold. Particularly preferable examples are divalent metals such as platinum and palladium.

Specific examples of organometallic complex represented by the above-mentioned general formulae (VI-1), (VI-1a), (VI-1b), and (VI-1c) will be shown below, but the organometallic complexes are not limited to them.

[Compound 67]

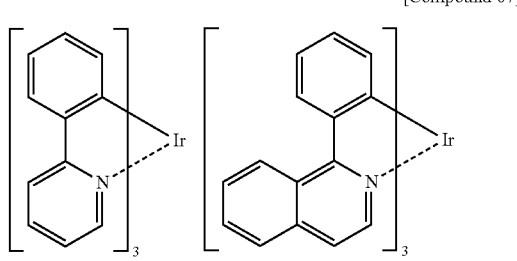

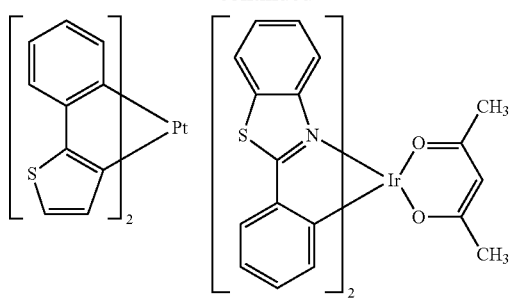
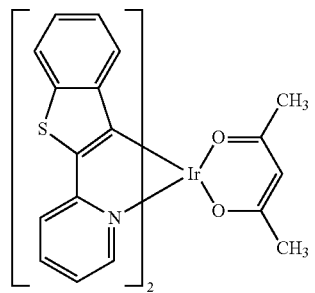
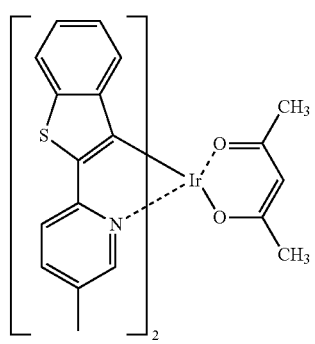
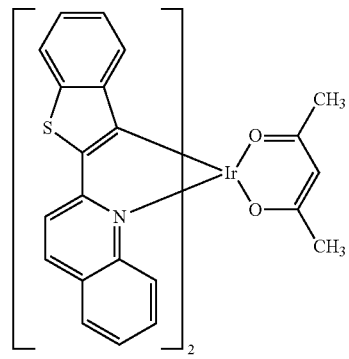
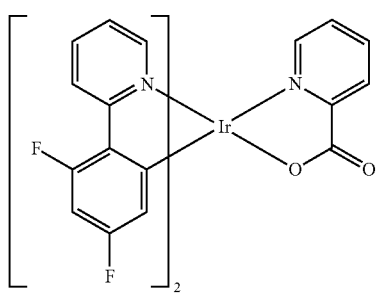
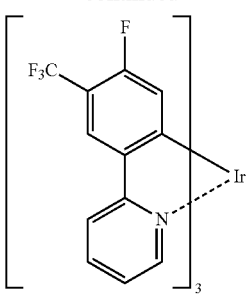
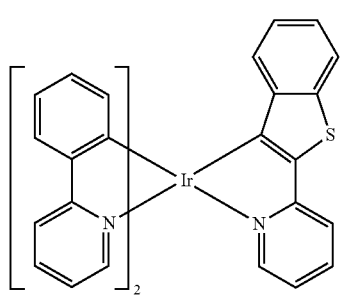
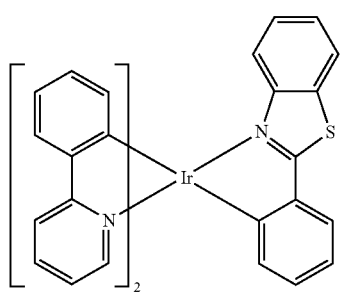
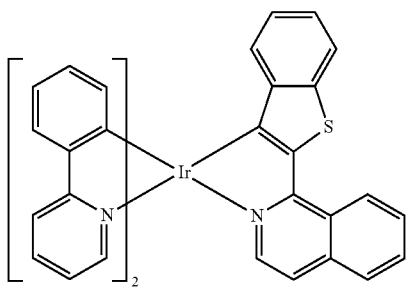
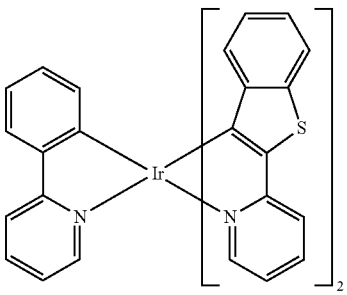

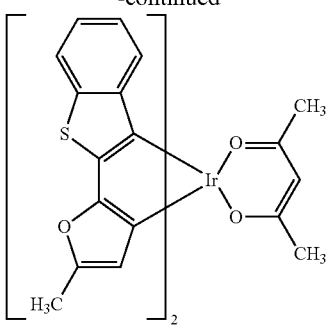
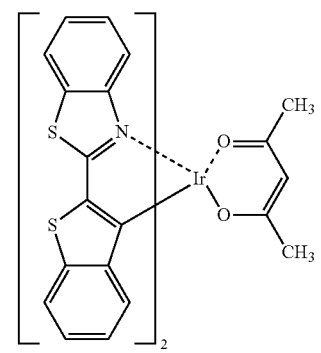
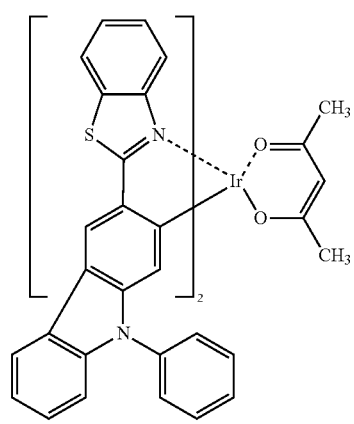
[Compound 68]
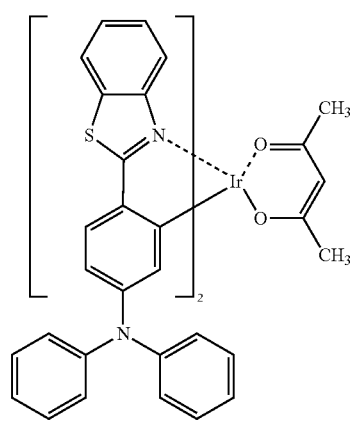
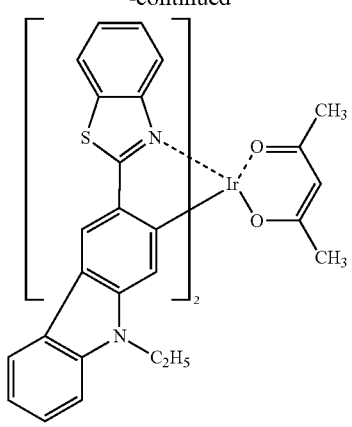
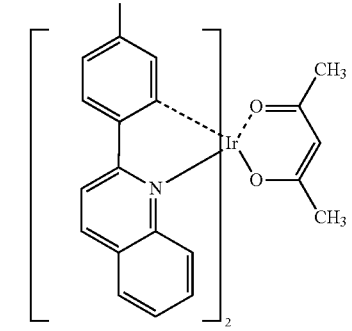
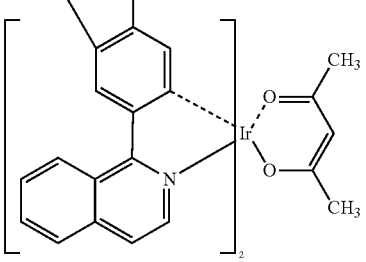
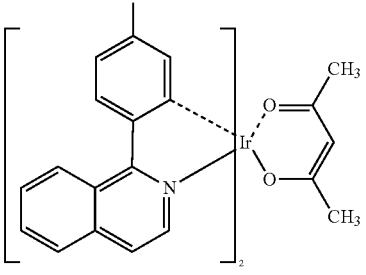

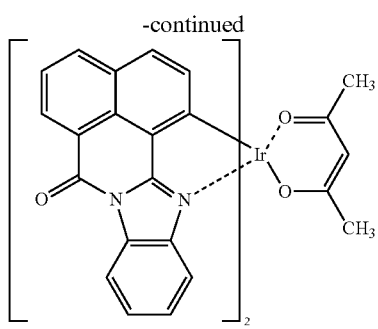

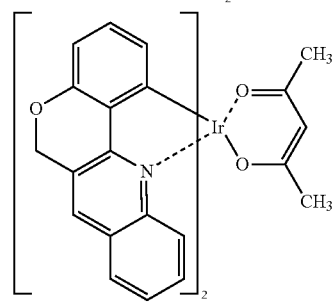

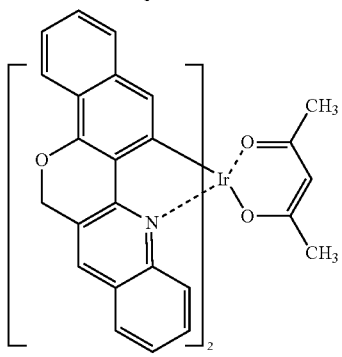

Among the organometallic complex represented by the above-mentioned general formulae (VI-1), (VI-1a), (VI-1b), and (VI-1c), a compound having a 2-arylpyridine ligand (2-arylpyridine, an optional substituent is combined therewith, or further an optional group is condensed therewith) is particularly preferable as the ligands L and/or L'.

Specific examples of organometallic complex represented by the above-mentioned general formula (VI-2) will be shown below, but the organometallic complexes are not limited to the following compounds. In the below examples, Me denotes a methyl group, and Et denotes an ethyl group.

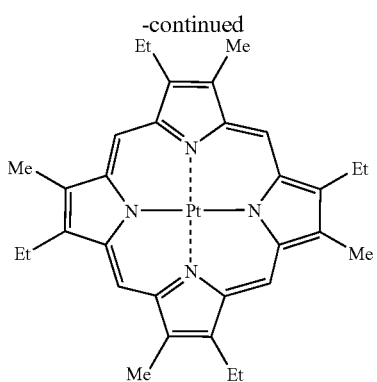

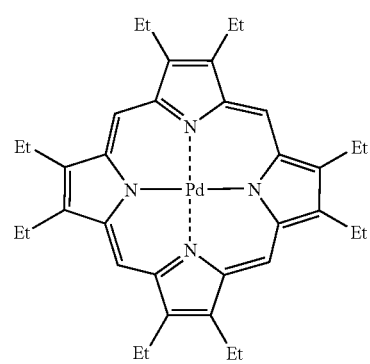

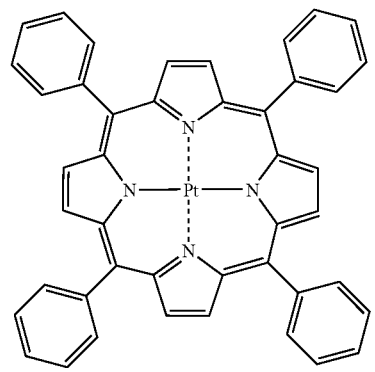

[Compound 69]

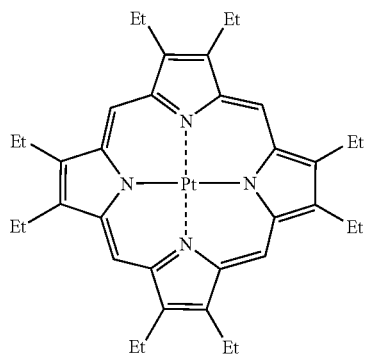

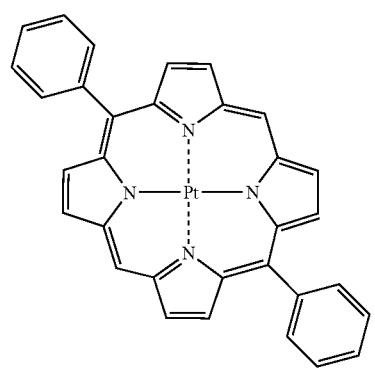

-continued

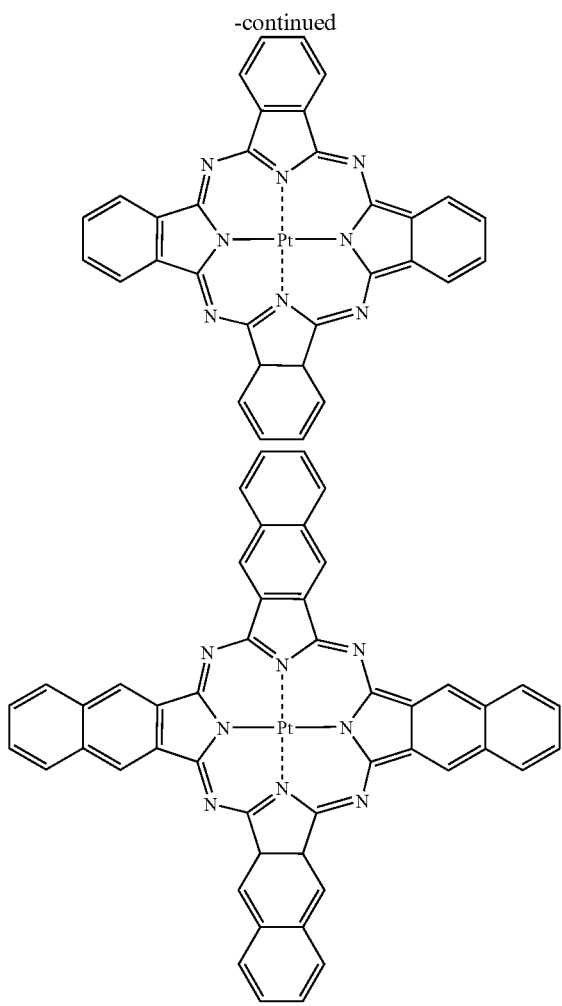

In addition, the following compound may be used as the phosphorescent organometallic complex containing a metal selected from Groups 7 to 11 of the periodic table.

[Compound 70]

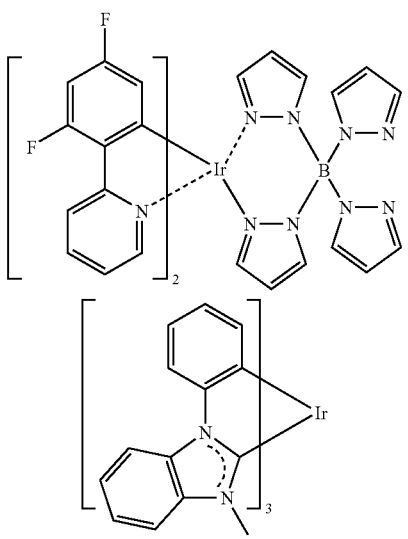

The molecular weight of the phosphorescent dopant material is usually 4000 or less, preferably 3000 or less, more preferably 2000 or less and is usually 200 or more, preferably 300 or more, more preferably 400 or more. When the molecular weight is higher than this upper limit, the sublimation property may be significantly deteriorated to cause a problem when a vapor deposition method is employed for fabricating an organic electroluminescent device, or the high purification of the material (namely, elimination of deterioration-causing materials) may become difficult by a decrease in solubility to an organic solvent or an increase in impurity content generated during a synthesis process.

When the molecular weight is lower than the lower limit, a significant deterioration in the heat resistance may be caused by decreases in the glass transition temperature, melting point, and vaporization temperature.

When two or more kinds of dopant materials are used, the oxidation potential of the hole-blocking material in a hole blocking layer is preferably higher than the highest oxidation potential in those of the plural kinds of dopant materials.

When an organometallic complex is used as a dopant material, the host material used in a light-emitting layer exhibiting phosphorescence may be one kind of organic compound or a mixture of two or more kinds of organic compounds of the present invention. In addition to the organic compound according to the present invention, one or more kinds of materials, such as materials (including aromatic amine compounds) described as host materials used in the light-emitting layer exhibiting phosphorescence, carbazole derivatives such as 4,4'-N,N'-dicarbazolebiphenyl (WO00/70655), tris(8-hydroxyquinoline)aluminum (U.S. Pat. No. 6,303,238), 2,2',2''-(1,3,5-benzenetriyl)tris[1-phenyl-1H-benzimidazole] (Appl. Phys. Lett. vol. 78, p. 1622, 2001), and polyvinylcarbazole (Japanese Unexamined Patent Application Publication No. 2001-257076), may be used. When the light-emitting layer contains a host material in addition to an organic compound according to the present invention, the content of the host material is preferably 50 wt % or less with respect to the organic compound according to the present invention.

The content of an organometallic complex contained as a dopant material in the light-emitting layer is preferably 0.1 wt % or more and 30 wt % or less. When the content is lower than this lower limit, the dopant material may not be involved in enhancement of luminous efficiency. When the content is higher than the upper limit, the concentration quenching may be induced by formation of a dimmer of the organometallic complex, resulting in a decrease in luminous efficiency.

There is a tendency in an element using known fluorescence (singlet) that it is preferable that the content of the dopant material in a light-emitting layer exhibiting phosphorescence be slightly higher than the content of fluorescent dye contained in the light-emitting layer. When an fluorescent dye is contained in an light-emitting layer together with a phosphorescent dopant material, the content of the fluorescent dye is preferably 0.05 wt % or more, more preferably 0.1 wt % or more. Further, the content is preferably 10 wt % or less, more preferably 3 wt % or less.

The thickness of the light-emitting layer 5 is usually 3 nm or more, preferably 5 nm and usually 200 nm or less, preferably 100 nm or less.

The light-emitting layer 5 can be formed by the same manner as in the hole transport layer 4.

A method for doping the organic compound according to the present invention used as the host material of a light-emitting layer with the above-described fluorescent dye and/or phosphorescent dye (phosphorescent dopant material) as the dopant material will now be described.

When coating is employed, a coating solution in which an organic compound according to the present invention, a dopant material, and, according to need, an additive such as a binder polymer which does not trap electrons nor quench light emission or a coating property-improving agent such as a leveling agent are added and dissolved is prepared. The coating solution is applied on the hole transport layer 4 by a method such as spin coating and is then dried to form a light-emitting layer 5. Examples of the binder polymer include polycarbonates, polyarylates, and polyesters. A large content of a binder polymer decreases hole/electron mobility. Therefore, a smaller content is preferable, and the content in a light-emitting layer is preferably 50 wt % or less.

When vapor deposition is employed, an organic compound according to the present invention and a dopant material are put in separate crucibles placed in a vacuum chamber, and the vacuum chamber is evacuated to about $10^{-4}$ Pa by an appropriate vacuum pump, and then evaporating the both by simultaneously heating the crucibles to form a layer on a substrate placed parallel to the crucibles. In addition, as another method, the above-mentioned materials are preliminarily mixed at a predetermined ratio and may be evaporated using a single crucible.

When the above-described dopant materials are each doped in the light-emitting layer 5, the dopant material is uniformly doped in the light-emitting layer in the thickness direction. However, there may be concentration distribution in the thickness direction. For example, a dopant material may be doped near the interface with the hole transport layer 4 or, inversely, near the interface with the hole blocking layer 6.

The light-emitting layer 5 can be formed by the same method as in the hole transport layer 4. Usually, a vacuum deposition method is employed.

The light-emitting layer 5 may contain ingredients other than the above-mentioned materials as long as the performance according to the present invention is retained.

[Hole Blocking Layer]

In the device shown in FIG. 1, the hole blocking layer 6 is disposed on the light-emitting layer 5 so as to be in contact with the interface of the cathode side of the light-emitting layer 5.

The hole blocking layer 6 is preferably formed of a compound which can prevent holes moving from the hole transport layer 4 from reaching the cathode 8 and can efficiently transport electrons injected from the cathode 8 toward the light-emitting layer 5. Therefore, the physical properties required to a material constituting the hole blocking layer 6 are high electron mobility and low hole mobility. The hole blocking layer 6 has a function to enhance luminous efficiency by trapping holes and electrons in the light-emitting layer 5.

The ionization potential of the hole blocking layer 6 provided to the organic electroluminescent element according to the present invention is preferably higher than that of the light-emitting layer 5 (ionization potential of a host material when the light-emitting layer 5 contains a host material and a dopant material) by 0.1 eV or more. The ionization potential is defined by energy necessary to release electrons existing in a HOMO (highest occupied molecular orbital) level to a vacuum level. The ionization potential may be directly defined by photoelectron spectroscopy or determined by compensating electrochemically measured oxidation potential with respect to a reference electrode. In the later method, for example, when a saturated calomel electrode (SCE) is used as the reference electrode, the ionization potential is defined by the following formula ("Molecular Semiconductors", Springer-Verlag, 1985, p. 98):

Ionization potential=Oxidation potential (vs. SCE)+ 4.3 eV.

Furthermore, electron affinity (EA) of the hole blocking layer 6 provided to the organic electroluminescent element of the present invention is preferably equivalent to or more than that of the light-emitting layer 5 (electron affinity of a host material when the light-emitting layer 5 contains a host material and a dopant material). The electron affinity is also defined by energy for stabilizing electrons existing in a vacuum level by falling to the LUMO (lowest unoccupied molecular orbital) of a substance using the vacuum level as the standard as in ionization potential. The electron affinity can be determined by subtracting an optical bandgap from the above-mentioned ionization potential or by electrochemical reduction potential according to the following formula:

Electron affinity=Reduction potential (vs. SCE)+4.3 eV.

Therefore, in the hole blocking layer 6 provided to the organic electroluminescent element of the present invention, the oxidation potential and the reduction potential can be defined as follows:

(Oxidation potential of hole blocking material)−(Oxidation potential of light-emitting layer material)≧0.1 V, and (Reduction potential of hole blocking material)≧(Reduction potential of light-emitting layer material).

Further, when the element has an electron transport layer 7 described below, the electron affinity of the hole blocking layer 6 is preferably equivalent to or less than that of the electron transport layer 7. Therefore, preferably, there is a relationship that (reduction potential of electron-transporting material)≧(reduction potential of hole-blocking material)≧(reduction potential of light-emitting layer material). When the electron-transporting material, the hole-blocking material, and the light-emitting layer material each consist of a plurality of components, the component with lowest reduction potential is used for comparison. In addition, when the light-emitting layer 5 contains a host material and a dopant material, the host material with the lowest reduction potential is used for comparison.

Preferable examples of the hole-blocking material satisfying such conditions include mixed ligand complexes represented by the following general formula (VII):

[Compound 71]

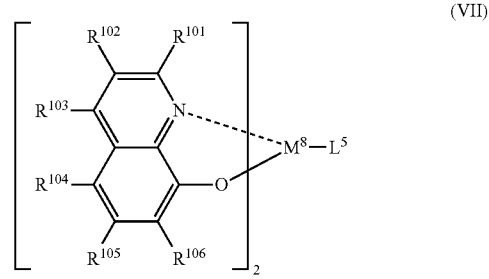

(VII)

wherein $R^{101}$ to $R^{106}$ each independently denote a hydrogen atom or an optional substituent; $M^8$ denotes a metal atom selected from aluminum, gallium, and indium; and $L^5$ is represented by any one of the following general formulae (VIIa), (VIIb), and (VIIc):

[Compound 72]

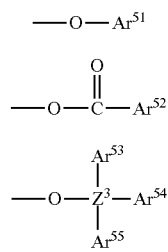

(VIIa)
(VIIb)
(VIIc)

wherein $Ar^{51}$ to $Ar^{55}$ each independently denote an aromatic hydrocarbon group which may have a substituent or an aromatic heterocyclic group which may have a substituent; and $Z^3$ denotes silicon or germanium.

In the above-mentioned general formula (VII), $R^{101}$ to $R^{106}$ each independently denote a hydrogen atom or an optional substituent, preferably, a hydrogen atom; a halogen atom such as chlorine and bromine; an alkyl group having 1 to 6 carbon atoms such as a methyl group and an ethyl group; an aralkyl group such as a benzyl group; an alkenyl group having 2 to 6 carbon atoms such as a vinyl group; a cyano group; an amino group; an acyl group; an alkoxy group having 1 to 6 carbon atoms such as a methoxy group and an ethoxy group; an alkoxycarbonyl group such as a methoxycarbonyl group and an ethoxycarbonyl group; a carboxyl group; an aryloxy group such as a phenoxy group and a benzyloxy group; a dialkylamino group such as a diethylamino group and a diisopropylamino group; a diaralkylamino group such as a dibenzylamino group and a diphenethylamino group; an α-haloalkyl group such as a trifluoromethyl group; a hydroxy group; an aromatic hydrocarbon group which may have a substituent such as a phenyl group and a naphthyl group; or an aromatic heterocyclic group which may have a substituent such as a thienyl group and a pyridyl group.

Examples of the substituent which the aromatic hydrocarbon group or the aromatic heterocyclic group may have include halogen atoms such as a fluorine atom; alkyl groups having 1 to 6 carbon atoms such as a methyl group and an ethyl group; alkenyl groups having 2 to 6 carbon atoms such as a vinyl group; alkoxycarbonyl groups having 2 to 6 carbon atoms such as a methoxycarbonyl group and an ethoxycarbonyl group; alkoxy groups having 1 to 6 carbon atoms such as a methoxy group and an ethoxy group; aryloxy groups such as a phenoxy group and a benzyloxy group; dialkylamino groups such as a dimethylamino group and a diethylamino group; acyl groups such as an acetyl group; haloalkyl groups such as a trifluoromethyl group; and cyano groups.

More preferably, $R^{101}$ to $R^{106}$ are each independently a hydrogen atom, an alkyl group, a halogen atom, or a cyano group. In addition, a cyano group is particularly preferable as $R^{104}$.

Specifically, $Ar^{51}$ to $Ar^{55}$ in the above-mentioned general formulae (VIIa), (VIIb), and (VIIc) are each independently an aromatic hydrocarbon group which may have a substituent, such as a phenyl group, a biphenyl group, and a naphthyl group, or an aromatic heterocyclic group, such as a thienyl group and a pyridyl group.

Preferable specific examples of the compound represented by the above-mentioned general formula (VII) are shown below, but not limited to them.

[Compound 73]

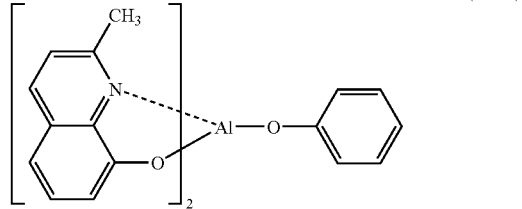

(HB-1)

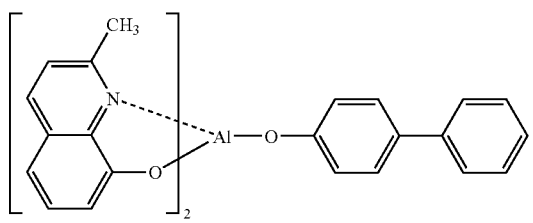

(HB-2)

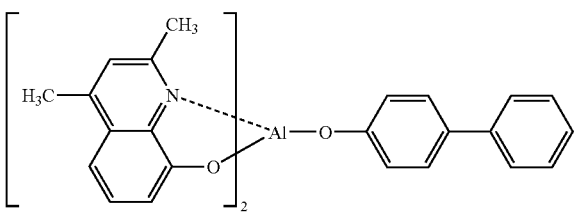

(HB-3)

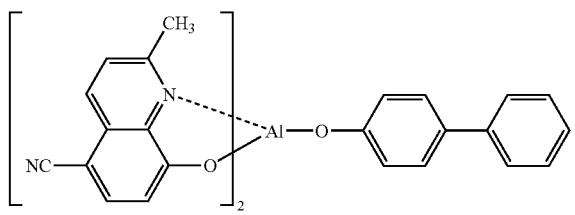

(HB-4)

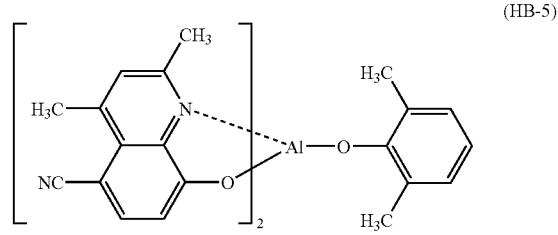

(HB-5)

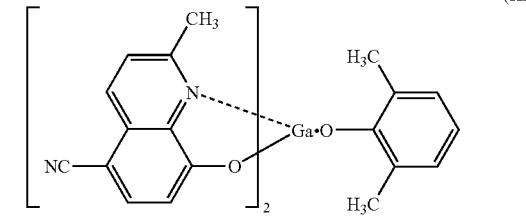

(HB-6)

(HB-7)
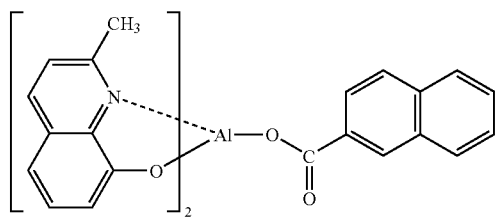
(HB-8)
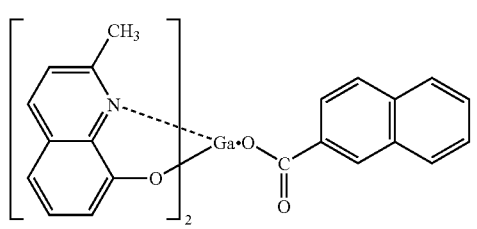
(HB-9)
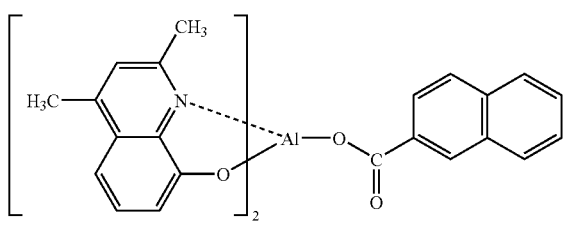
(HB-10)
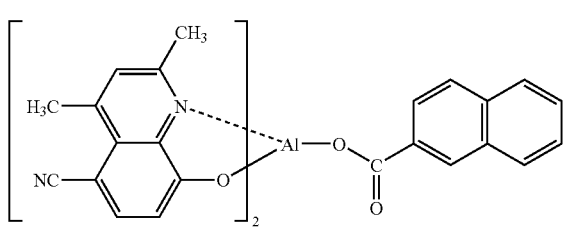
(HB-11)
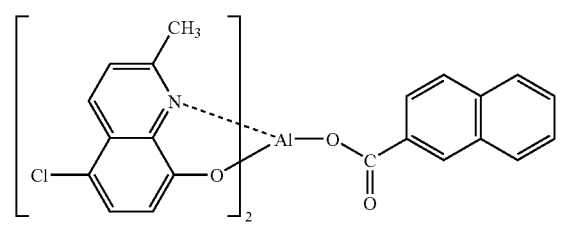
[Compound 74]
(HB-12)
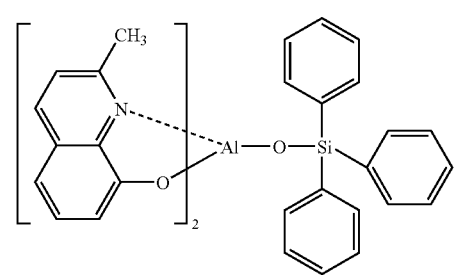
(HB-13)
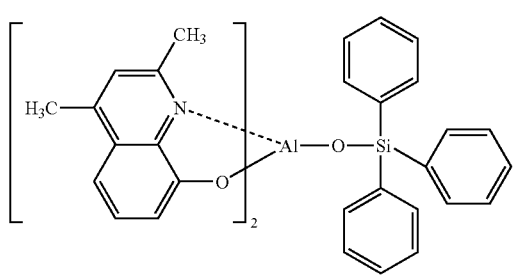
(HB-14)
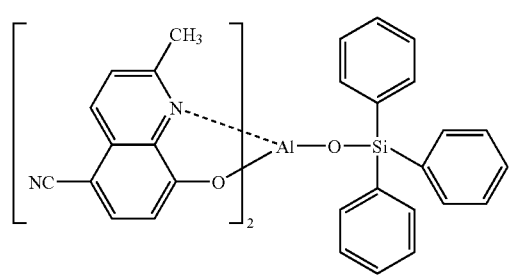
(HB-15)
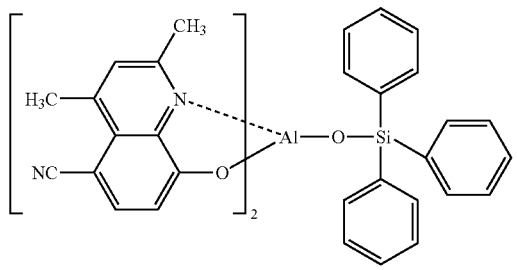
(HB-16)
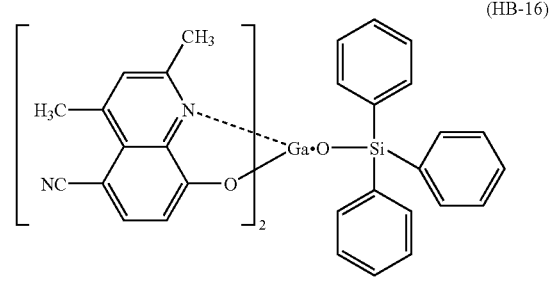
(HB-17)
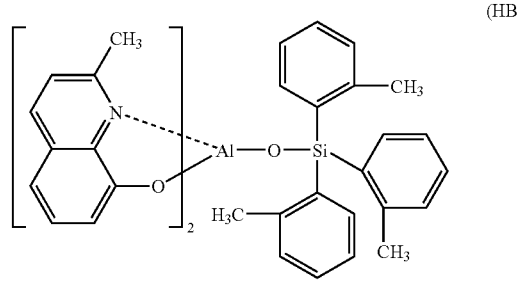

-continued (HB-18)

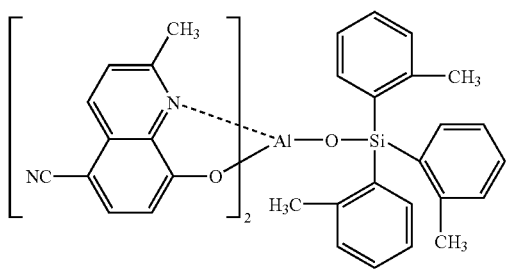

(HB-19)

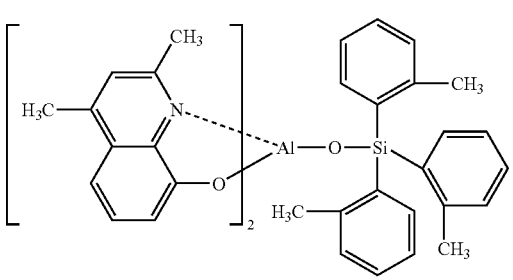

(HB-20)

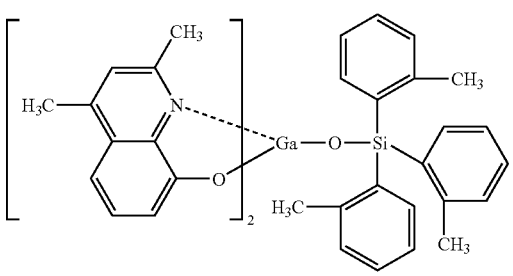

These compounds may be used alone or in a mixture of two or more thereof according to need in the hole blocking layer 6.

As a material as the hole-blocking material, in addition to the mixed ligand complexes represented by the above-mentioned general formula (VII), compounds having at least one 1,2,4-triazole ring residue represented by the following structural formula may be used.

[Compound 75]

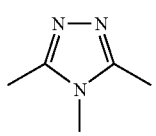

Specific examples of the compounds having at least one 1,2,4-triazole ring residue represented by the structural formula above are shown below, but not limited to them.

[Compound 76]

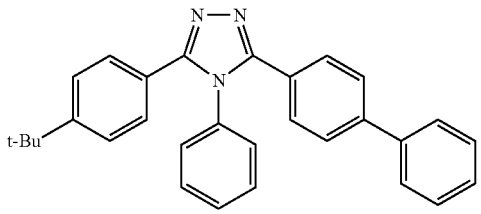

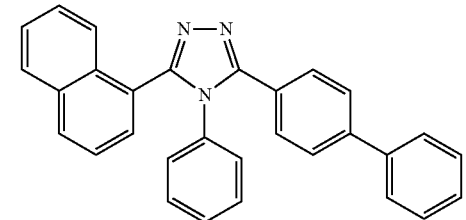

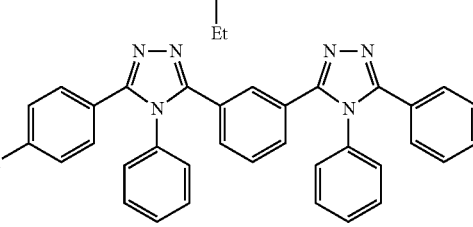

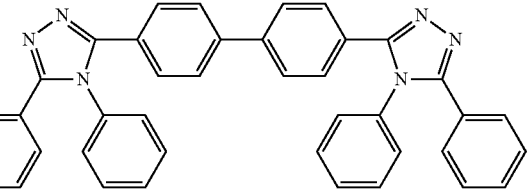

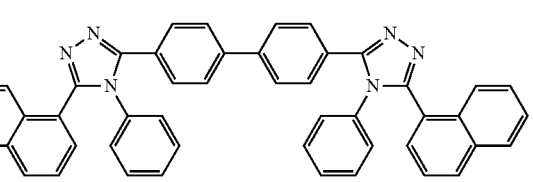

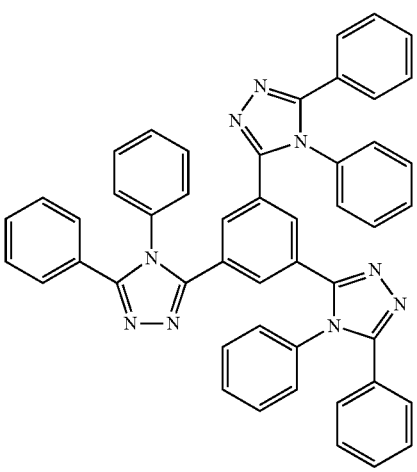

Examples of the hole-blocking material further include compounds having at least one phenanthroline ring represented by the following structural formula:

[Compound 77]

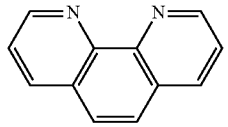

Specific examples of the compounds having at least one phenanthroline ring represented by the structural formula above are shown below, but not limited to them.

[Compound 78]

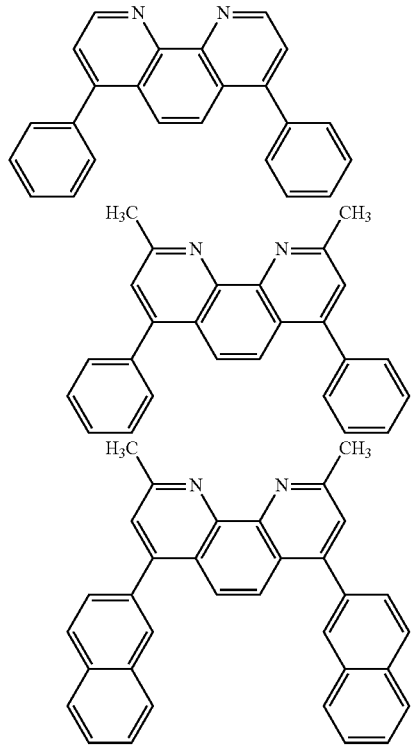

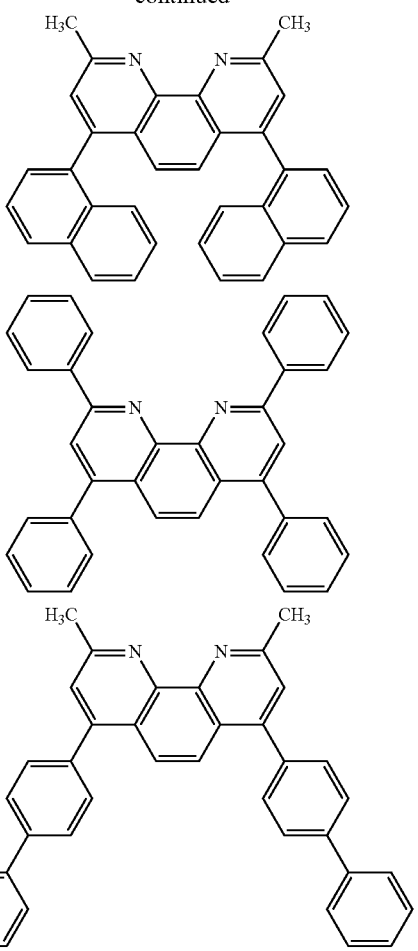

As the hole-blocking material, a compound containing a pyridine ring having substituents at 2,4,6-positions in one molecule is preferably used. The followings are specific examples.

[Compound 79]

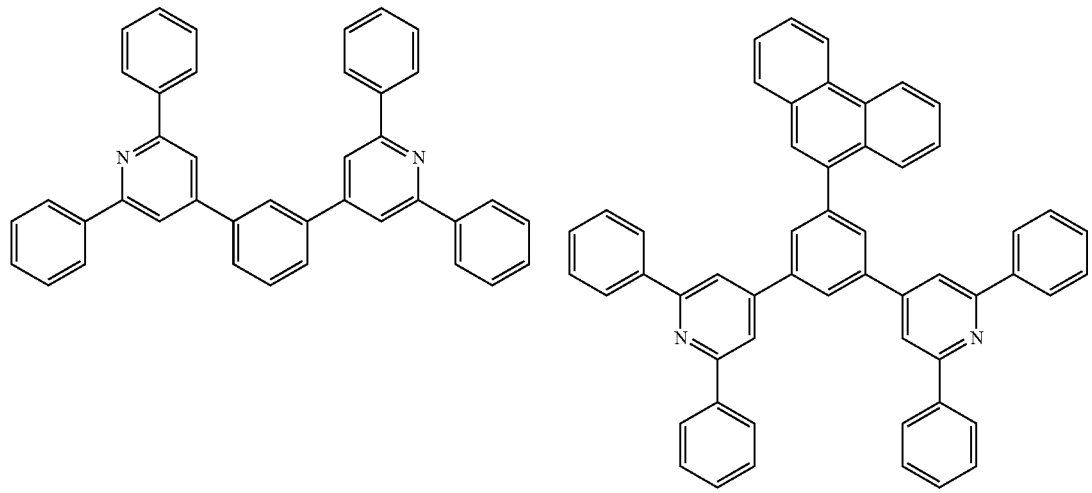

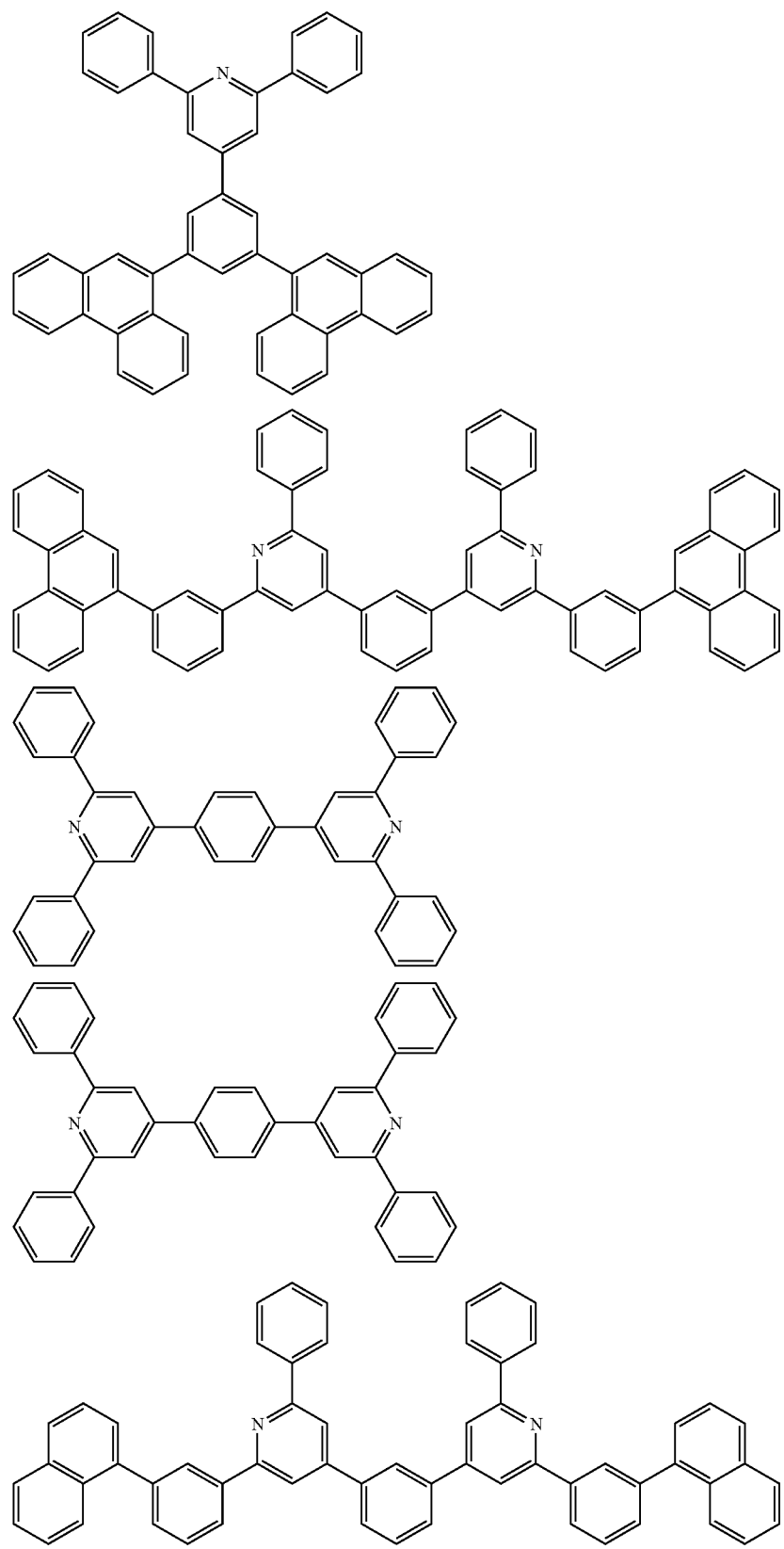

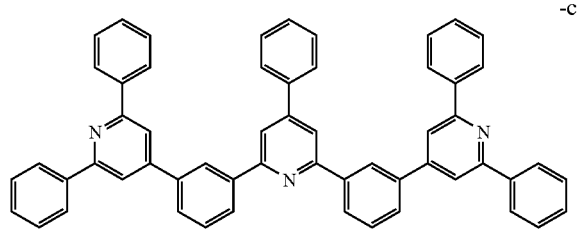
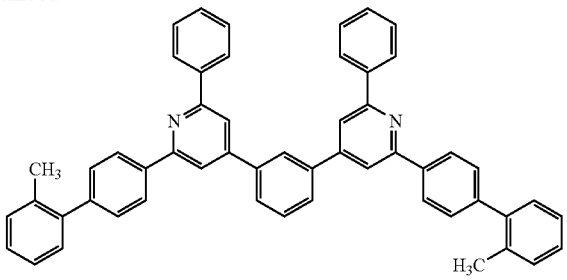
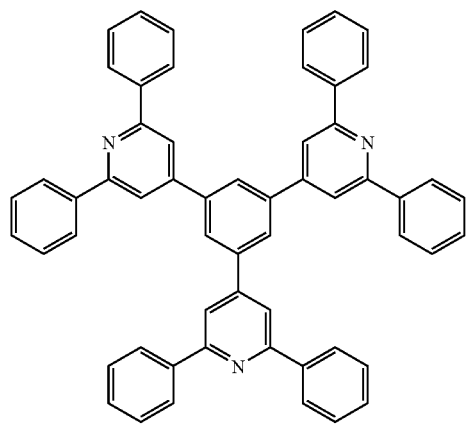

The thickness of the hole blocking layer 6 is usually 0.3 nm or more, preferably 0.5 nm or more and usually 100 nm or less, preferably 50 nm or less.

The hole blocking layer 6 can be formed by the same method as in hole transport layer 4. Usually, a vacuum deposition method is employed.

The organic compound used in the present invention is excellent as a host material of the light-emitting layer of an organic electroluminescent element and, as shown in Examples described below, a sufficiently favorable property can be obtained according to the present invention, even if a hole blocking layer is not provided.

[Cathode]

The cathode 8 has a function to inject electrons into the light-emitting layer 5 through the hole blocking layer 6. The material used in the cathode 8 may be the same as that used in the anode 2, but a metal having a low work function is preferable for efficiently injecting electrons. An appropriate metal such as tin, magnesium, indium, calcium, cesium, aluminum, and silver or an alloy thereof may be used. Specific examples of the cathode include low-work-function alloy electrodes such as a magnesium-silver alloy, a magnesium-indium alloy, and an aluminum-lithium alloy.

The thickness of the cathode 8 is usually the same as that of the anode 2.

In order to protect the cathode 8 made of a low-work-function metal, a metal layer which has a high-work-function and is stable to the air is laminated on the cathode. This increases the stability of an element. For achieving this purpose, a metal such as aluminum, silver, copper, nickel, chromium, gold, or platinum is used.

The efficiency of a device can be enhanced by disposing a ultrathin insulating film (0.1 to 5 nm) made of LiF, $MgF_2$, or $Li_2O$ at the interface between the cathode 8 and the light-emitting layer 5 or between the cathode 8 and an electron transport layer 7 described below (Appl. Phys. Lett., vol. 70, p. 152, 1977; Japanese Unexamined Patent Application Publication No. 10-74586; IEEE Trans. Electron. Devices, vol. 44, p. 1245, 1997).

[Electron Transport Layer]

Figure 2:
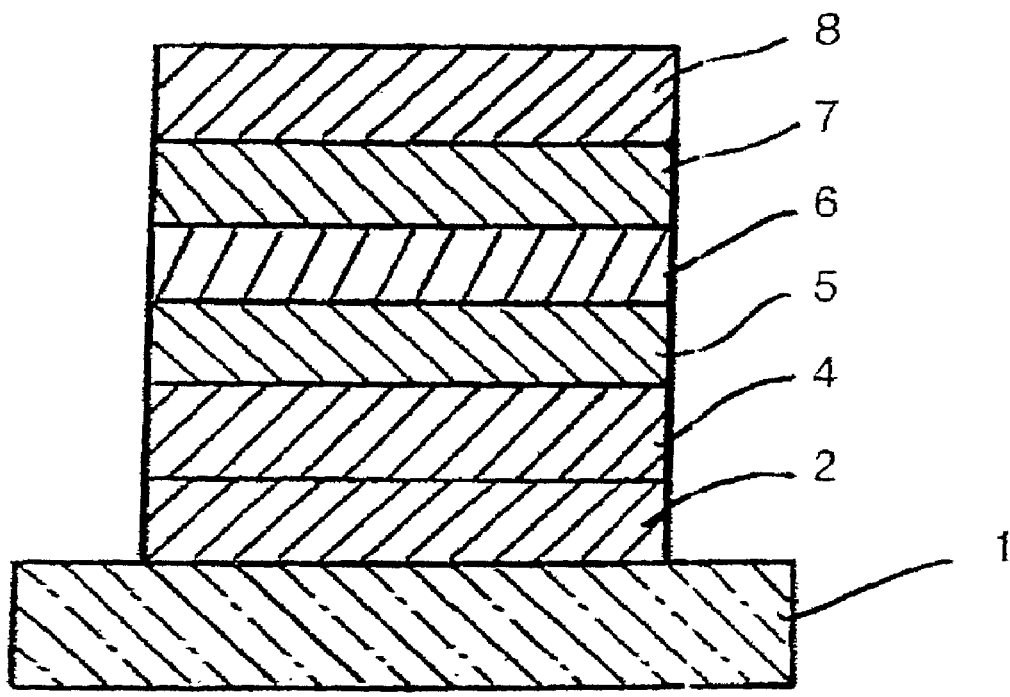
FIG. 2 is a schematic cross-sectional view of another example of the organic electroluminescent device according to the present invention.

For the purpose of further enhancing the luminous efficiency of a device, as shown in FIGS. 1 and 2, an electron transport layer 7 is preferably provided between the hole blocking layer 6 and the cathode 8. The electron transport layer 7 is formed of a compound which can efficiently transport electrons injected from the cathode 8 toward the direction of the hole blocking layer 6 when an electric field is applied between the electrodes.

Examples of materials satisfying such conditions include metal complexes such as aluminum 8-hydroxyquinoline complex (Japanese Unexamined Patent Application Publication No. 59-194393), metal complexes of 10-hydroxybenzo[h]quinoline, oxadiazole derivatives, distyrylbiphenyl derivatives, silole derivatives, 3- or 5-hydroxyflavone metal complexes, benzoxazole metal complexes, benzothiazole metal complexes, trisbenzimidazolylbenzene (U.S. Pat. No. 5,645,948), quinoxaline compounds (Japanese Unexamined Patent Application Publication No. 6-207169), phenanthroline derivatives (Japanese Unexamined Patent Application Publication No. 5-331459), 2-t-butyl-9,10-N,N'-dicyanoanthraquinonediimine, n-type hydrogenated amorphous silicon carbide, n-type zinc sulfide, and n-type zinc selenide.

The electron-transporting property is enhanced by doping the above-mentioned electron-transporting materials with an alkali metal (Japanese Unexamined Patent Application Publication Nos. 10-270171, 2002-100478, and 2002-100482).

When an electron transport layer 7 is formed, the electron affinity of the hole blocking layer 6 is preferably equal to or less than that of the electron transport layer 7.

From the viewpoints of controlling light-emitting area and decreasing the driving voltage, the reduction potentials of the light-emitting material in a light-emitting layer 5, the hole-blocking material in a hole blocking layer 6, and an electron-transporting material in an electron transport layer preferably satisfy the following relationship:

(reduction potential of electron-transporting material)≧(reduction potential of hole-blocking material)≧(reduction potential of light-emitting layer material).

Here, when the electron-transporting material, the hole-blocking material, and the light-emitting layer material each consist of a plurality of components, a material with the lowest reduction potential is used for comparison. In addition, when the light-emitting layer 5 contains a host material and a dopant material, a host material with the lowest reduction potential is used for comparison.

The above-described hole-blocking materials may be used in the electron transport layer 7. In such a case, the electron transport layer 7 may be formed of a single hole-blocking material described above or a combination thereof.

The thickness of the electron transport layer 6 is usually 5 nm or more, preferably 10 nm or more and usually 200 nm or less, preferably 100 nm or less.

The electron transport layer 7 is formed on the hole blocking layer 6 by a coating method or a vacuum deposition method as in the hole transport layer 4. Usually, a vacuum deposition method is employed.

Figure 4:
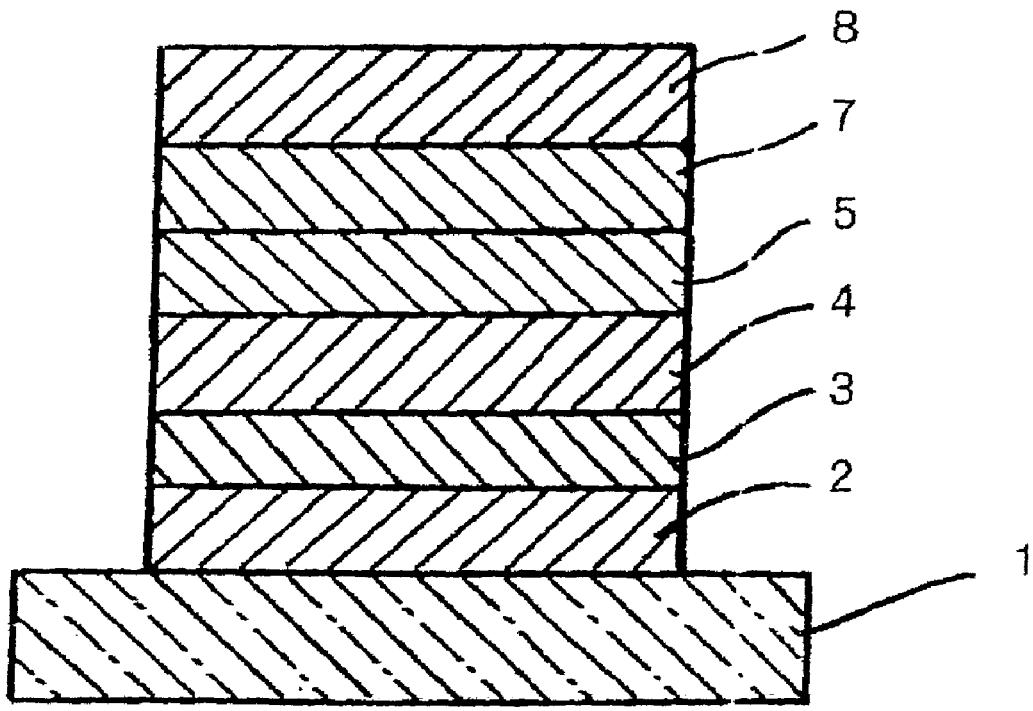
FIG. 4 is a schematic cross-sectional view of another example of the organic electroluminescent device according to the present invention.

As shown in FIG. 4, the electron transport layer 7 may be provided between the light-emitting layer 5 and the cathode 8 without forming a hole blocking layer 6.

[Hole Injection Layer]

Figure 3:
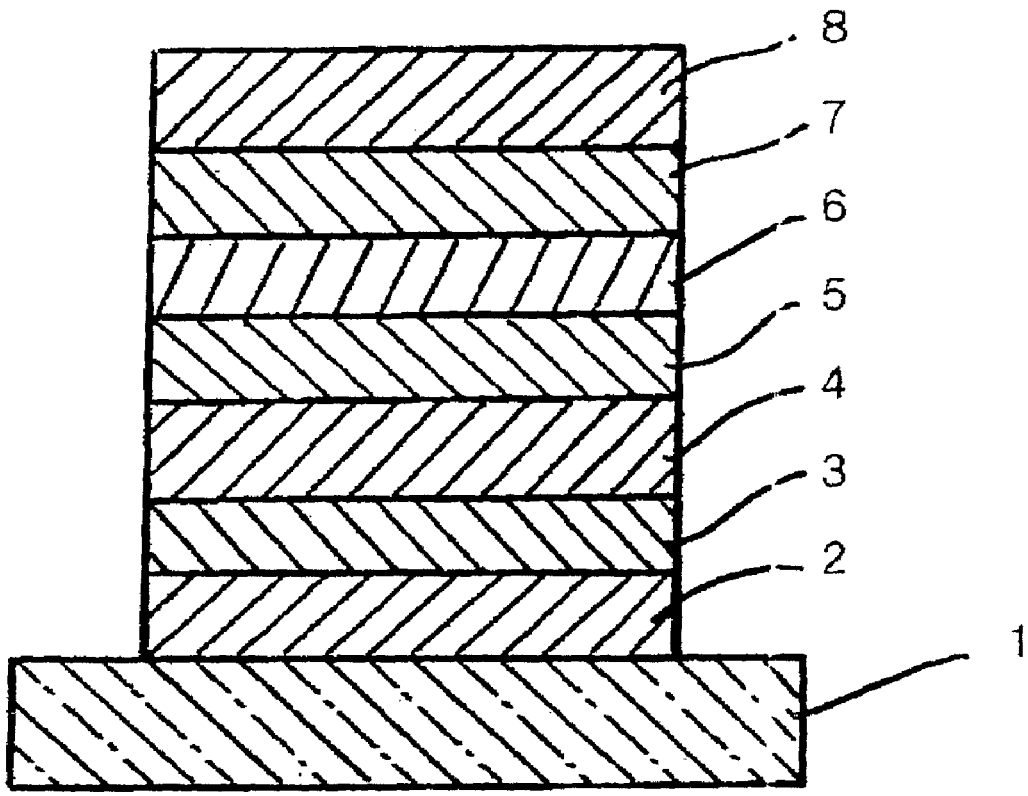
FIG. 3 is a schematic cross-sectional view of another example of the organic electroluminescent device according to the present invention.

For purpose of further enhancing hole-injection efficiency and improving adhesive property of the entire organic layer to the anode 2, as shown in FIGS. 3 and 4, a hole injection layer 3 may be disposed between the hole transport layer 4 and the anode 2. By disposing the hole injection layer 3, the initial driving voltage of an element is reduced and an increase in voltage when the element is continuously driven at a constant current can be suppressed.

The material used as the hole injection layer 3 is required to enable being formed into a thin film which can be in uniform contact with the anode 2 and to be heat stable. The material is required to have a high melting point and glass transition temperature. Preferably, the melting point is 300° C. or more and the glass transition temperature is 100° C. or more. Further, the material is required to have low ionization potential, to be readily injected with holes from the anode 2, and to have high hole mobility.

As the material of the hole injection layer 3, organic compounds, sputtered carbon films (Synth. Met., vol. 91, p. 73, 1997), and metal oxides (J. Phys. D., vol. 29, p. 2750, 1996) have been reported. Examples of the organic compounds include porphyrin derivatives, phthalocyanine compounds (Japanese Unexamined Patent Application Publication No. 63-295695), hydrazine compounds, aromatic diamine derivatives having alkoxy substituents, p-(9-anthryl)-N,N'-di-p-tolylaniline, polythienylenevinylene, poly-p-phenylenevinylene, polyaniline (Appl. Phys. Lett., vol. 64, p. 1245, 1994), polythiophene (Optical Materials, vol. 9, p. 125, 1998), and starburst type aromatic amines (Japanese Unexamined Patent Application Publication No. 4-308688). Examples of the metal oxides include a vanadium oxide, a ruthenium oxide, and a molybdenum oxide.

The constitution of the hole injection layer 3 and others may be a layer containing a low molecular weight organic compound having a property of hole injection/transport and an electron-accepting compound (Japanese Unexamined Patent Application Publication Nos. 11-251067 and 2000-159221), a layer in which nonconjugated high molecular weight compound containing an aromatic amino group doped with an electron-accepting compound according to need (Japanese Unexamined Patent Application Publication Nos. 11-135262, 11-283750, 2000-36390, 2000-150168, 2001-223084, and WO97/33193), or a layer containing a conductive polymer such as polythiophene (Japanese Unexamined Patent Application Publication No. 10-92584).

The material of the hole injection layer 3 may be either a low molecular weight compound or a high molecular weight compound.

Examples of the low molecular weight compound include porphine compounds and phthalocyanine compounds. These compounds may each contain a central metal or not. Preferable examples of these compounds are as follows:

5,10,15,20-tetraphenyl-21H,23H-porphine,
5,10,15,20-tetraphenyl-21H,23H-porphine cobalt(II),
5,10,15,20-tetraphenyl-21H,23H-porphine copper(II),
5,10,15,20-tetraphenyl-21H,23H-porphine zinc(II)
5,10,15,20-tetraphenyl-21H,23H-porphine vanadium(II) oxide,
5,10,15,20-tetra(4-pyridyl)-21H,23H-porphine,
29H,31H-phthalocyanine,
Copper(II) phthalocyanine,
Zinc(II) phthalocyanine,
Titanium phthalocyanine oxide,
Magnesium phthalocyanine,
Lead phthalocyanine, and
Copper(II) 4,4',4'',4'''-tetraaza-29H,31H-phthalocyanine.

The hole injection layer 3 may be formed by thin-film forming as in the hole transport layer 4, but a sputtering method, an electron beam evaporation method, or a plasma CVD method may be further employed when an inorganic material is used.

In the thus formed hole injection layer 3 using a low molecular weight compound, the lower limit of the thickness is usually 3 nm, preferably about 10 nm, and the upper limit of the thickness is usually 100 nm, preferably about 50 nm.

When the material of the hole injection layer 3 is a high molecular weight compound, for example, a coating solution in which the above-mentioned high molecular weight compound, an electron-accepting compound, and further, according to need, a coating property-improving agent such as a binder polymer or leveling agent which does not trap holes are added and dissolved is prepared; the coating solution is applied on the anode 2 by a usual coating method such as spraying, printing, spin coating, dip coating, or die coating or by ink-jet printing; and after drying, a thin film of a hole injection layer 3 can be formed. Examples of the binder polymer include polycarbonates, polyarylates, and polyesters. The hole mobility is decreased when the content of a binder polymer is high. Therefore, a smaller amount of the binder polymer is desirable. Usually, the content in a hole injection layer 3 is preferably 50 wt % or less.

The hole injection layer 3 may be formed by preliminarily forming a thin film on a medium such as a film, supporting substrate, or roll by the above-described thin-film forming method and transferring the thin film on the medium to the anode 2 by heat or pressure.

In the thus formed hole injection layer 3 using a high molecular weight compound, the lower limit of the thickness is usually 5 nm, preferably about 10 nm, and the upper limit of the thickness is usually 1000 nm, preferably about 500 nm.

[Layer Structure of Organic Electroluminescent Device]

The organic electroluminescent device according to the present invention may have a structure inverse to that shown in FIG. 1, namely, a cathode 8, a hole blocking layer 6, a light-emitting layer 5, a hole transport layer 4, and an anode 2 may be stacked on a substrate 1 in this order. As described above, the organic electroluminescent device of the present invention may be disposed between two substrates, at least one of which has high transparency. Similarly, the organic electroluminescent device of the present invention may have a layer structure inverse to that shown in FIG. 2, 3, or 4. In any one of layer structures shown in FIGS. 1 to 4, an optional layer in addition to the above-mentioned layers may be provided to the organic electroluminescent device in the range not departing from the scope of the present invention. Furthermore, appropriate modification, for example, simplifying the layer structure by disposing a layer having functions of plural layers described above, may be conducted.

In addition, it is possible to employ a top emission structure, a transmissive type using transparent electrodes as the anode and the cathode, or a structure in which a plurality of layer structures shown in FIG. 1 are stacked (a structure in which a plurality of light-emitting units are stacked). In such a case, a barrier between the stages is decreased by, for example, using $V_2O_5$ instead of the interface layer (when the anode is made of ITO and the cathode is made of Al, the interface layer is these two layers) between stages (between light-emitting units) as a charge-generating layer (CGL). This is preferable from the viewpoints of luminous efficiency and driving voltage.

The present invention can be applied to a single organic electroluminescent device or a device having a structure in which a plurality of organic electroluminescent devices are arranged in an array or a structure in which anodes and cathodes are arranged in an X—Y matrix.

EXAMPLES

The present invention will now be described more specifically with reference to Examples, but the present invention is not limited to the description of the following Examples unless the gist thereof is overstepped.

Synthesis Example of Organic Compound

Synthesis examples of the organic compound according to the present invention will now be described.

In the following synthesis examples, the glass transition temperature was determined by DSC measurement, the vaporization temperature was determined by TG-DTA measurement, and the melting point was determined by DSC measurement or TG-DTA measurement.

Synthesis Example 1

Target Compounds 1 and 2

[Compound 80]

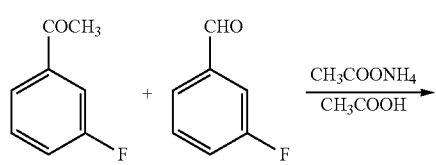

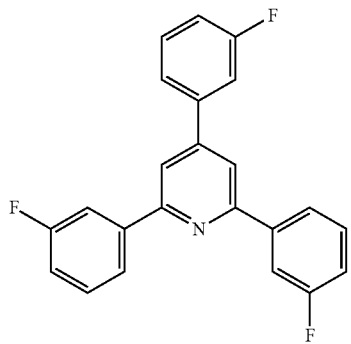

Target Compound 1

3-Fluorobenzaldehyde (6.74 g), 3-fluoroacetophenone (15 g), ammonium acetate (53.56 g), and acetic acid (136 ml) were stirred while heating under reflux for 10 hr, and were then allowed to cool to room temperature. Then, the crystal precipitated in the system was collected by filtration, washed twice by suspending it in ethanol, and dried under reduced pressure to obtain 4.15 g (yield: 22%) of a target compound 1 as a white crystal.

[Compound 81]

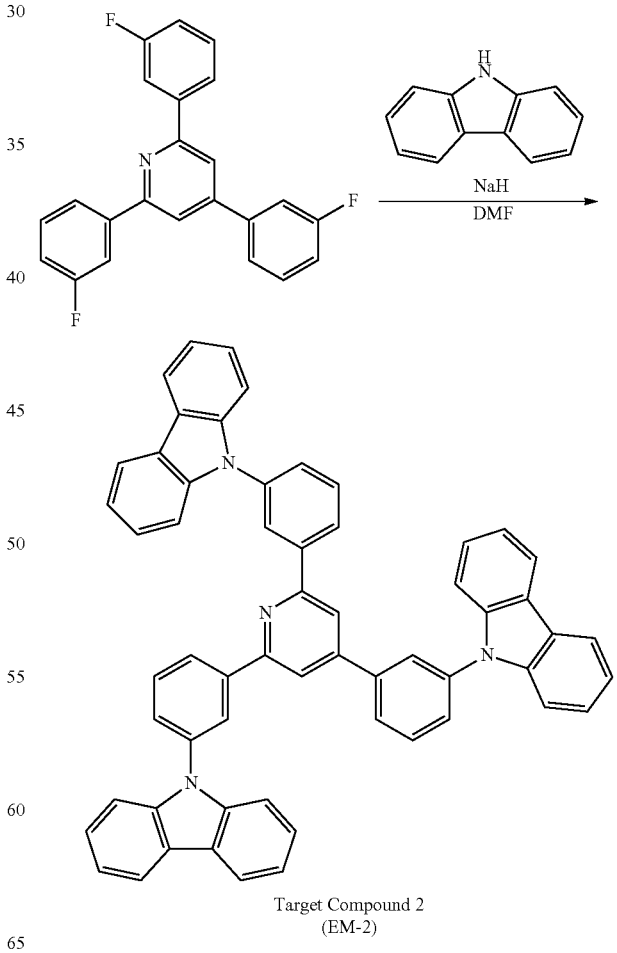

Target Compound 2
(EM-2)

A mixture solution of sodium hydride (55%) (1.45 g) and 100 ml of dimethylformaldehyde was sufficiently stirred under nitrogen atmosphere while gradually adding carbazole (5.55 g) thereto. Then, the mixture was heated to 80° C. while stirring. When the system was completely dissolved, and then the previously synthesized target compound 1 (2.0 g) was added thereto. Then, the mixture was stirred while heating under reflux for 28 hr, and was then allowed to cool to room temperature. Then, 90 ml of water and 90 ml of methanol were added to the mixture to precipitate crystal. The precipitated crystal was collected by filtration, washed by suspending it in methanol upon heating, and then purified by column chromatography (methylene chloride/n-hexane=3/7). Further, the crystal was washed by suspending it in methanol and then dried under reduced pressure to obtain 0.83 g (yield: 53%) of a target compound 2 as a white crystal. This crystal (0.83 g) was purified by sublimation to yield 0.58 g of a white solid.

The white solid was confirmed to be an target compound 2 by DEI-MS (m/z=802 (M+)).

The white solid had a vaporization temperature of 542° C., a melting point of 288° C., and a glass transition temperature of 146° C.

Synthesis Example 2

Target Compounds 3 and 4

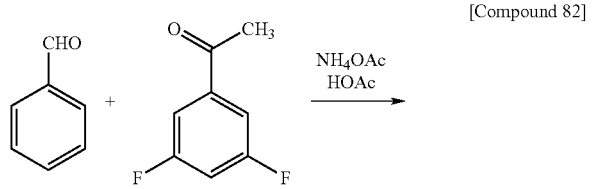

[Compound 82]

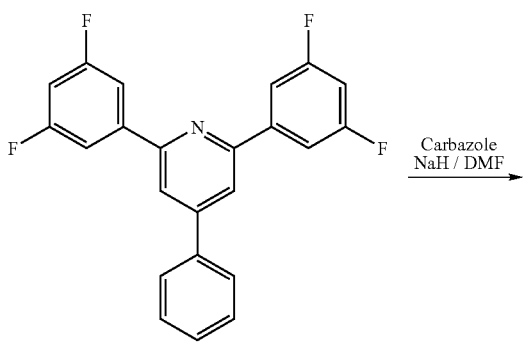

Target Compound 3

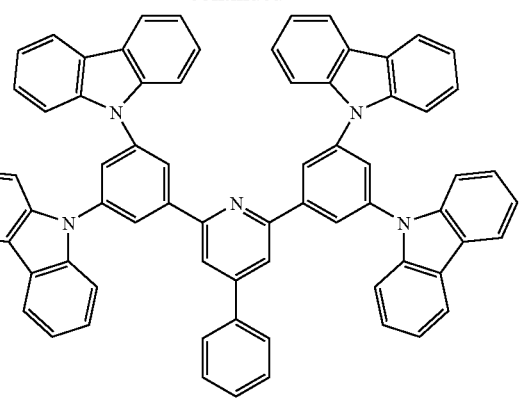

Target Compound 4
(EM-3)

Benzaldehyde (3.18 g), 3',5'-difluoroacetophenone (9.37 g), ammonium acetate (29.6 g), and acetic acid (75 ml) were stirred in air at 100° C. for 4.9 hr, and then cooled by ice. Methanol and water were added thereto, and the resulting precipitate was collected by filtration and purified by suspending it in methanol. After drying by heating under reduced pressure, a target compound 3 (2.03 g) was obtained.

Carbazole (5.37 g) was added to an anhydrous N,N-dimethylformamide suspension (100 ml) containing sodium hydride (55%, 1.40 g) under nitrogen flow, and the resulting mixture was stirred at 80° C. for 60 min. Then, the target compound 3 (2.03 g) was added thereto. Then, the mixture was stirred while heating under reflux for 4.9 hr. Water (50 ml) and methanol (50 ml) were added to the mixture while cooling on ice. The resulting precipitate was collected by filtration and washed with methanol. The resulting solid content was extracted from chloroform (800 ml) and concentrated, and then purified by suspending it in an ethanol/chloroform mixture solvent while heating under reflux. After drying by heating under reduced pressure, a target compound 4 (3.69 g) was obtained.

The solid content was confirmed to be an target compound 4 by DEI-MS (m/z=962 (M+)).

The solid content had a vaporization temperature of 562° C. and a melting point of 395° C. The glass transition temperature was not detected.

Synthesis Example 3

Target Compounds 5 and 6

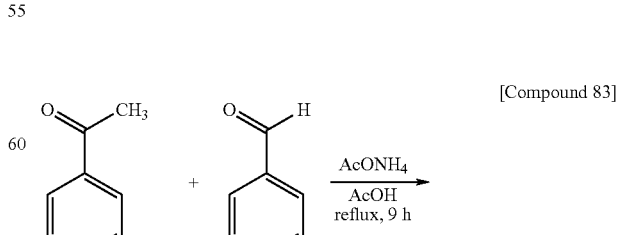

[Compound 83]

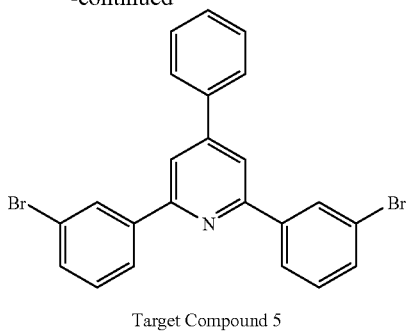

Target Compound 5

3'-Bromoacetophenone (25.0 g), benzaldehyde (6.66 g), ammonium acetate (62.0 g), and acetic acid (157 ml) were stirred while heating under reflux for 9 hr, and were then allowed to cool to room temperature. Then, the precipitated crystal was collected by filtration, washed twice with ethanol, and dried under reduced pressure to obtain a target compound 5, namely, 2,6-bis(3-bromophenyl)-4-phenylpyridine (6.72 g, yield: 23%), as a white crystal.

[Compound 84]

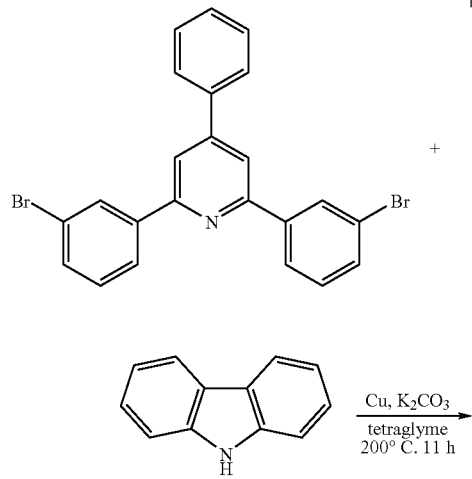

Target Compound 6 (EM-1)

Under nitrogen flow, 2,6-bis(3-bromophenyl)-4-phenylpyridine (1.45 g), carbazole (1.56 g), copper powder (0.40 g), potassium carbonate (1.72 g), and tetraglyme (5 ml) were stirred while heating under reflux for 11 hr, and then allowed to cool to room temperature. Chloroform (200 ml) was added thereto and the resulting mixture was stirred. The insoluble matter was removed by filtration. Chloroform contained in the filtrate was evaporated under reduced pressure, and then methanol was added thereto. The resulting precipitate was collected by filtration and purified by silica-gel column chromatography (n-hexane/methylene chloride=2/1). Further, the precipitate was washed with a methylene chloride/methanol mixture solution and then dried under reduced pressure to obtain a target compound 6, namely, 2,6-bis(N-carbazolylphenyl)-4-phenylpyridine (0.94 g, yield: 47%), as a white crystal. This white crystal was purified by sublimation to yield 0.83 g of a white solid.

The white solid was confirmed to be a target compound 6, 2,6-bis(N-carbazolylphenyl)-4-phenylpyridine, by DEI-MS (m/z=637 (M$^+$)) and $^1$H-NMR.

$^1$H-NMR (CDCl$_3$, 270 MHz) data are shown below.

8.40 (s, 2H), 8.31 (d, 2H), 8.16 (d, 4H9, 7.96 (s, 2H), 7.75 (dd, 2H), 7.73 (d, 2H), 7.65 (d, 2H), 7.54-7.46 (m, 7H), 7.36 (dd, 4H), 7.28 (dd, 4H)

The white solid had a vaporization temperature of 489° C., a melting point of 266° C., and a glass transition temperature of 114° C.

Synthesis Example 4

Target Compounds 7 and 8

[Compound 85]

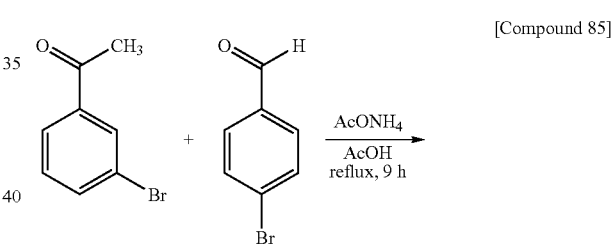

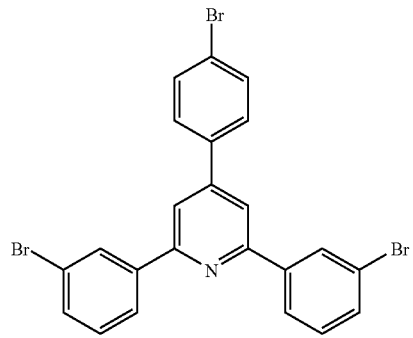

Target Compound 7

3'-Bromoacetophenone (40.3 g), 4-bromobenzaldehyde (15 g), ammonium acetate (79.9 g), and acetic acid (150 ml) were stirred while heating under reflux for 9 hr, and were then allowed to cool to room temperature. Then, the precipitated crystal was collected by filtration, washed twice with ethanol, and dried under reduced pressure to obtain a target compound 7 (9.35 g, yield: 21%), as a white crystal.

[Compound 86]

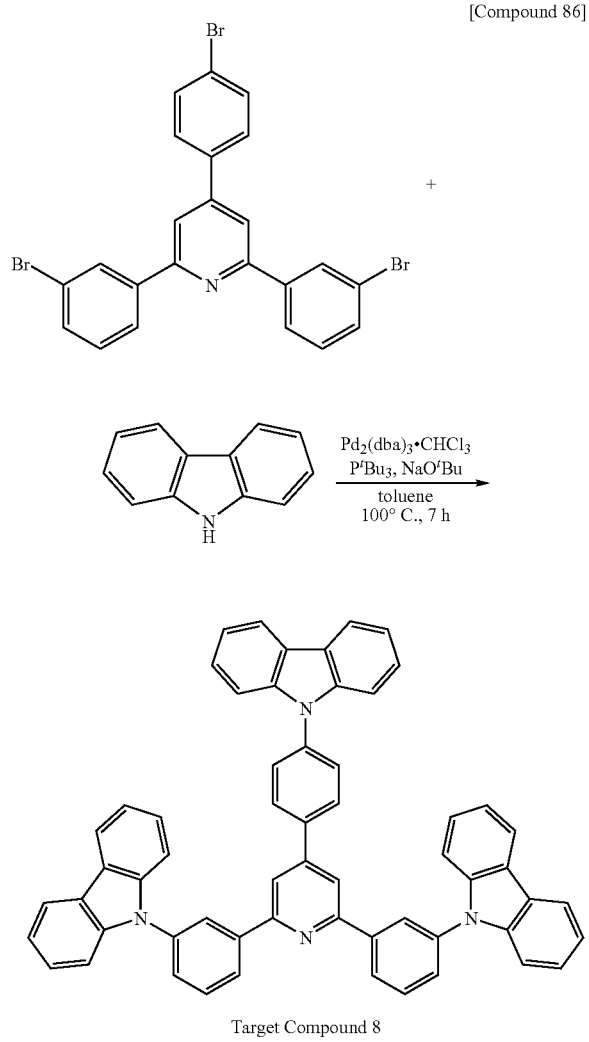

Target Compound 8

[Compound 87]

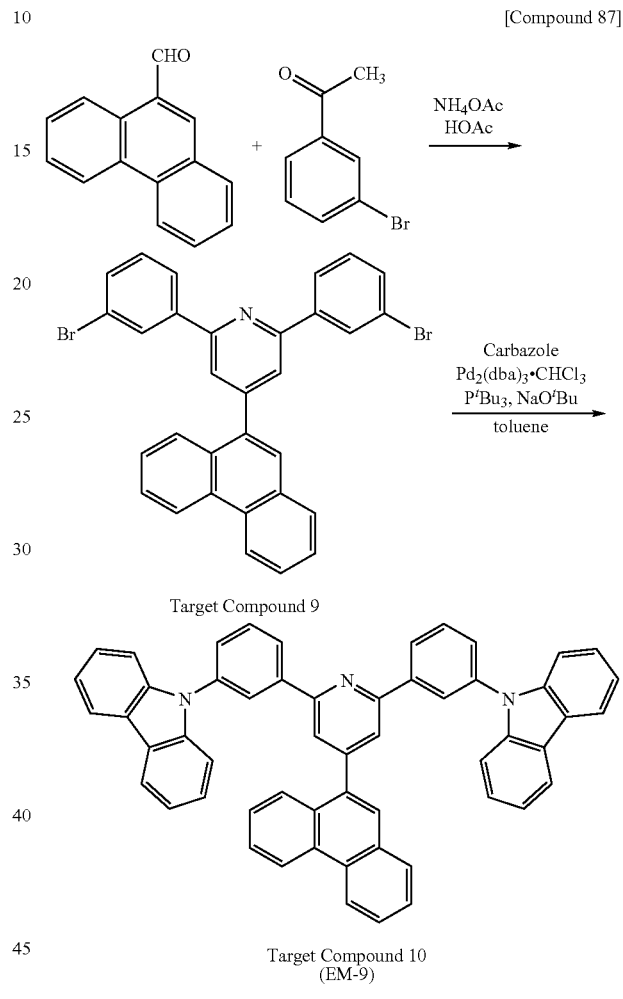

Target Compound 9

Target Compound 10
(EM-9)

A solution was prepared by stirring tris(dibenzylideneacetone)dipalladium(0) chloroform complex (0.46 g), tri(t-butyl)phosphine (0.9 g), and toluene (10 ml) under nitrogen atmosphere at 60° C. for 10 min. This solution was added to a mixture heated to 60° C. of the target compound 7 (4.5 g), carbazole (5.0 g), t-butoxysodium (5.3 g), and toluene (150 ml) under nitrogen atmosphere, and the resulting mixture was stirred at 100° C. for 8 hr. After allowing to cool to room temperature, the insoluble matter was removed by filtration. The filtrate was concentrated, and methanol was added thereto. The precipitated crystal was collected by filtration, washed with a water/methanol mixture solution, and purified by silica-gel column chromatography (n-hexane/methylene chloride=7/3). Further, the crystal was washed with ethyl acetate and then dried under reduced pressure to obtain a target compound 8 (1.70 g, yield: 25%), as a white crystal. This white crystal (1.7 g) was purified by sublimation to yield 1.26 g of a white solid.

The white solid was confirmed to be a target compound 8 by DEI-MS (m/z=802 (M$^+$)).

The white solid had a vaporization temperature of 553° C. and a glass transition temperature of 152° C.

Synthesis Example 5

Target Compounds 9 and 10

9-Phenanthrenecarboxyaldehyde (4.29 g), 3'-bromoacetophenone (8.28 g), ammonium acetate (20.5 g), and acetic acid (52 ml) were stirred in air at 100° C. for 5 hr, and the supernatant was removed. Methanol was added thereto for washing the remaining viscous liquid. After the removing of the washings, the viscous liquid was purified by silica-gel column chromatography and suspension washing with methanol and then dried by heating under reduced pressure to obtain a target compound 9 (3.00 g).

A solution was prepared by stirring tris(dibenzylideneacetone)dipalladium(0) chloroform complex (0.46 g), tri(t-butyl)phosphine (0.9 g), and anhydrous toluene (4 ml) under nitrogen atmosphere at 50° C. for 30 min. This solution was added to a solution of the target compound 9 (2.26 g), carbazole (1.61 g), tert-butylphosphine (0.19 g), and anhydrous toluene (36 ml) under nitrogen flow, and the resulting mixture was stirred while heating under reflux for 1.5 hr. Then, methanol (100 ml) was added to the resulting solution, and the resulting precipitate was collected by filtration. The precipitate was extracted with dichloromethane (300 ml), purified by silica-gel column chromatography, and dried by heating under reduced pressure to obtain a target compound 10 (1.70 g).

The obtained compound was confirmed to be a target compound 10 by DEI-MS (m/z=737 (M$^+$)).

The compound had a vaporization temperature of 527° C., a melting point of 271° C., and a glass transition temperature of 147° C.

Synthesis Example 6

Target Compounds 11 to 13

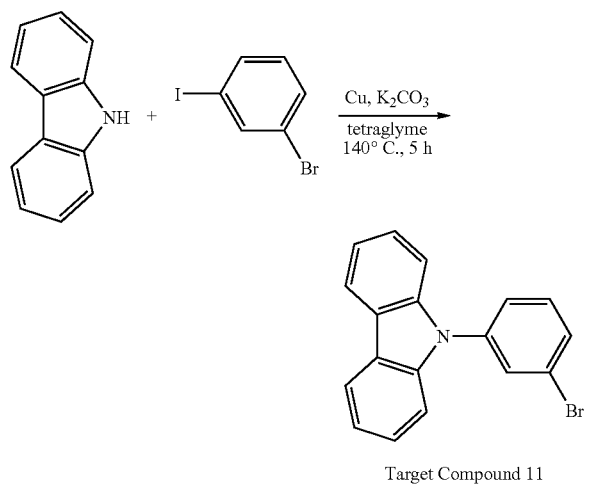

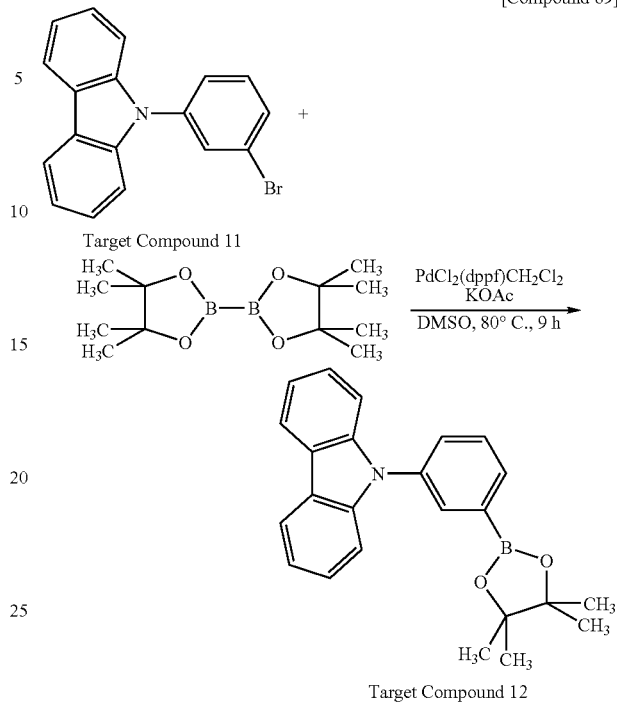

Under nitrogen flow, carbazole (7.00 g), 3-bromoiodobenzene (14.2 g), copper powder (2.66 g), potassium carbonate (5.79 g), and tetraglyme (10 ml) were stirred while heating to 140° C. for 5 hr and then allowed to cool to room temperature. After the completion of the reaction, chloroform was added to the reaction solution, and the insoluble matter was removed by filtration. Chloroform contained in the filtrate was evaporated under reduced pressure, and the resulting matter was purified by silica-gel column chromatography (n-hexane/toluene=4/1) and dried under reduced pressure to obtain a target compound 11 (10.5 g, yield: 78%) as a colorless viscous liquid.

Under nitrogen flow, the target compound 11 (10.5 g), bis(pinacolate)diboron (9.93 g), potassium acetate (10.9 g), and anhydrous dimethylsulfoxide (190 ml) were stirred while heating to 60° C. for 15 min, and [1,1'-bis(diphenylphosphino)ferrocene]dichloropalladium(II) dichloromethane complex (0.799 g) was added thereto. The resulting mixture was stirred while heating to 80° C. for 9 hr and then allowed to cool to room temperature. To the reaction solution, water (250 ml) and toluene (500 ml) were added, and the resulting mixture was stirred. After the water layer was reextracted twice with toluene, the organic layers were mixed. Further, magnesium sulfate and active clay were added thereto. The magnesium sulfate and active clay were removed by filtration, and the toluene was evaporated under reduced pressure. The precipitated crystal was washed with cold methanol and dried under reduced pressure to obtain a target compound 12 (9.86%, yield: 80%) as a white crystal.

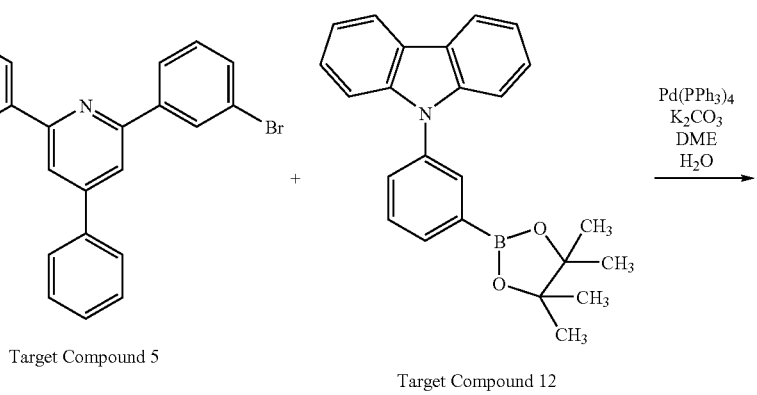

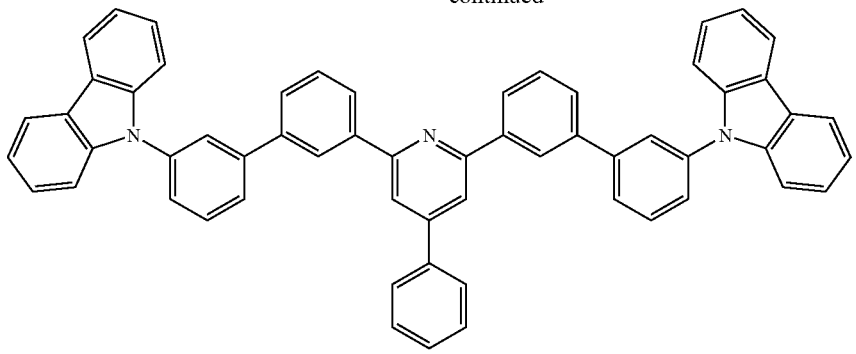

Target Compound 13
(EM-6)

To a mixture of the target compound 5 (1.86 g), the target compound 12 (3.84 g), dimethoxyethane (80 ml), and water (12 ml), tetrakis(triphenylphosphine)palladium (0.37 g) and potassium carbonate (3.32 g) were sequentially added. The resulting mixture was stirred while heating under reflux for 6 hr. To the resulting solution, brine (100 ml) was added. After extraction with dichloromethane (2×100 ml), anhydrous magnesium sulfate and active clay were added to the organic layer. The mixture was stirred, filtered, and concentrated to obtain a solid content. The solid content was purified by silica-gel column chromatography to obtain a target compound 13 (2.16 g).

The obtained compound was confirmed to be a target compound 13 by DEI-MS (m/z=789 (M$^+$)).

The compound had a vaporization temperature of 541° C. and a glass transition temperature of 125° C. The melting point was not detected.

Synthesis Example 7

Target Compounds 14 to 16

[Compound 91]

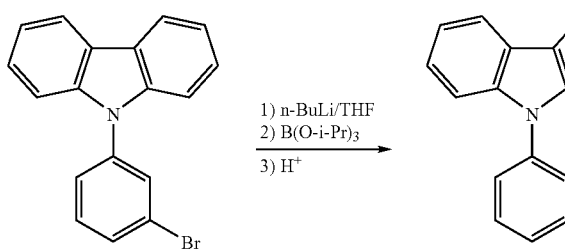

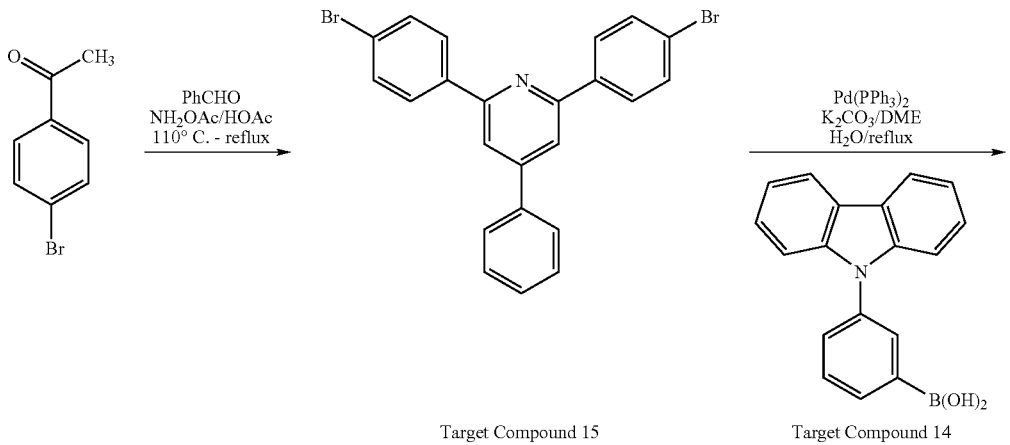

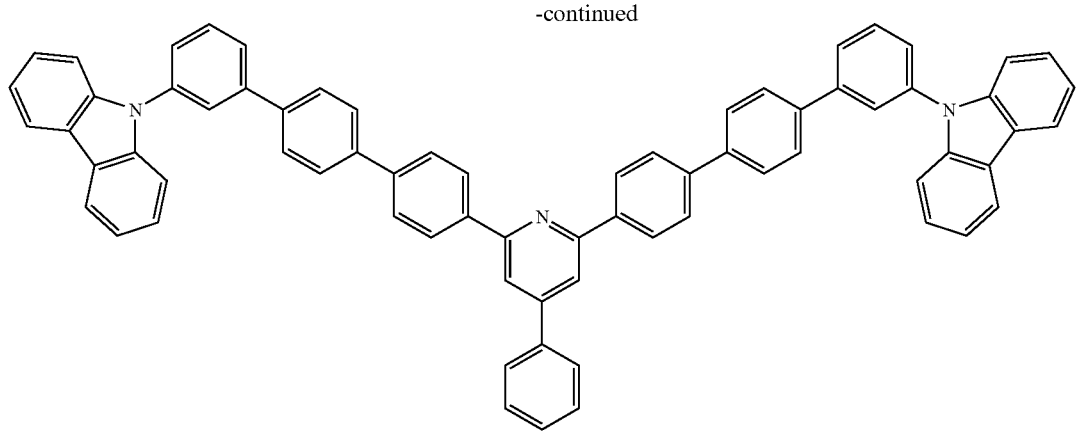

Target Compound 16
(EM-10)

Under nitrogen flow, a n-hexane solution (27.4 ml) containing 1.54 M n-butyllithium was dropped to an anhydrous tetrahydrofuran (400 ml) solution containing the target compound 11 (9.06 g) over 7 min while cooling in ethanol bath at −60 to −65° C. The resulting mixture was stirred for min, and triisopropoxyborane (13.0 ml) was added thereto. The mixture was stirred at room temperature for 2.2 hr, and 1 N hydrochloric acid solution (45 ml) was added thereto and further stirred for 30 min. Tetrahydrofuran in the resulting solution was evaporated under reduced pressure, and diethyl ether (400 ml) and saturated brine (100 ml) were added thereto and shaken. Then, the organic layer was obtained by fractionation and washed with saturated brine. Anhydrous magnesium sulfate and active clay were added to the resulting organic layer. The mixture was stirred, filtrated, and concentrated. The resulting solid content was washed by suspending it in water and n-hexane, and reprecipitated from ethanol-n-hexane to obtain a target compound 14 (4.03 g).

To a mixture of the target compound 15 (1.86 g), the target compound 14 (4.0 g), dimethoxyethane (80 ml), and water (12 ml), tetrakis(triphenylphosphine)palladium (0.37 g) and potassium carbonate (3.32 g) were sequentially added. The resulting mixture was stirred while heating under reflux for 4.5 hr. To the resulting solution, methanol (70 ml) and water (50 ml) were added. After filtration, the resulting solid content was extracted with dichloromethane (200 ml). Active clay was added to the extract. The mixture was stirred, filtered, and concentrated to obtain a solid content. The solid content was purified by reprecipitation from tetrahydrofuran-ethanol-methanol to obtain a target compound 16 (2.76 g).

The obtained compound was confirmed to be a target compound 16 by DEI-MS (m/z=789 (M$^+$)).

The compound had a vaporization temperature of 556° C., a melting point of 221° C., a crystallization temperature of 288° C., and a glass transition temperature of 141° C.

Synthesis Example 8

Target Compounds 17 and 18

[Compound 92]

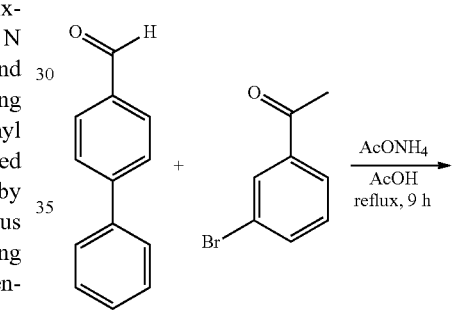

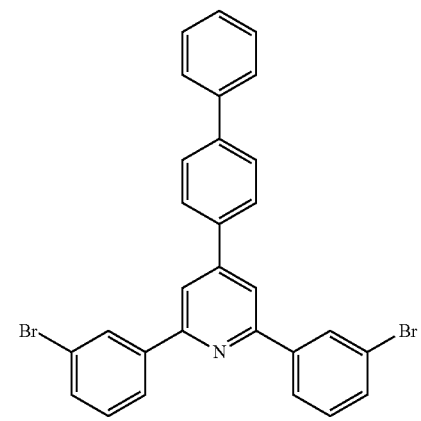

Target Compound 17

3'-Bromoacetophenone (25 g), 4-phenylbenzaldehyde (13 g), ammonium acetate (64.4 g), and acetic acid (165 ml) were stirred while heating under reflux for 9 hr and then allowed to cool to room temperature. Then, the precipitated crystal was collected by filtration, washed twice with ethanol, and dried under reduced pressure to obtain a target compound 17 (7.483 g, yield: 21.2%) as a white crystal.

The white solid had a glass transition temperature of 126° C. and a vaporization temperature of 526° C.

Synthesis Example 9

Target Compounds 19 and 20

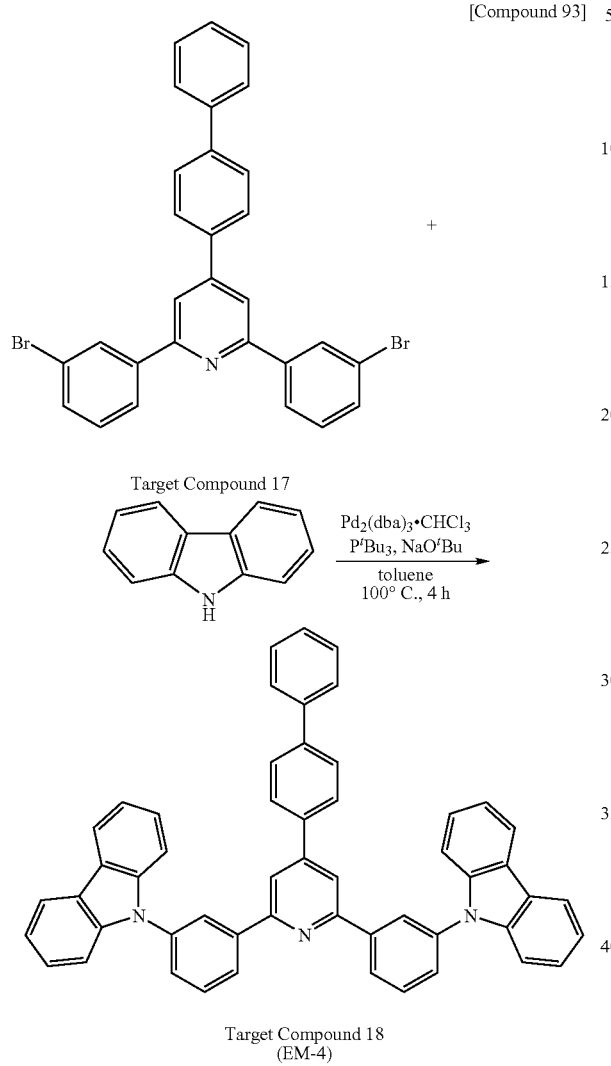

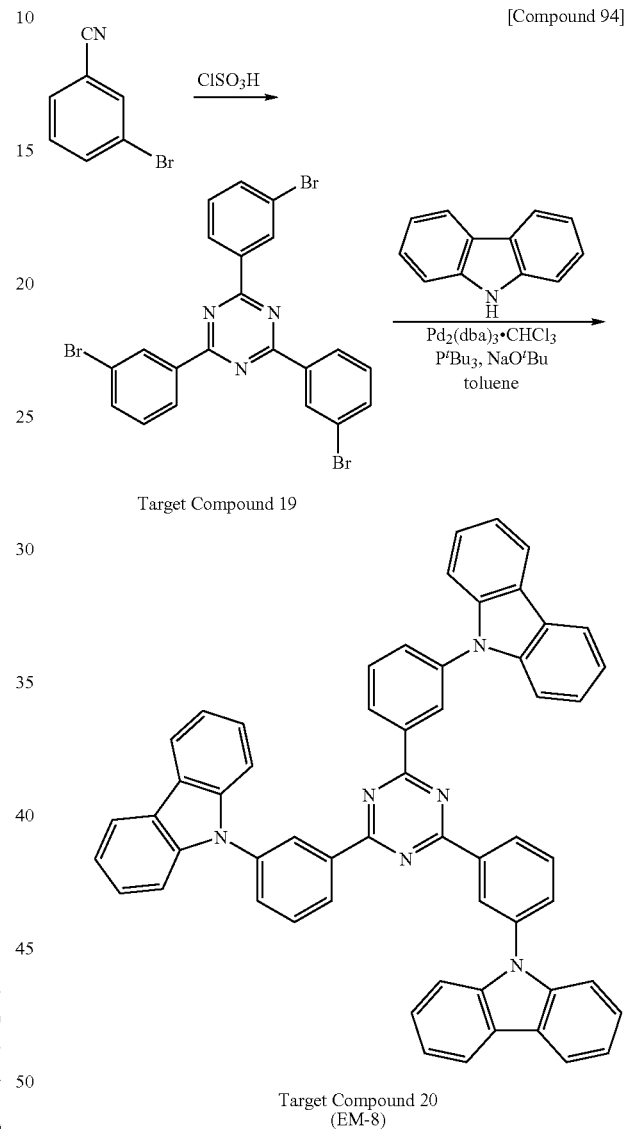

A solution was prepared by stirring tris(dibenzylideneacetone)dipalladium(0) chloroform complex g), tri(t-butyl)phosphine (0.53 g), and toluene (10 ml) under nitrogen atmosphere at 60° C. for 10 min. This solution was added to a mixture heated to 60° C. of the target compound 17 (5.0 g), carbazole (3.7 g), t-butoxysodium (3.92 g), and toluene (150 ml) under nitrogen atmosphere, and the resulting mixture was stirred at 110° C. for 4 hr. After allowing to cool to room temperature, the insoluble matter was removed by filtration. The filtrate was concentrated, and methanol was added thereto. The precipitated crystal was collected by filtration, washed with a water/methanol mixture solution, washed by suspending it in ethyl acetate while heating, and purified by silica-gel column chromatography (n-hexane/methylene chloride=2/1). Further, the crystal was washed with ethyl acetate and then dried under reduced pressure to obtain a target compound 18 (4.345 g, yield: 65.8%) as a white crystal. This white crystal (1.9 g) was purified by sublimation to yield 1.5 g of a white solid.

The white solid was confirmed to be a target compound 18 by DEI-MS (m/z=713 (M$^+$)).

Under nitrogen flow, 3-bromobenzonitrile (7.81 g) was added to chlorosulfonic acid (14.3 ml) in an ice bath, and the mixture was stirred until to obtain a uniform solution and further stirred at room temperature for 5.7 hr. The resulting solution was slowly added to iced water (220 ml) and well stirred. The precipitate was collected by filtration, washed with methanol, and dissolved in N,N-dimethylformamide (150 ml) at 110° C. To the resulting solution, ethanol (30 ml) was added. The resulting precipitate was collected by filtration and dried to obtain a target compound 19 as a white solid (4.26 g).

A solution was prepared by stirring tris(dibenzylideneacetone)dipalladium(0) chloroform complex (0.154 g), tri(t-butyl)phosphine (0.24 ml), and toluene (7 ml) under nitrogen atmosphere at 50° C. for 30 min. This solution was added to a mixture solution of the target compound 19 (1.50 g), carbazole (1.65 g), t-butoxysodium (1.74 g), and anhydrous toluene (82 ml) under nitrogen flow, and the resulting mixture was stirred while heating under reflux for 6.3 hr. To the resulting solution, methanol (110 ml) was added. The resulting precipitate was collected by filtration and extracted with chloroform. The solid content obtained by evaporation of the solvent was washed with a chloroform-methanol mixture solution, further recrystallized from N,N-dimethylformamide, and purified by sublimation (degree of vacuum: 1×10⁻³ Pa, highest heating temperature: 420° C.) to obtain a target compound 20 as a light yellow solid (1.21 g).

The obtained light yellow solid was confirmed to be a target compound 20 by DEI-MS (m/z=804 (M⁺)).

The compound had a glass transition temperature of 159° C., a crystallization temperature of 239° C., a melting point of 323° C., and a vaporization temperature of 551° C.

Synthesis example 10

Target Compounds 21 to 23

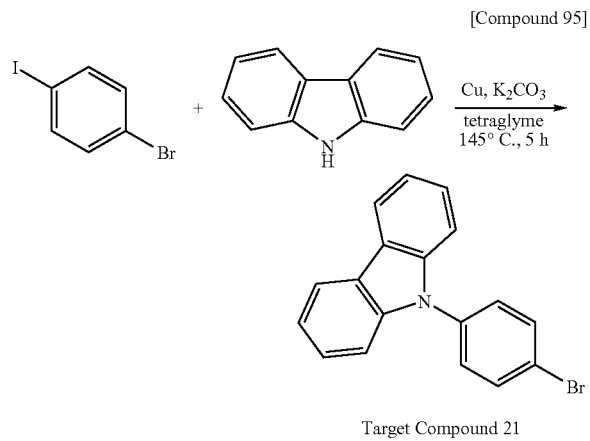

Target Compound 21

Under nitrogen flow, carbazole (6.82 g), 4-bromoiodobenzene (15.0 g), copper powder (2.61 g), potassium carbonate (11.3 g), and tetraglyme (30 ml) were stirred while heating to 145° C. for 5 hr and then allowed to cool to room temperature. Then, chloroform was added to the reaction solution, and the insoluble matter was removed by filtration. Chloroform contained in the filtrate was evaporated under reduced pressure, and the resulting matter was purified by silica-gel column chromatography (n-hexane/toluene=4/1) and dried under reduced pressure to obtain a target compound 21 (9.08 g, yield: 69%) as a white crystal.

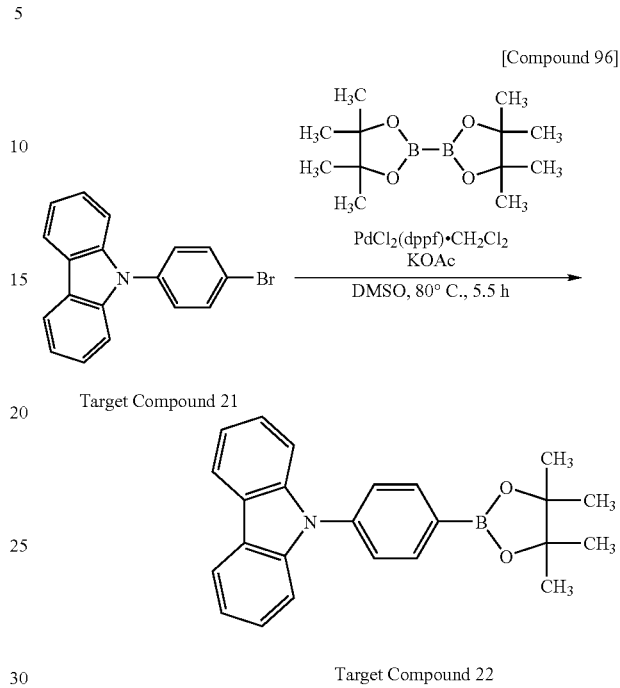

Target Compound 22

Under nitrogen flow, the target compound 21 (4.50 g), bis(pinacolate)diboron (4.61 g), potassium acetate (4.61 g), and dimethylsulfoxide (75 ml) were stirred while heating to 60° C. for 15 min, and [1,1'-bis(diphenylphosphino)ferrocene]dichloropalladium(II) dichloromethane complex (0.343 g) was added thereto. The resulting mixture was stirred while heating to 80° C. for 6 hr and then allowed to cool to room temperature. To the reaction solution, water (250 ml) and toluene (500 ml) were added, and the resulting mixture was stirred. After the water layer was reextracted twice with toluene, the organic layers were mixed. Further, magnesium sulfate and active clay were added thereto. The magnesium sulfate and active clay were removed by filtration, and the toluene was evaporated under reduced pressure. The precipitated crystal was washed with cold methanol and dried under reduced pressure to obtain a target compound 22 (4.46 g, yield: 86%) as a white crystal.

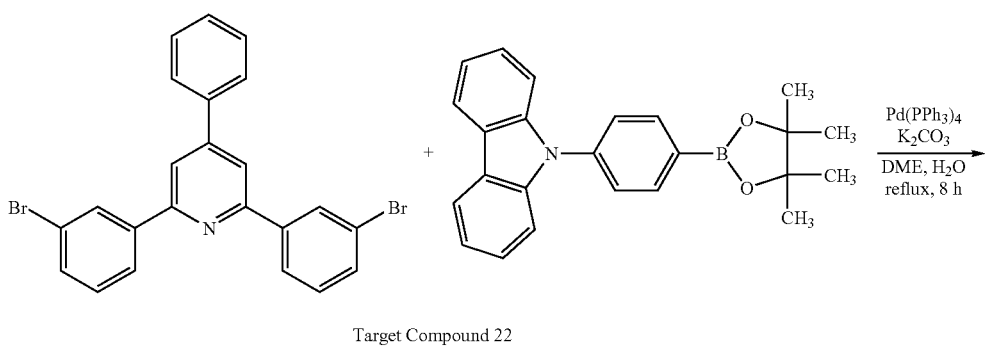

-continued

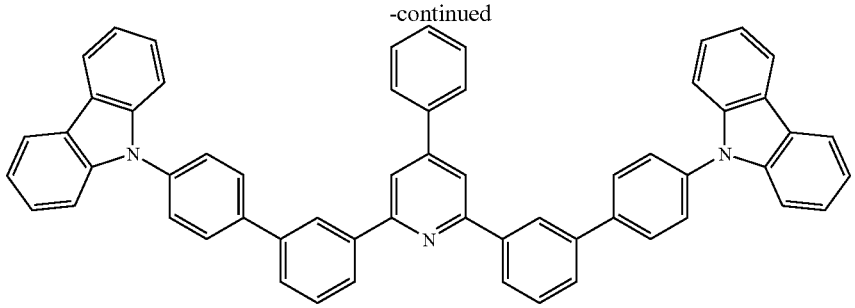

Target Compound 23
(EM-5)

Under nitrogen flow, tetrakis(triphenylphosphine)palladium (0.183 g) was added to a mixture of 2,6-bis(3-bromophenyl)-4-phenylpyridine (1.47 g), the target compound 22 (2.80 g), potassium carbonate (2.62 g), dimethoxyethane (15 ml), and water (5 ml). The resulting mixture was stirred while heating under reflux for 8 hr and then allowed to cool to room temperature. To the reaction solution, methanol was added. The resulting precipitate was collected by filtration and washed with a water/methanol mixture solution. Further, the precipitate was purified by silica-gel column chromatography (n-hexane/methylene chloride=3/2), washed with ethyl acetate and a methylene chloride/ethanol mixture solution, and dried under reduced pressure to obtain a target compound 22 (1.76 g, yield: 71%) as a white crystal. This white crystal was purified by sublimation to yield 1.50 g of a white solid.

The white solid was confirmed to be a target compound 23 by DEI-MS (m/z=790 (M+)).

The compound had a vaporization temperature of 558° C., a melting point of 295° C., and a glass transition temperature of 143° C.

Synthesis Example 11

Target Compounds 24

[Compound 98]

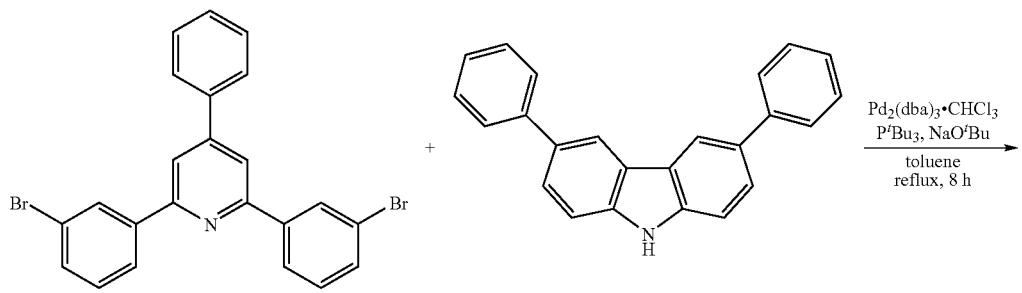

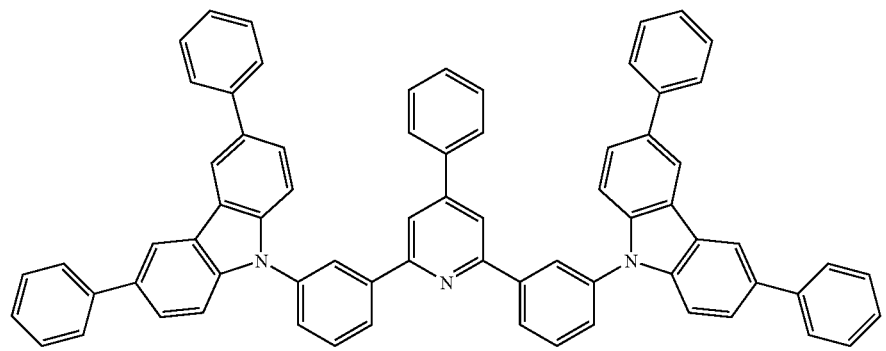

Target Compound 24
(EM-7)

According to an ordinary process, 3,6-diphenylcarbazole was synthesized by reacting 3,6-dibromocarbazole and phenylboronic acid.

A solution was prepared by stirring tris(dibenzylideneacetone)dipalladium(0) chloroform complex (0.104 g), tri(t-butyl)phosphine (0.162 g), and toluene (5 ml) under nitrogen atmosphere at 60° C. for 10 min. This solution was added to a mixture heated to 60° C. of 2,6-bis(3-bromophenyl)-4-phenylpyridine (1.30 g), 3,6-diphenylcarbazole (2.68 g), t-butoxysodium (1.18 g), and toluene (25 ml) under nitrogen atmosphere, and the resulting mixture was stirred at 110° C. for 8 hr. The mixture was allowed to cool to room temperature and concentrated, and methanol was added thereto. The resulting precipitate was collected by filtration and washed with a water/methanol mixture solution. The precipitate was purified by silica-gel column chromatography (n-hexane/toluene=1/1) and washed with an N,N-dimethylformamide/ethanol mixture solution and a methylene chloride/methanol mixture solution and then dried under reduced pressure to obtain a target compound 24 (1.81 g, yield: 69%) as a white crystal. This white crystal was purified by sublimation to yield 1.35 g of a white solid.

The white solid was confirmed to be a target compound 24 by DEI-MS (m/z=924 (M$^+$)).

The compound had a vaporization temperature of 570° C. and a glass transition temperature of 172° C. The melting point was not observed.

[Fabrication Example of Organic Electroluminescent Device]

Exemplary fabrication processes of organic electroluminescent devices according to the present invention will now be described.

Further, a part of fabricated organic electroluminescent elements were subjected to the following operating life test.

<Operating Life Test 1>
The fabricated elements were subjected to an operating life test 1 under the following conditions:
Temperature: room temperature
Driving system: direct current driving (DC driving)
Initial luminance: 2500 cd/m$^2$
Times required to decrease luminance by 20% of the initial level ($L/L_0$=0.8) by continuous emission at a constant current were compared. The times were determined as relative times provided that the time of a standard device 2 fabricated in Reference Example 2 described below was 1.00.

<Operating Life Test 2>
The fabricated devices were subjected to an operating life test 2 under the following conditions:
Temperature: room temperature
Driving system: direct current driving (DC driving)
Initial luminance: 2500 cd/m$^2$
Times required to decrease luminance by 30% of the initial level ($L/L_0$=0.7) by continuous emission at a constant current were compared. The times were determined as relative times provided that the time of a standard device 1 fabricated in Reference Example 1 described below was 1.00.

<Operating Life Test 3>
The fabricated devices were subjected to an operating life test 3 under the following conditions:
Temperature: room temperature
Driving system: direct current driving (DC driving)
Initial luminance: 2500 cd/m$^2$
Times required to decrease luminance by 50% of the initial level ($L/L_0$=0.5) by continuous emission at a constant current were compared. The times were determined as relative times provided that the time of a standard device 1 fabricated in Reference Example 1 described below was 1.00.

Reference Example 1

Fabrication of Standard Device 1

An organic electroluminescent device having a structure shown in FIG. 3 was fabricated by a method shown below.

A transparent indium/tin oxide (ITO) conductive film having a thickness of 150 nm was deposited on a glass substrate 1. The conductive film (sputtered film: a sheet resistance of 15Ω) was patterned to stripes having a width of 2 mm by a usual photolithography process and hydrochloric acid etching to form an anode 2. The patterned ITO substrate was washed by ultrasonic cleaning first using acetone, followed by water washing using deionized water, and then ultrasonic cleaning using isopropyl alcohol. After drying with nitrogen blow, the substrate was lastly cleaned with ultraviolet ozone.

As a material of a hole injection layer 3, non-conjugated polymer (PB-1 (weight average molecular weight: 29400, number average molecular weight: 12600)) containing an aromatic amino group represented by the following structural formula was spin coated with an electron-accepter compound (A-2) represented by the following structural formula under conditions described below.

[Compound 99]

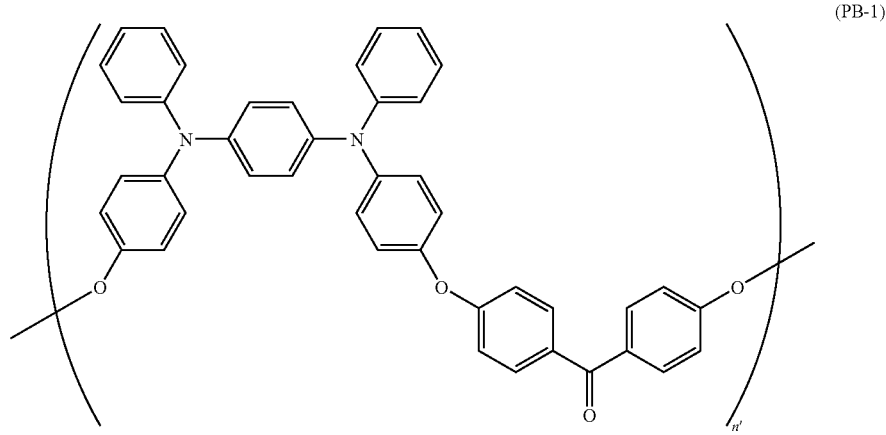

(PB-1)

[Compound 100]

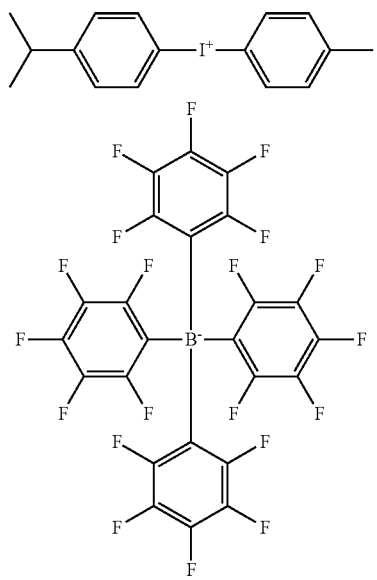

(A-2)

Spin coating conditions
Solvent ethyl benzoate
Coating concentration 2 [wt %]
PB-1:A-2 10:2 (weight ratio)
Spinner rotation speed 1500 [rpm]
Spinner rotation time 30 [sec]
Baking condition 230 [° C.]×15 [min]

A uniform thin film having a thickness of 30 nm was formed by the above-mentioned spin coating.

Then, the substrate on which the hole injection layer 3 was formed was placed in a vapor deposition chamber. The chamber was roughly evacuated with an oil rotary pump and then evacuated with a cryopump to $6.2 \times 10^{-5}$ Pa (about $4.7 \times 10^{-7}$ Torr) or less. The vapor deposition was carried out by heating an arylamine compound (H-1) shown below in a ceramic crucible arranged in the chamber using a tantalum wire heater disposed around the crucible. The temperature of the crucible was controlled in the range of 318 to 334° C. A hole transport layer 4 having a thickness of 40 nm was formed at $7.0 \times 10^{-5}$ Pa (about $5.3 \times 10^{-7}$ Torr) during the vapor deposition and a deposition rate of 0.21 nm/sec.

[Compound 101]

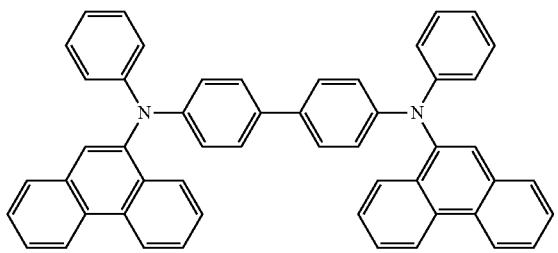

(H-1)

Then, a carbazole derivative (CBP) as a main component (host material) and an organic iridium complex (D-1) as a second component (dopant) were placed in separate ceramic crucibles, and a light-emitting layer 5 was formed by vapor co-deposition.

[Compound 102]

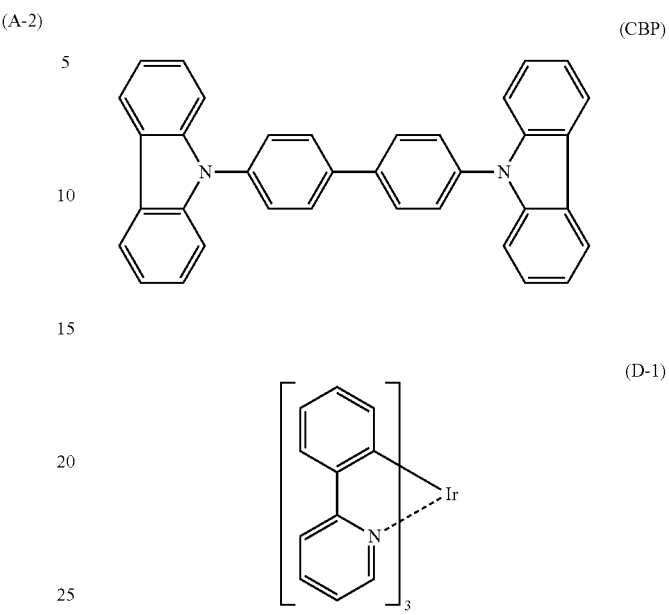

(CBP)

(D-1)

The crucible temperature of the compound (CBP) was controlled to 295 to 299° C., the deposition rate was controlled to 0.11 nm/sec, and the crucible temperature of the compound (D-1) was controlled to 252 to 255° C. Consequently, a light-emitting layer 5 having a thickness of 30 nm and containing about 6 wt % of the compound (D-1) was deposited on the hole transport layer 4. The pressure during the vapor deposition was $6.7 \times 10^{-5}$ Pa (about $5.0 \times 10^{-7}$ Torr).

Furthermore, a pyridine derivative (HB-1) shown below was deposited at a crucible temperature of 211 to 215° C. and a deposition rate of 0.09 nm/sec to form a hole blocking layer 6 having a thickness of 5 nm. The pressure during the vapor deposition was $6.2 \times 10^{-5}$ Pa (about $4.7 \times 10^{-7}$ Torr).

[Compound 103]

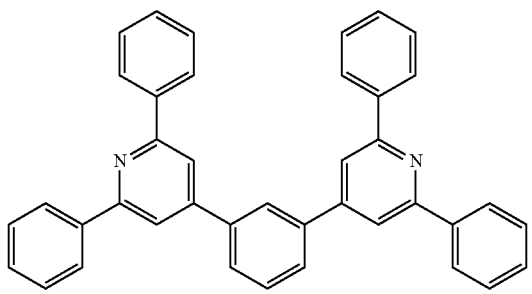

(HB-1)

Then, similarly, aluminum 8-hydroxyquinoline complex (ET-1) was deposited on the hole blocking layer 6 as an electron transport layer 7. On this occasion, the electron transport layer 7 having a thickness of 30 nm was obtained by controlling the crucible temperature of aluminum 8-hydroxyquinoline complex to 234 to 245° C., the pressure during the vapor deposition to $6.0 \times 10^{-5}$ Pa (about $4.5 \times 10^{-7}$ Torr), and the deposition rate to 0.22 nm/sec.

[Compound 104]

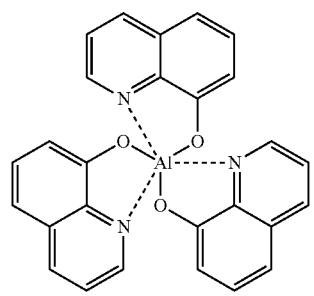

(ET-1)

The substrate temperature when the above-described hole injection layer 3, hole transport layer 4, light-emitting layer 5, hole blocking layer 6, and electron transport layer 7 were deposited was maintained at room temperature.

The element having formed thereon layers up to the electron transport layer 6 was once taken out of the vacuum deposition chamber into the air. A shadow mask for cathode deposition having a 2 mm wide stripe pattern was brought into contact with the device with the stripes thereof being orthogonal to the stripes of the ITO anode 2. The element was placed in another vacuum deposition chamber. The chamber was evacuated to $2.0 \times 10^{-6}$ Torr (about $2.7 \times 10^{-4}$ Pa) or less in the same manner as for the organic layer formation. In order to form a cathode 8, first, lithium fluoride (LiF) was evaporated on the electron transport layer 7 using a molybdenum boat at a deposition rate of 0.03 nm/sec and a pressure of $2.8 \times 10^{-6}$ Torr (about $3.7 \times 10^{-4}$ Pa) to form a film having a thickness of 0.5 nm. Then, aluminum was similarly evaporated by heating with a molybdenum boat at a deposition rate of 0.46 nm/sec and a pressure of $9.6 \times 10^{-6}$ Torr (about $1.3 \times 10^{-3}$ Pa) to form an aluminum layer having a thickness of 80 nm. Thus, a cathode 8 was completed. The substrate temperature during the vapor deposition of the double-layered cathode 8 was maintained at room temperature.

As described above, an organic electroluminescent device including a light-emitting area having the size 2 mm times 2 mm was obtained. The luminous properties of this element were as follows:

Luminance/current density: 24.7 [cd/A]@2.5 mA/cm$^2$
Voltage: 6.0 [V]@2.5 mA/cm$^2$
Luminous efficiency: 20.7 [lm/w]@100 cd/m$^2$
Luminance retention rate: 0.97@250 mA/cm$^2$ Here, the term "luminance holding ratio" means a value obtained by dividing a luminance (L) level at 50 sec after the start of driving at 250 mA/cm$^2$ by the luminance (L$_0$) level at the start of the driving. The luminance holding ratio is an indicator of driving stability.

The maximum wavelength of emission spectrum of the device was 512 nm and was identified to be from organic iridium complex (D-1). The chromaticity was CIE(x,y)=(0.30, 0.59).

Reference Example 2

Fabrication of Standard Device 2

A device having a structure shown in FIG. 4 was fabricated in the same manner as standard element 1 except that the hole blocking layer made of the pyridine derivative (HB-1) was not deposited. Luminous properties of this element are shown in Table 1. In Table 1, the values showing luminous properties are comparative values provided that the values of standard device 1 are 1.00.

The maximum wavelength of emission spectrum of the element was 512 nm and the chromaticity was CIE(x,y)=(0.29, 0.60). These were identified to be from organic iridium complex (D-1). The light emission from organic iridium complex was obtained even if the hole blocking layer was not provided, but the luminous efficiency was low and the driving voltage was high, compared to those of standard device 1.

Example 1

A device was fabricated in the same manner as in standard device 1 in Reference Example 1 except that target compound 6 (EM-1 represented by a structural formula below) synthesized in synthesis example 3 was used instead of the carbazole derivative (CBP) as the main component (host material) of the light-emitting layer 5.

Luminous properties and life properties of this device are shown in Table 1.

The maximum wavelength of emission spectrum of the device was 513 nm and the chromaticity was CIE(x,y)=(0.30, 0.60). These were identified to be from organic iridium complex (D-1).

This device had high luminous efficiency, low driving voltage, and long driving life.

[Compound 105]

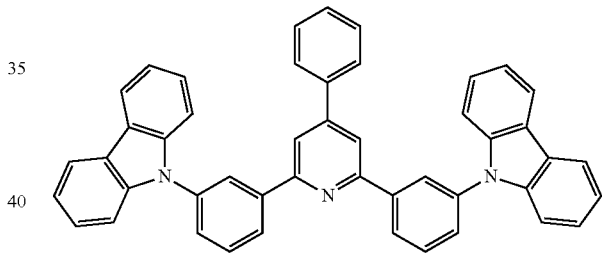

(EM-1)

Example 2

A device was fabricated in the same manner as in standard device 2 in Reference Example 2 except that target compound 6 (EM-1 represented by a structural formula above) synthesized in synthesis example 3 was used instead of the carbazole derivative (CBP) as the main component (host material) of the light-emitting layer 5.

Luminous properties and life properties of this device are shown in Table 1.

The maximum wavelength of emission spectrum of the device was 513 nm and the chromaticity was CIE(x,y)=(0.30, 0.60). These were identified to be from organic iridium complex (D-1).

This device had high luminous efficiency, low driving voltage, and long driving life.

By comparing the properties of standard elements 1 and 2 and the properties of the devices in Examples 1 and 2, it was confirmed that the devices in Examples 1 and 2 using an organic compound according to the present invention had high luminous efficiency and low driving voltage and were thus stable regardless of whether the hole blocking layer is present or not.

Example 3

A device was fabricated in the same manner as Example 2 except that target compound 2 (EM-2 represented by a structural formula below) synthesized in synthesis example 1 was used instead of target compound 6 (EM-1) as the main component (host material) of the light-emitting layer 5.

Luminous properties and life properties of this device are shown in Table 1.

The maximum wavelength of emission spectrum of the device was 514 nm and the chromaticity was CIE(x,y)=(0.30, 0.60). These were identified to be from organic iridium complex (D-1).

This device had high luminous efficiency and low driving voltage and was thus stable.

[Compound 106]

(EM-2)

[Compound 107]

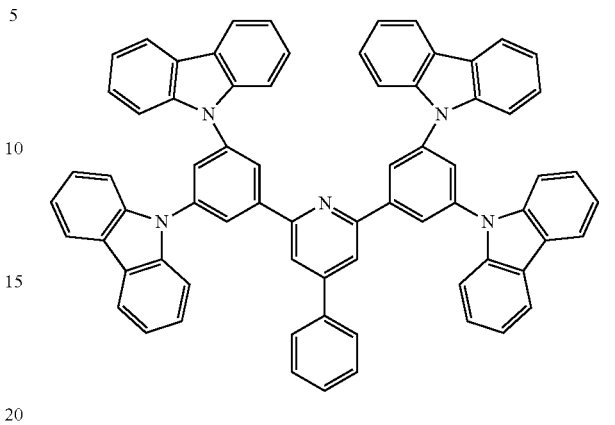

(EM-3)

Example 5

A device was fabricated in the same manner as Example 2 except that target compound 4 (EM-3 represented by a structural formula above) synthesized in synthesis example 2 was used instead of target compound 6 (EM-1) as the main component (host material) of the light-emitting layer 5.

Luminous properties of this device are shown in Table 1.

The maximum wavelength of emission spectrum of the device was 514 nm and the chromaticity was CIE(x,y)=(0.31, 0.60). These were identified to be from organic iridium complex (D-1).

This device had high luminous efficiency and low driving voltage.

By comparing the properties of standard elements 1 and 2 and the properties of the devices in Examples 4 and 5, it was confirmed that the devices in Examples 4 and 5 using an organic compound according to the present invention had high luminous efficiency and low driving voltage and were thus stable regardless of whether the hole blocking layer is present or not.

Example 4

A device was fabricated in the same manner as Example 1 except that target compound 4 (EM-3 represented by a structural formula below) synthesized in synthesis example 2 was used instead of target compound 6 (EM-1) as the main component (host material) of the light-emitting layer 5.

Luminous properties of this device are shown in Table 1.

The maximum wavelength of emission spectrum of the device was 514 nm and the chromaticity was CIE(x,y)=(0.31, 0.60). These were identified to be from organic iridium complex (D-1).

This device had high luminous efficiency and low driving voltage.

Example 6

A device was fabricated in the same manner as Example 1 except that target compound 18 (EM-4 represented by a structural formula below) synthesized in synthesis example 8 was used instead of target compound 6 (EM-1) as the main component (host material) of the light-emitting layer 5.

Luminous properties of this device are shown in Table 1.

The maximum wavelength of emission spectrum of the device was 513 nm and the chromaticity was CIE(x,y)=(0.30, 0.59). These were identified to be from organic iridium complex (D-1).

Luminous efficiency of this device was slightly low, but the driving life was long.

[Compound 108]

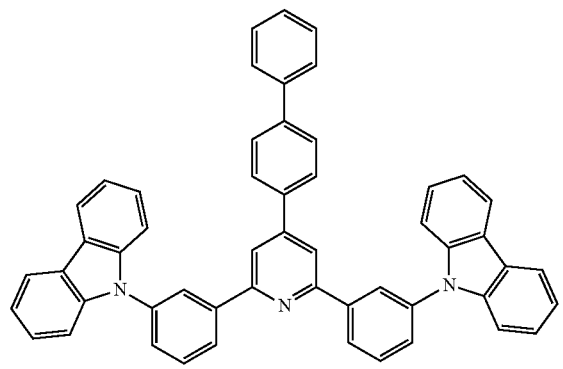

(EM-4)

[Compound 109]

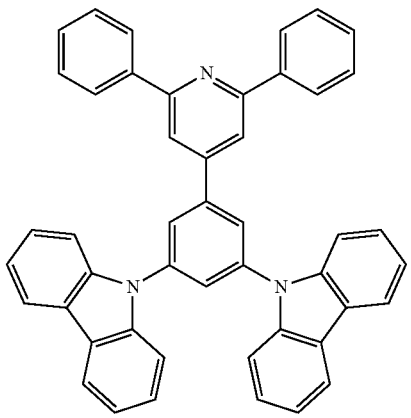

(EM-11)

Example 7

A device was fabricated in the same manner as Example 2 except that target compound 18 (EM-4 represented by a structural formula above) synthesized in synthesis example 8 was used instead of target compound 6 (EM-1) as the main component (host material) of the light-emitting layer 5.

Luminous properties and life properties of this device are shown in Table 1.

The maximum wavelength of emission spectrum of the device was 513 nm and the chromaticity was CIE(x,y)=(0.30, 0.58). These were identified to be from organic iridium complex (D-1).

Luminous efficiency of this device was slightly low, but the driving life was long.

Comparative Example 1

A device was fabricated in the same manner as Example 1 except that (EM-11) shown below was used instead of target compound (EM-1) as the main component (host material) of the light-emitting layer 5.

Luminous properties and life properties of this device are shown in Table 1.

The maximum wavelength of emission spectrum of the device was 514 nm and the chromaticity was CIE(x,y)=(0.31, 0.61). These were identified to be from organic iridium complex (D-1).

This device had low luminous efficiency compared to standard device 1 and the device in Example 1. In addition, the driving life was short compared to that of the device in Example 1.

Comparative Example 2

A device was fabricated in the same manner as Example 2 except that (EM-11) shown above was used instead of target compound (EM-1) as the main component (host material) of the light-emitting layer 5.

Luminous properties and life properties of this device are shown in Table 1.

The maximum wavelength of emission spectrum of the device was 514 nm and the chromaticity was CIE(x,y)=(0.31, 0.61). These were identified to be from organic iridium complex (D-1).

This device had low luminous efficiency compared to the device in Example 2. In addition, the driving life was short.

Comparative Example 3

A device was fabricated in the same manner as Example 1 except that (EM-12) shown below was used instead of target compound (EM-1) as the main component (host material) of the light-emitting layer 5.

Luminous properties of this device are shown in Table 1.

The maximum wavelength of emission spectrum of the device was 514 nm and the chromaticity was CIE(x,y)=(0.30, 0.60). These were identified to be from organic iridium complex (D-1).

This device had high luminous efficiency and low driving voltage compared to standard device 1, like the device in Example 3. However, it was observed that the device had low luminance holding ratio and was lacking in driving stability, unlike the element in Example 3.

[Compound 110]

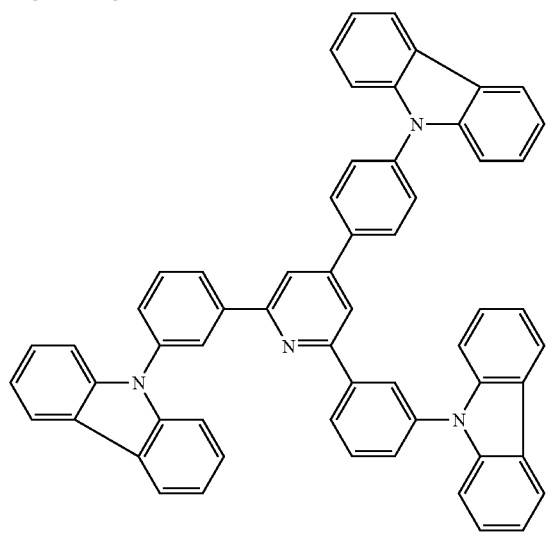

(EM-12)

Comparative Example 4

A device was fabricated in the same manner as Example 2 except that (EM-12) shown above was used instead of target compound (EM-1) as the main component (host material) of the light-emitting layer 5.

Luminous properties of this device are shown in Table 1.

The maximum wavelength of emission spectrum of the device was 514 nm and the chromaticity was CIE(x,y)=(0.30, 0.60). These were identified to be from organic iridium complex (D-1).

This device had high luminous efficiency and low driving voltage compared to standard device 1, like the device in Example 3. However, it was observed that the device had low luminance holding ratio and was lacking in driving stability, unlike the device in Example 3.

Example 8

A device was fabricated in the same manner as Example 1 except that target compound 23 (EM-5 represented by a structural formula below) synthesized in synthesis example 10 was used instead of target compound 6 (EM-1) as the main component (host material) of the light-emitting layer 5.

Luminous properties of this device are shown in Table 1.

The maximum wavelength of emission spectrum of the device was 513 nm and the chromaticity was CIE(x,y)=(0.30, 0.60). These were identified to be from organic iridium complex (D-1).

This device had high luminous efficiency, low driving voltage, and long driving life.

[Compound 111]

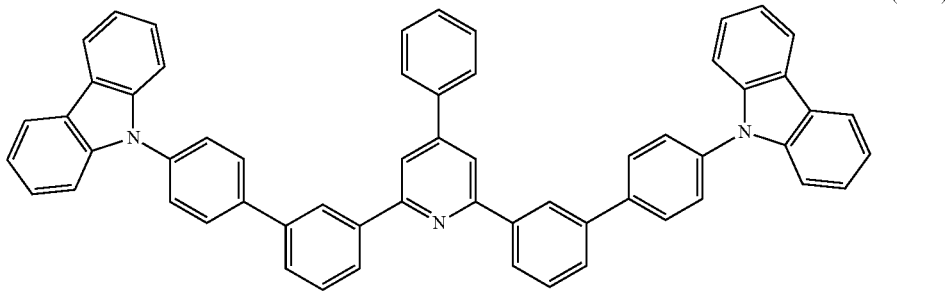

(EM-5)

Example 9

A device was fabricated in the same manner as Example 2 except that target compound 23 (EM-5 represented by a structural formula above) synthesized in synthesis example 10 was used instead of target compound 6 (EM-1) as the main component (host material) of the light-emitting layer 5.

Luminous properties of this device are shown in Table 1.

The maximum wavelength of emission spectrum of the device was 513 nm and the chromaticity was CIE(x,y)=(0.29, 0.59). These were identified to be from organic iridium complex (D-1).

This device had high luminous efficiency and low driving voltage.

By comparing the properties of standard devices 1 and 2 and the properties of the devices in Examples 8 and 9, it was confirmed that the devices in Examples 8 and 9 using an organic compound according to the present invention had high luminous efficiency and low driving voltage and were thus stable regardless of whether the hole blocking layer is present or not.

Example 10

A device was fabricated in the same manner as Example 1 except that target compound 13 (EM-6 represented by a structural formula below) synthesized in synthesis example 6 was used instead of target compound 6 (EM-1) as the main component (host material) of the light-emitting layer 5.

Luminous properties of this device are shown in Table 1.

The maximum wavelength of emission spectrum of the device was 514 nm and the chromaticity was CIE(x,y)=(0.30, 0.60). These were identified to be from organic iridium complex (D-1).

[Compound 112]

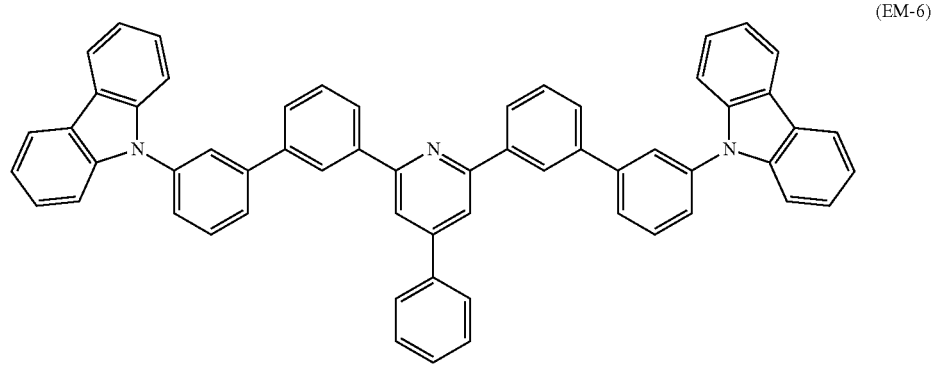

(EM-6)

Example 11

A device was fabricated in the same manner as Example 2 except that target compound 13 (EM-6 represented by a structural formula above) synthesized in synthesis example 6 was used instead of target compound 6 (EM-1) as the main component (host material) of the light-emitting layer 5.

Luminous properties of this device are shown in Table 1.

The maximum wavelength of emission spectrum of the device was 513 nm and the chromaticity was CIE(x,y)=(0.30, 0.60). These were identified to be from organic iridium complex (D-1).

By comparing the properties of the devices in Examples 10 and 11 with those of standard devices 1 and 2, it was confirmed that the devices in Examples 10 and 11 using an organic compound according to the present invention had long driving life and were thus stable regardless of whether the hole blocking layer is present or not.

TABLE 1

| | Property of Device | | Luminous Property of Element | | | | Life Property of Element | | |
|---|---|---|---|---|---|---|---|---|---|
| | | | Luminance/current density (@2.5 mA/cm$^2$) | Voltage (@2.5 mA/cm$^2$) | Luminous Efficiency (@100 cd/m$^2$) | Luminance Holding Ratio (@250 mA/cm$^2$) | (@2,500 cd/m$^2$) | | |
| | Host Material of Light-Emitting Layer | Hole Blocking Material | | | | | Operating Life 1 | Operating Life 2 | Operating Life 3 |
| Standard Device 1 | CBP | HB-1 | 1.00 | 1.00 | 1.00 | 1.00 | | 1.00 | 1.00 |
| Standard Device 2 | CBP | — | 0.6 | 1.15 | 0.52 | 1.03 | 1.00 | | |
| Example 1 | EM-1 | HB-1 | 1.25 | 0.97 | 1.29 | 0.99 | 2.63 | 1.05 | |
| Example 2 | EM-1 | — | 1.22 | 0.91 | 1.34 | 0.99 | 2.88 | 1.12 | |
| Example 3 | EM-2 | — | 1.10 | 0.86 | 1.28 | 0.99 | 1.26 | | |
| Example 4 | EM-3 | HB-1 | 1.02 | 0.87 | 1.17 | 0.92 | | | |
| Example 5 | EM-3 | — | 0.97 | 0.78 | 1.24 | 0.92 | | | |
| Example 6 | EM-4 | HB-1 | 0.89 | 1.08 | 0.83 | 0.98 | 4.40 | 1.63 | |
| Example 7 | EM-4 | — | 0.86 | 1.00 | 0.85 | 0.98 | 3.53 | 1.28 | |
| Example 8 | EM-5 | HB-1 | 1.00 | 0.95 | 1.01 | 0.98 | | | 1.24 |
| Example 9 | EM-5 | — | 1.00 | 0.86 | 1.03 | 0.99 | | | |
| Example 10 | EM-6 | HB-1 | 0.82 | 1.21 | 0.61 | 0.99 | | | 1.97 |
| Example 11 | EM-6 | — | 0.80 | 1.77 | 0.60 | 0.99 | | | 1.44 |
| Comparative Example 1 | EM-11 | HB-1 | 0.84 | 1.13 | 0.74 | 0.96 | 0.66 | 0.28 | |
| Comparative Example 2 | EM-11 | — | 0.85 | 1.04 | 0.81 | 0.97 | 0.66 | 0.26 | |
| Comparative Example 3 | EM-12 | HB-1 | 1.14 | 0.92 | 1.24 | 0.74 | | | |
| Comparative Example 4 | EM-12 | — | 1.01 | 0.83 | 1.22 | 0.74 | | | |

Example 12

A device was fabricated in the same manner as Example 2 except that target compound 24 (EM-7 represented by a structural formula below) synthesized in synthesis example 11 was used instead of target compound 6 (EM-1) as the main component (host material) of the light-emitting layer 5.

The maximum wavelength of emission spectrum of the device was 513 nm and the chromaticity was CIE(x,y)=(0.30, 0.59). These were identified to be from organic iridium complex (D-1).

[Compound 113]

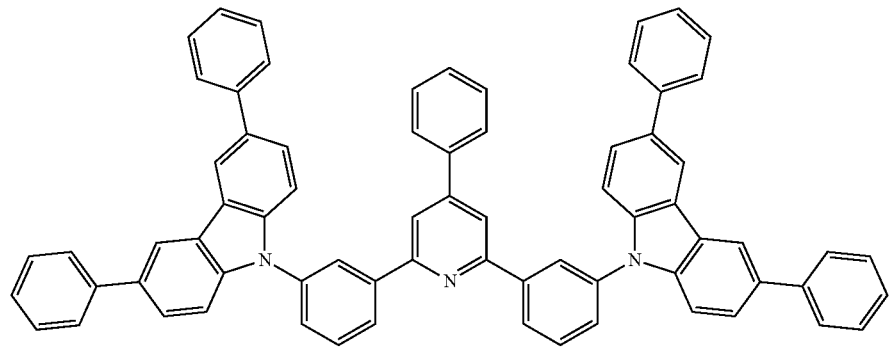

(EM-7)

Example 13

A device was fabricated in the same manner as Example 2 except that target compound 20 (EM-8 represented by a structural formula below) synthesized in synthesis example 9 was used instead of target compound 6 (EM-1) as the main component (host material) of the light-emitting layer 5.

The maximum wavelength of emission spectrum of the device was 518 nm and the chromaticity was CIE(x,y)=(0.35, 0.59). These were identified to be from organic iridium complex (D-1).

[Compound 114]

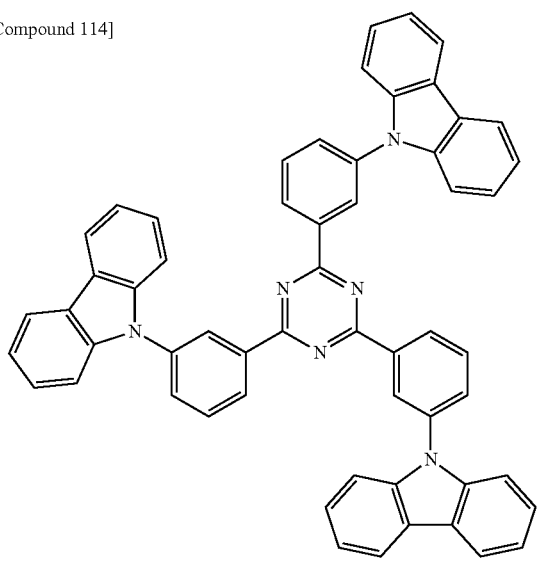

(EM-8)

Example 14

A device was fabricated in the same manner as Example 2 except that target compound 10 (EM-9 represented by a structural formula below) synthesized in synthesis example 5 was used instead of target compound 6 (EM-1) as the main component (host material) of the light-emitting layer 5.

The maximum wavelength of emission spectrum of the device was 518 nm and the chromaticity was CIE(x,y)=(0.35, 0.59). These were identified to be from organic iridium complex (D-1).

[Compound 115]

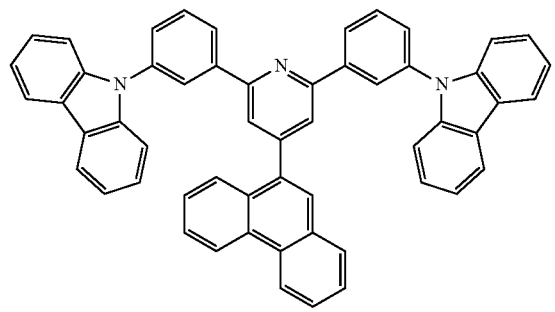

(EM-9)

Example 15

A device was fabricated in the same manner as Example 2 except that target compound 16 (EM-10 represented by a structural formula below) synthesized in synthesis example 7 was used instead of target compound 6 (EM-1) as the main component (host material) of the light-emitting layer 5.

The maximum wavelength of emission spectrum of the device was 513 nm and the chromaticity was CIE(x,y)=(0.30, 0.60). These were identified to be from organic iridium complex (D-1).

[Compound 116]

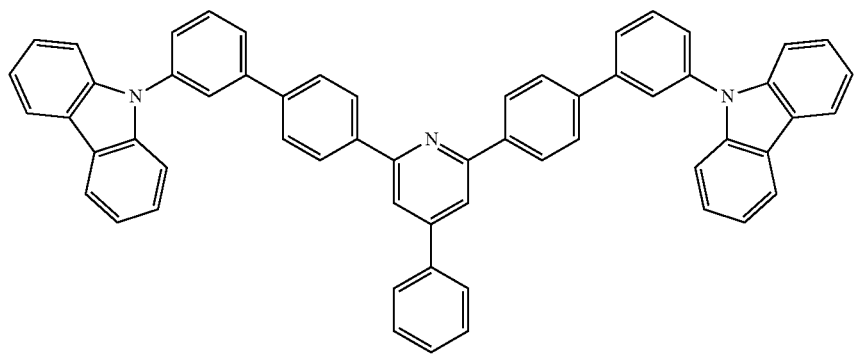

(EM-10)

Although the present invention has been described in detail with reference to specific embodiments, it will be apparent to those skilled in the art that various changes can be made without departing from the spirit and scope of the present invention. Further, the present invention is based on Japanese Patent Application (Patent Application No. 2004-358592) filed on Dec. 10, 2004, the entire content of which is hereby incorporated by reference.

The invention claimed is:

1. An organic compound comprising two or more partial structures represented by the following Formula (I):

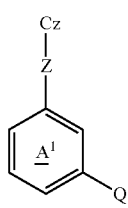

(I)

wherein Cz denotes a carbazolyl group;
Z denotes a direct link or an optional linking group;
Cz, Z, and an $A^1$ ring may have a substituent;
the Cz's may be the same or different;
the Z's may be the same or different;
the $A^1$ rings may be the same or different;
Q denotes a direct link connecting to G present in a moiety represented by one of the following Formulae (II-1) to (II-4), and the number of groups represented by any of Formulae (II-1) to (II-4) in said compound is one,

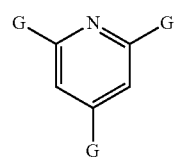

(II-1)

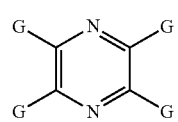

(II-2)

-continued (II-3)

(II-4)

when G is linked to Q, the G denotes a direct link or an optional linking group which links to Q;
when G is not linked to Q, the G denotes an aromatic hydrocarbon group;
the G's may be the same or different; and
rings in the Formulae (II-1) to (II-4) may have a substituent in addition to G.

2. The organic compound according to claim 1, wherein the moiety represented by Formula (II-1) is present.

3. The organic compound according to claim 1, wherein Formula (I) is represented by the following Formula (I-1):

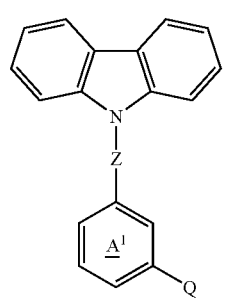

(I-1)

wherein Z, $A^1$ ring, and Q are the same as those in Formula (I).

4. The organic compound according to claim 1, wherein G and Z are each a direct link or -(Ph)$_p$- (where Ph denotes a phenylene group which may have a substituent, and p is an integer of 1 to 8).

5. The organic compound according to claim 1, the organic compound being represented by the following Formula (III):

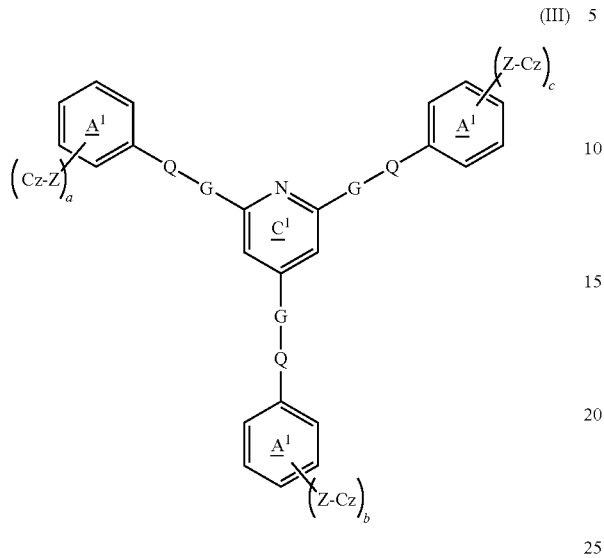

(III)

wherein Cz, Z, $A^1$ ring, and Q are the same as those in Formula (I), and G is the same as that in Formulae (II-1) to (II-4);
a, b, and c each denote the number of Z-Cz;
a, b, and c are each independently an integer of 0 to 5;
a+b+c is an integer not less than 2; and
the 3-position and/or 5-position of $C^1$ ring may be substituted with an optional substituent, and wherein
Z-Cz groups are present in a meta position to Q on at least two $A^1$ rings.

6. The organic compound according to claim 5, wherein a and c in Formula (III) are each 1.

7. The organic compound according to claim 5, wherein b in Formula (III) is 0 or 1.

8. The organic compound according to claim 5, wherein G in Formula (III) is represented by $-(Ph)_p-$ (where Ph denotes a phenylene group which may have a substituent, and p is an integer of 1 to 8).

9. The organic compound according to claim 1, wherein N atoms which do not conjugate with each other are not linked with the following partial structures:

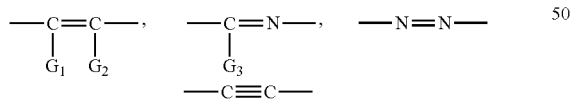

wherein $G_1$, $G_2$, and $G_3$ each independently denote a hydrogen atom or an optional substituent or constitute part of an aromatic hydrocarbon ring or an aromatic heterocycle.

10. The organic compound according to claim 1, wherein one molecule of the organic compound comprises two or three partial structures represented by Formula (I).

11. The organic compound according to claim 1, wherein $A^1$ ring has only Z and Q as substituents.

12. The organic compound according to claim 1, wherein the partial structure represented by Formula (I) excluding the part represented by one of Formulae (II-1) to (II-4) is selected from the following V-1, V-2, V-3, V-5, V-6, and V-12:

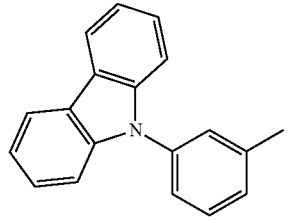

V-1

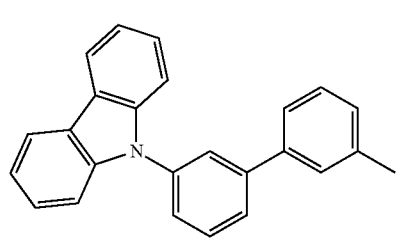

V-2

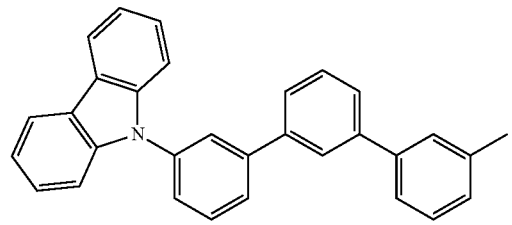

V-3

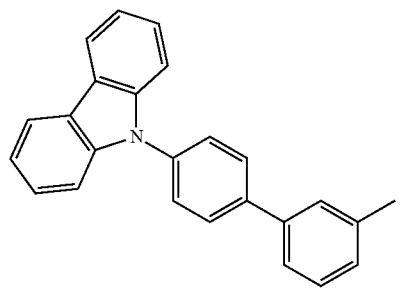

V-5

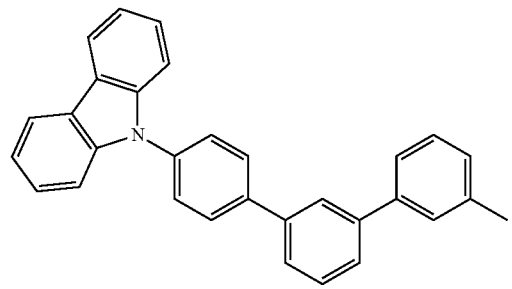

V-6

-continued

V-12

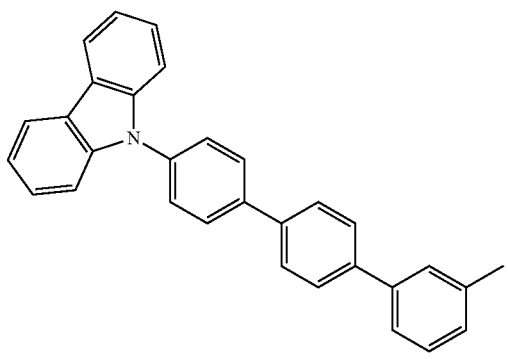

13. The organic compound according to claim 1, wherein the organic compound has a molecular weight of 200 to 4000.

14. The organic compound according to claim 1, wherein the organic compound has a glass transition temperature of 90° C. or more, a vaporization temperature of 700° C. or less, and a melting point of 150° C. or more.

15. The organic compound according to claim 5, wherein Formula (III) is represented by the following Formula (IV):

(IV)

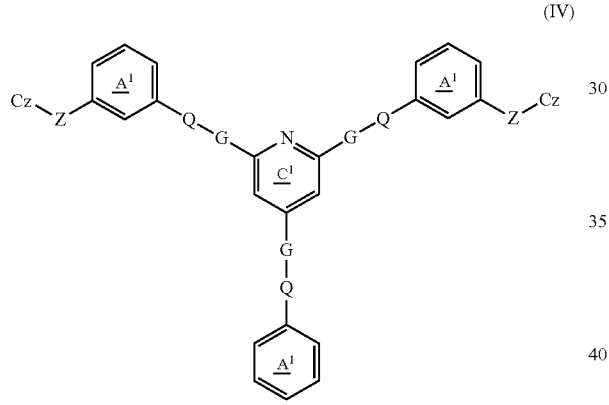

wherein Cz, Z, Q, and $A^1$ ring are the same as those in Formula (I), G is the same as that in Formulae (II-1) to (II-4), and $C^1$ ring is the same as that in Formula (III).

16. The organic compound according to claim 5, wherein Formula (III) is represented by the following Formula (V):

(V)

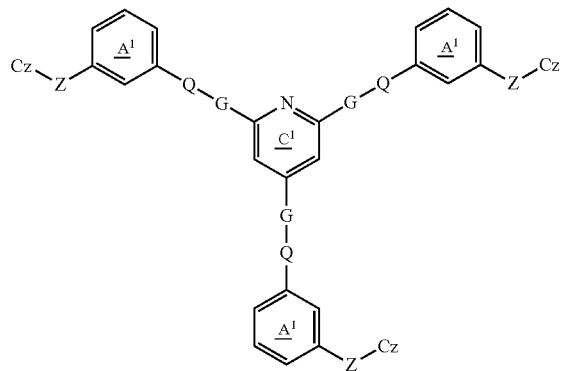

wherein Cz, Z, Q, and $A^1$ ring are the same as those in Formula (I), G is the same as that in Formulae (II-1) to (II-4), and $C^1$ ring is the same as that in Formula (III).

17. The organic compound according to claim 1, the organic compound being represented by the following structural formula:

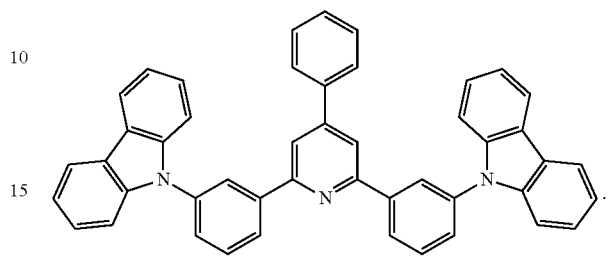

18. The organic compound according to claim 1, the organic compound being represented by the following structural formula:

(EM-2)

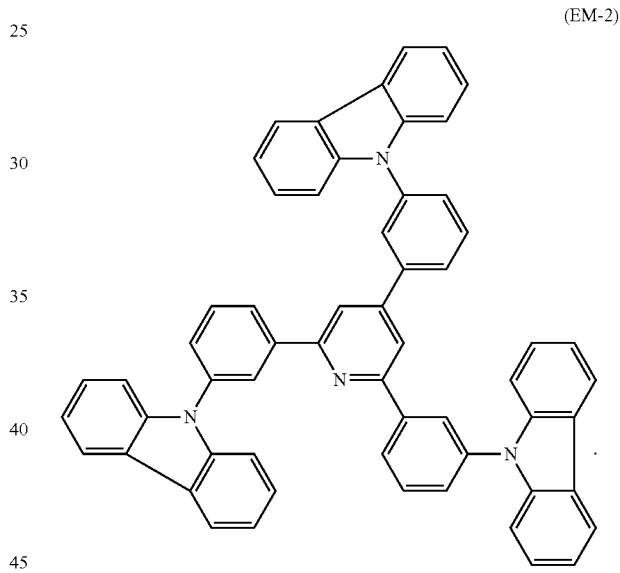

19. The organic compound according to claim 1, the organic compound being represented by the following structural formula:

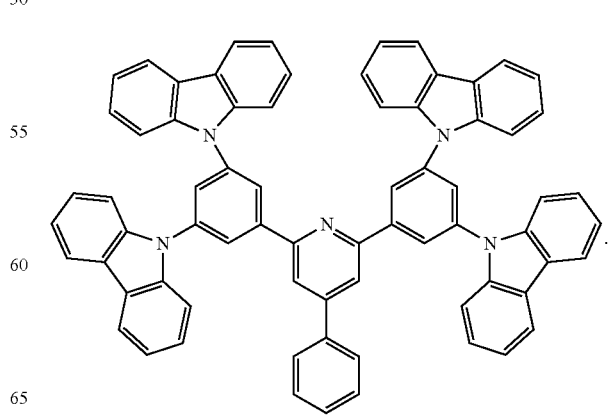

20. The organic compound according to claim 1, the organic compound being represented by the following structural formula:
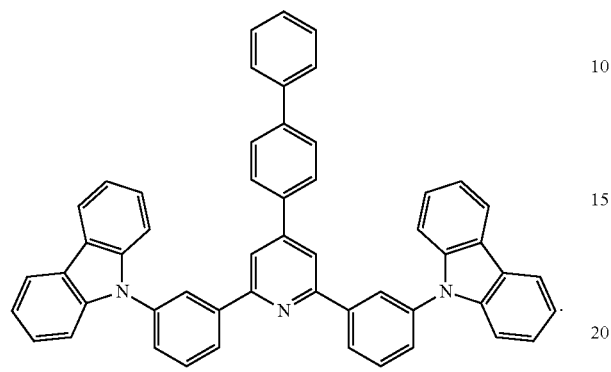
21. The organic compound according to claim 1, the organic compound being represented by the following structural formula:
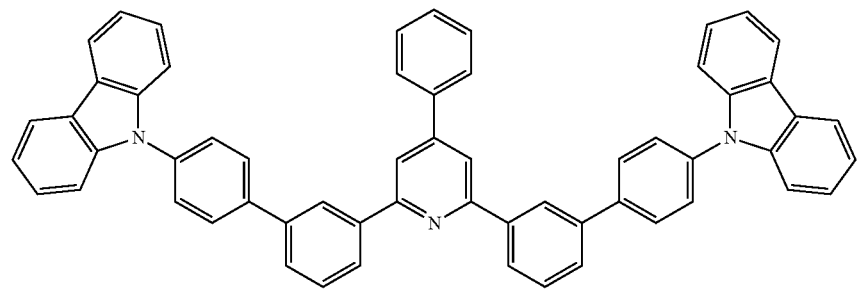
22. The organic compound according to claim 1, the organic compound being represented by the following structural formula:
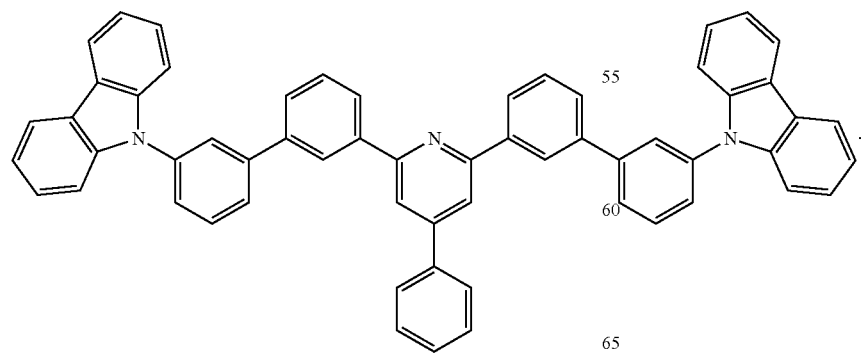

23. The organic compound according to claim 1, the organic compound being represented by the following structural formula:
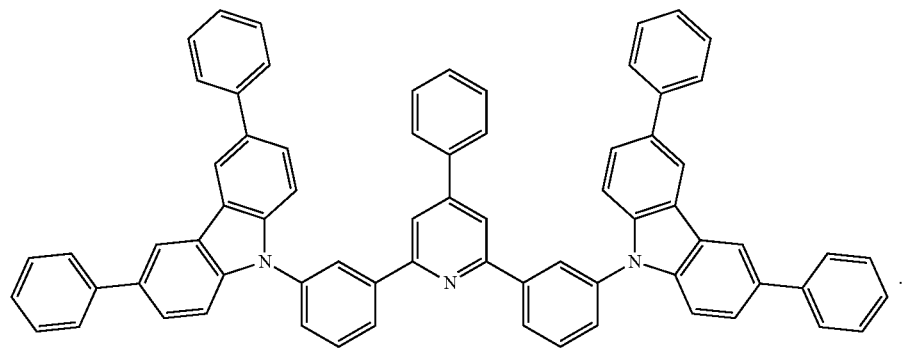
24. The organic compound according to claim 1, the organic compound being represented by the following structural formula:
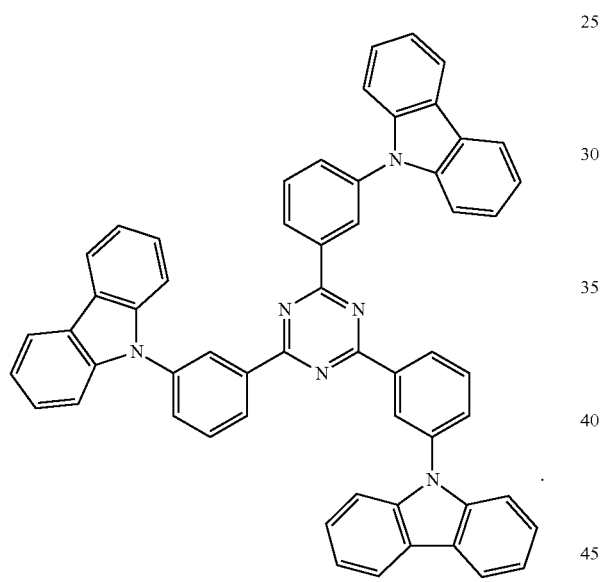
25. The organic compound according to claim 1, the organic compound being represented by the following structural formula:
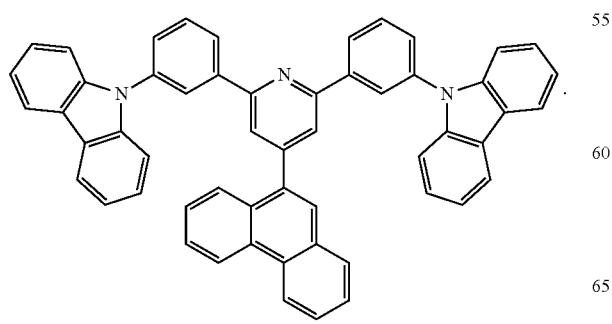

26. The organic compound according to claim 1, the organic compound being represented by the following structural formula:

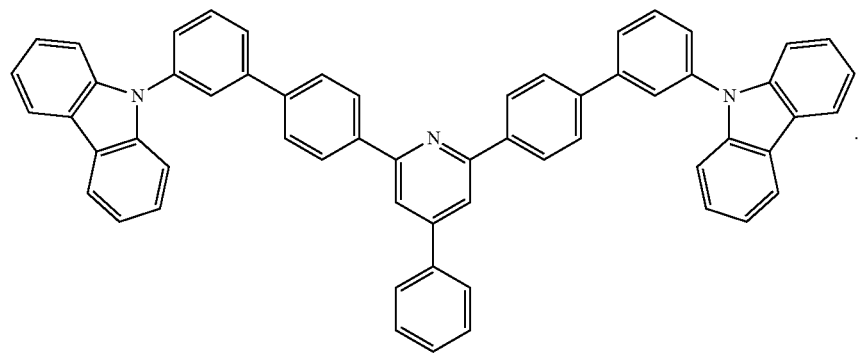

27. A charge-transporting material, the material contains an organic compound according to claim 1.

28. An organic electroluminescent device comprising an anode, a cathode, and an organic light-emitting layer disposed between the both electrodes on a substrate, the organic electroluminescent device having a layer containing an organic compound according to claim 1.

29. The organic electroluminescent device according to claim 28, wherein the layer containing the organic compound is the organic light-emitting layer.

30. The organic electroluminescent device according to claim 29, wherein the organic compound according to claim 1 is a host material of the organic light-emitting layer, and the host material is doped with an organometallic complex.

* * * * *